(12) United States Patent
Kuwata et al.

(10) Patent No.: US 11,219,114 B2
(45) Date of Patent: *Jan. 4, 2022

(54) RADIATION GENERATION CONTROL DEVICE, RADIATION GENERATION CONTROL SYSTEM, AND RADIOGRAPHY SYSTEM

(71) Applicant: Konica Minolta, Inc., Tokyo (JP)

(72) Inventors: Masahiro Kuwata, Machida (JP); Koutarou Kanamori, Hachioji (JP); Nobuyuki Miyake, Yokohama (JP); Kosuke Fukazu, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 119 days.

This patent is subject to a terminal disclaimer.

(21) Appl. No.: 16/574,197

(22) Filed: Sep. 18, 2019

(65) Prior Publication Data
US 2020/0120783 A1    Apr. 16, 2020

(30) Foreign Application Priority Data

Oct. 3, 2018  (JP) .............................. JP2018-188191
Oct. 3, 2018  (JP) .............................. JP2018-188272

(51) Int. Cl.
*G01N 23/04*    (2018.01)
*H05G 1/58*    (2006.01)
(Continued)

(52) U.S. Cl.
CPC ............... *H05G 1/58* (2013.01); *G01N 23/04* (2013.01); *H05G 1/60* (2013.01); *A61B 6/4429* (2013.01); *A61B 6/485* (2013.01)

(58) Field of Classification Search
CPC ....... A61B 6/022; A61B 6/025; A61B 6/4429; A61B 6/465; A61B 6/485; A61B 6/487; A61B 6/5205; A61B 6/54; A61B 6/3122; A61B 6/58; A61B 6/4233; A61B 6/4283; A61B 6/542; A61B 6/566; A61B 6/4266;
(Continued)

(56) References Cited

U.S. PATENT DOCUMENTS 9,301,378 B2 *  3/2016  Booker ................... G01T 1/247
10,368,826 B2 *  8/2019  Tamura ..................... H05G 1/34
(Continued)

FOREIGN PATENT DOCUMENTS

JP    H09-270955 A    10/1997
JP    2005287773 A    10/2005
(Continued)

*Primary Examiner* — Irakli Kiknadze
(74) *Attorney, Agent, or Firm* — Lucas & Mercanti, LLP

(57) ABSTRACT

A radiation generation control device includes an acquirer, a first connector, a second connector and a controller. The acquirer acquires a first signal which instructs emission of radiation. The first connector inputs a second signal which indicates a driving state of a radiography apparatus that generates a radiographic image. The second connector connects with a radiation generation apparatus that generates radiation. The controller makes the second connector repeatedly output a third signal which instructs emission of radiation with a predetermined period based on the acquired first signal and the input second signal.

20 Claims, 32 Drawing Sheets

(51) Int. Cl.
*H05G 1/60* (2006.01)
*A61B 6/00* (2006.01)

(58) Field of Classification Search
CPC ........... A61B 6/548; A61B 6/467; A61B 6/42; A61B 6/4405; A61B 6/56; A61B 6/032; A61B 6/037; A61B 6/4441; A61B 6/4494; A61B 6/481; A61B 6/4208; A61B 6/4411; A61B 6/563; A61B 6/545; A61B 6/486; A61B 6/44; A61B 6/463; A61B 6/5217; A61B 6/4452; A61B 6/40; A61B 6/469; A61B 6/586; G01N 23/04; G01N 21/66; G01N 2223/419; G01N 2223/612; G01N 23/046; G01N 23/044; G01N 23/083; G01N 2223/203; G01N 2223/3302; G01N 23/20075; G01N 2223/304; G01N 2021/1706; G01N 2021/95676; G01N 21/1702; G01N 2223/0745; G01N 2223/505; G01N 23/222; G01N 23/223; G01N 29/2425; G01N 223/612; G01N 23/041; G01T 1/026; G01T 1/1603; G01T 1/1611; G01T 1/2985; G01T 1/247; G01T 1/1615; G01T 1/1647; G01T 1/242; G01T 1/249; G01T 1/20; G01T 1/2018; G01T 1/244; G01T 1/246; G01T 1/2928; G01T 1/023; G01T 1/1614; G01T 1/17; G01T 1/208; G01T 7/005; G01T 1/15; G01T 1/24; G01T 7/00; G01T 1/603; G01T 1/2023; G01T 1/161; G01T 1/1663; G01T 1/172; G01T 1/08; G01T 1/16; G05B 11/06; G05B 13/041; G05B 19/0423; G05B 19/0425; G05B 19/106; G05B 19/414; G05B 1/03; G05B 23/0286; H01J 35/14; H01J 35/147; H01J 35/153; H04N 5/32; H05G 1/38; H05G 1/40; H05G 1/42; H05G 1/44; H05G 1/52; H05G 1/56; H05G 1/58; H05G 1/60; H05G 1/30; H05G 1/32; H05G 1/34; H05G 1/10; H05G 1/26; H05G 1/265; H05G 1/46; H03K 4/026; G01M 17/28; A61N 2005/1051; A61N 2005/1052; A61N 2005/1054; A61N 2005/1061; A61N 2205/1087; A61N 2005/1095; A61N 2005/1097; A61N 5/1037; A61N 5/1039; A61N 5/1049; A61N 5/1067; A61N 5/1069; A61N 5/107; A61N 5/1077; A61N 5/1081; A61N 5/1082; G21K 1/08; G21K 5/04; G21K 1/02
USPC ...................................... 378/62, 98, 114–119
See application file for complete search history.

(56) References Cited

U.S. PATENT DOCUMENTS

| | | | |
|---|---|---|---|
| 2009/0129546 A1 | 5/2009 | Newman et al. | |
| 2012/0128127 A1* | 5/2012 | Chicchetti | A61B 6/4405 378/62 |
| 2013/0230141 A1* | 9/2013 | Miyachi | G01N 23/04 378/62 |
| 2014/0161228 A1* | 6/2014 | Kitano | A61B 6/542 378/62 |
| 2014/0205066 A1* | 7/2014 | Kitagawa | A61B 6/542 378/62 |
| 2014/0254760 A1* | 9/2014 | Hiroike | A61B 6/4233 378/62 |
| 2015/0139398 A1* | 5/2015 | Tajima | H05G 1/38 378/62 |
| 2021/0033543 A1* | 2/2021 | Kuwata | G01N 23/04 |

FOREIGN PATENT DOCUMENTS

| | | |
|---|---|---|
| JP | 5203467 B2 | 2/2013 |
| WO | 2009067189 A1 | 5/2009 |

* cited by examiner

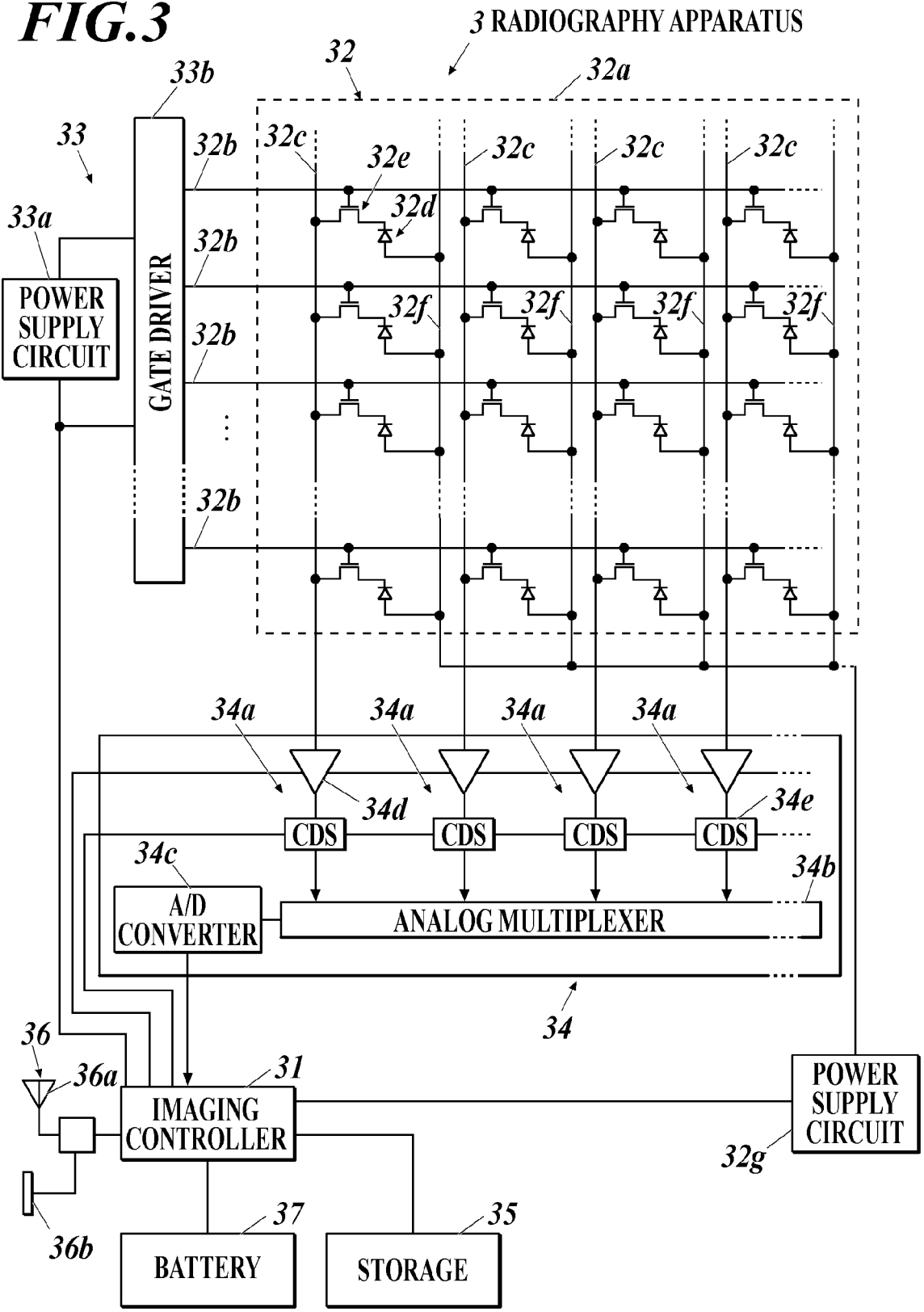

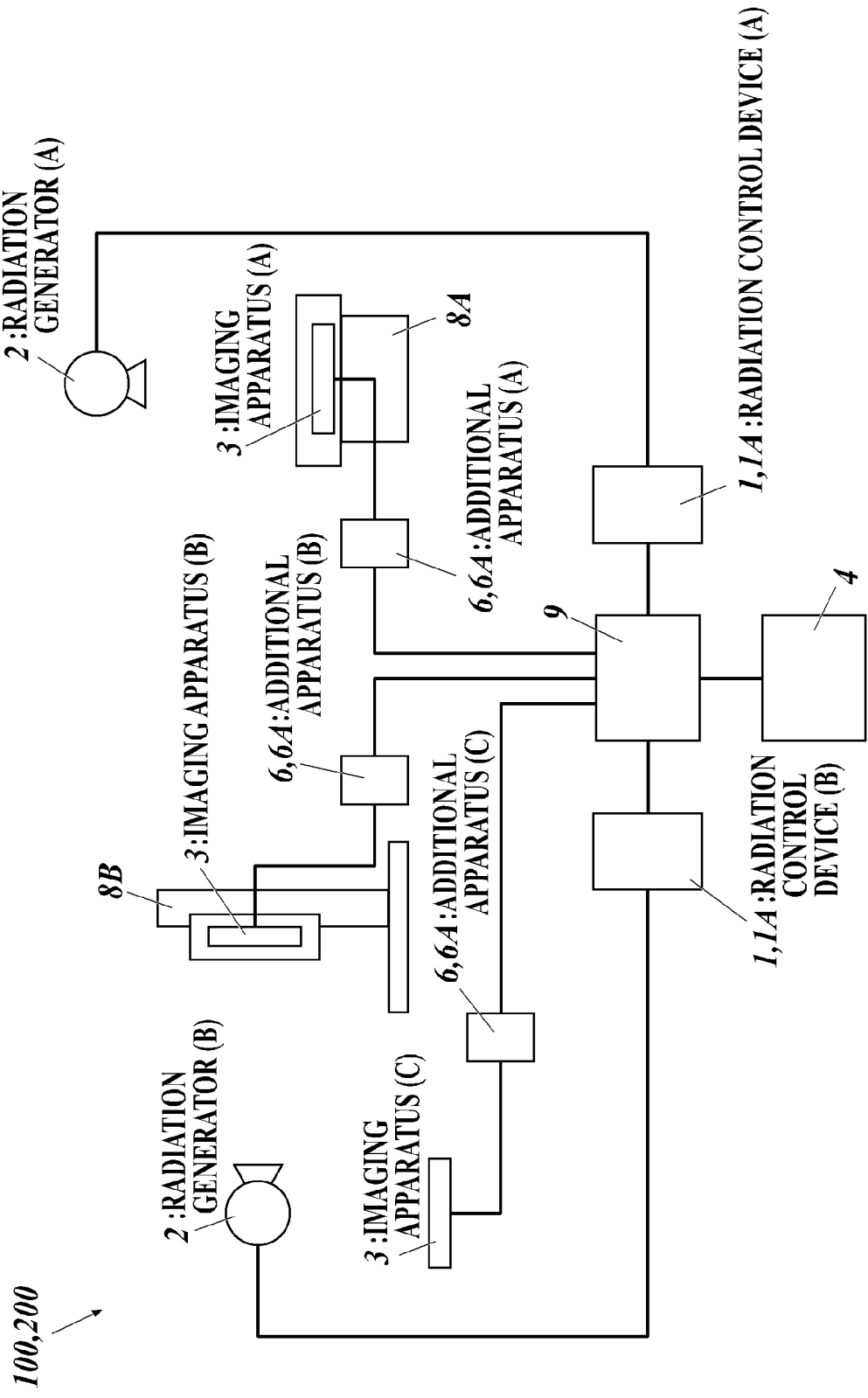

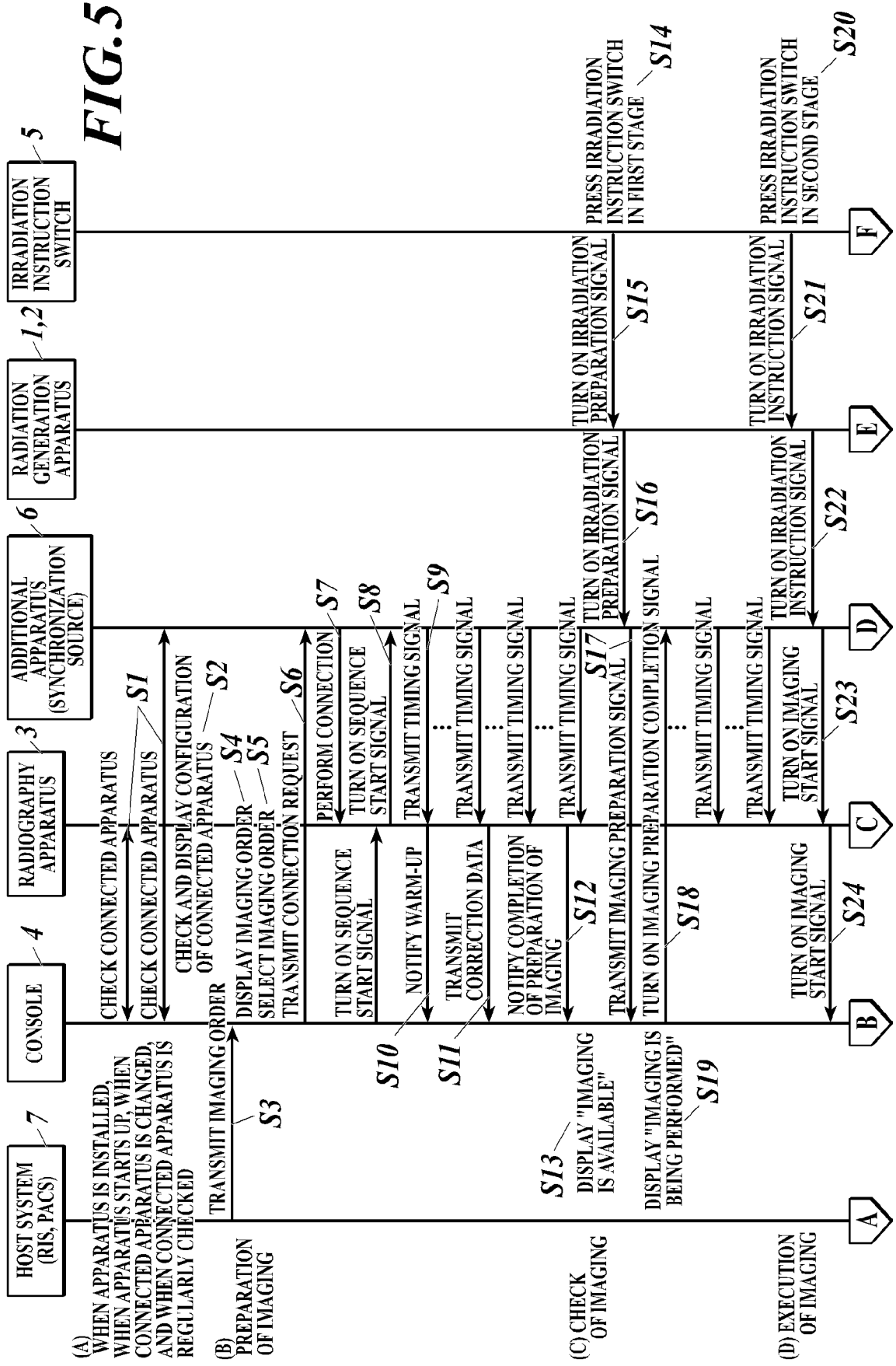

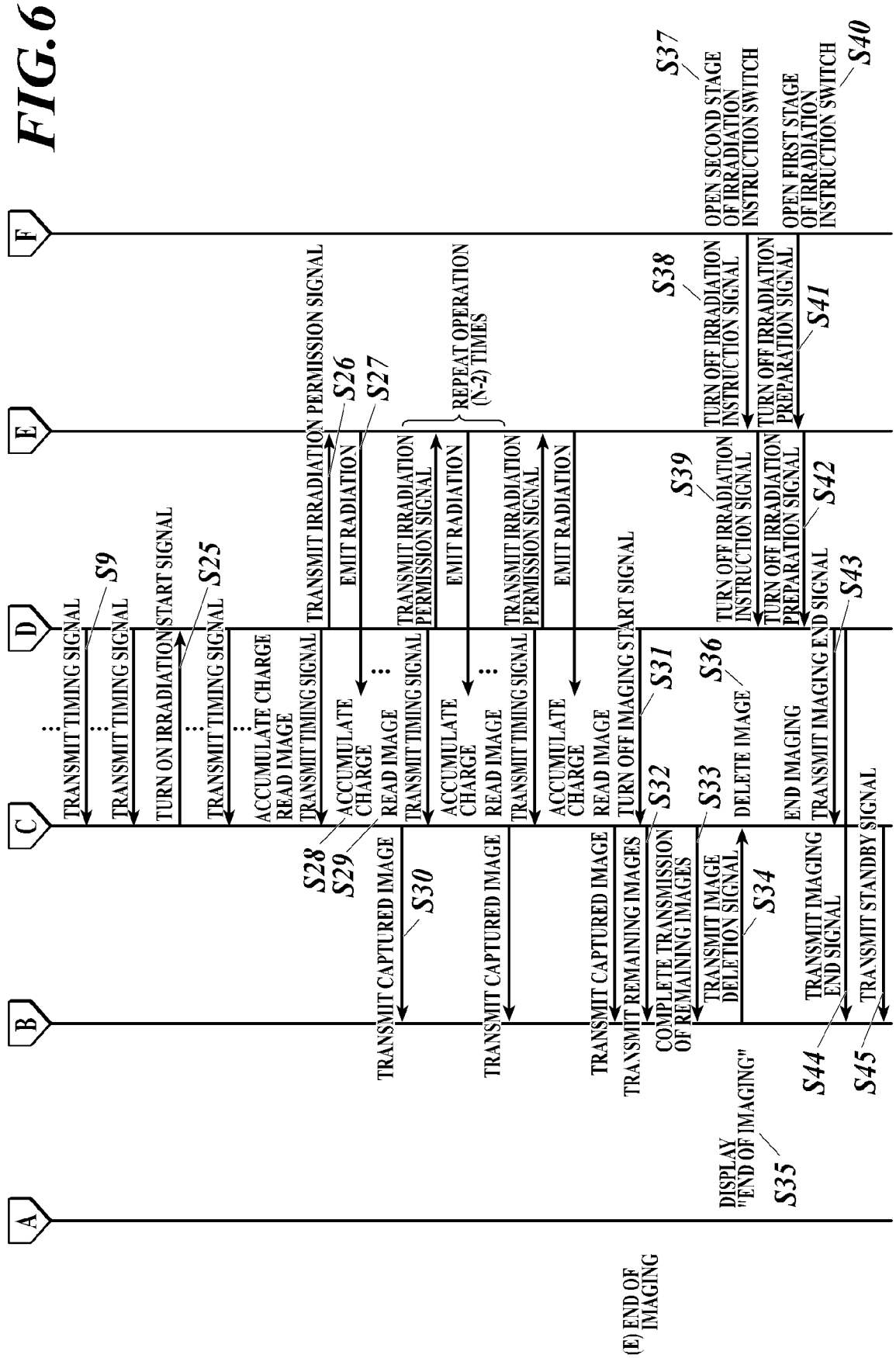

FIG. 7

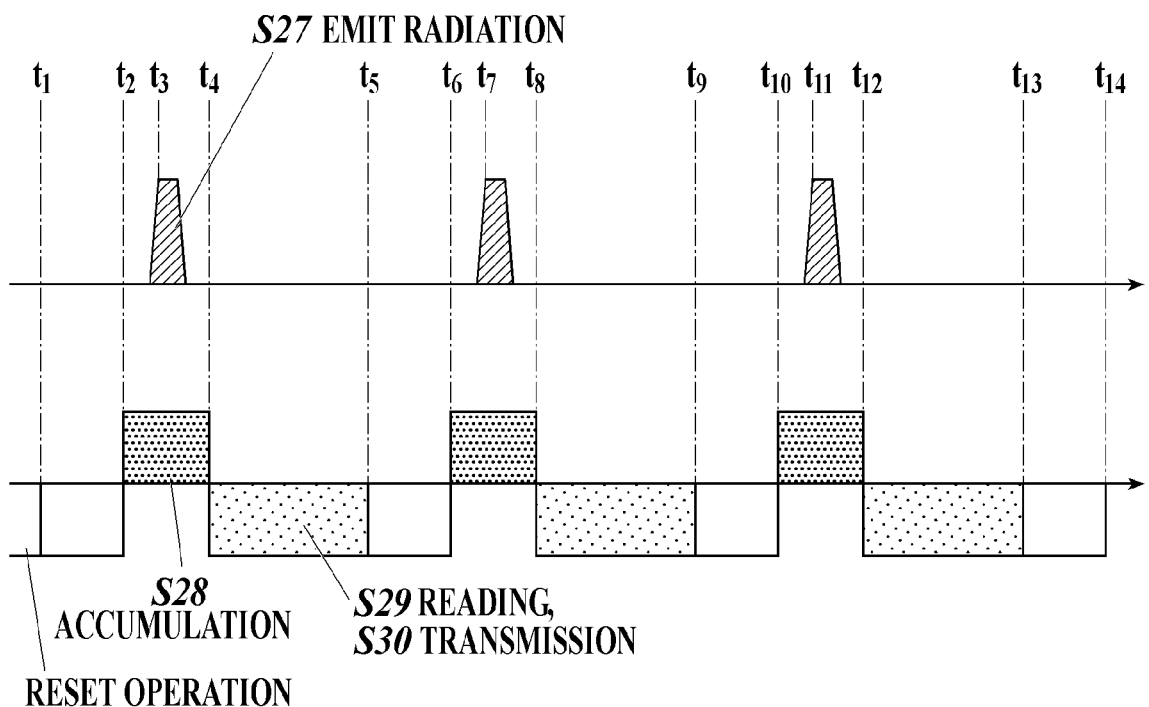

S27 EMIT RADIATION

S28 ACCUMULATION
RESET OPERATION
S29 READING,
S30 TRANSMISSION

FIG. 8

| APPARATUS | CORRESPONDING FRAME RATE | | |
|---|---|---|---|
| RADIOGRAPHY APPARATUS A | 15 FRAMES/S | | |
| | 7.5 FRAMES/S | | |
| | 3.75 FRAMES/S | | |
| RADIOGRAPHY APPARATUS C | 20 FRAMES/S | | |
| | 10 FRAMES/S | | |
| | 5 FRAMES/S | | |
| RADIATION GENERATION APPARATUS A | 15 FRAMES/S | | |
| | 10 FRAMES/S | | |
| | 5 FRAMES/S | | |
| RADIATION GENERATION APPARATUS B | 20 FRAMES/S | 12.5 FRAMES/S | 5 FRAMES/S |
| | 17.5 FRAMES/S | 10 FRAMES/S | 2.5 FRAMES/S |
| | 15 FRAMES/S | 7.5 FRAMES/S | |

FIG.9

| ORDER LIST | | |
|---|---|---|
| LUNG FIELD (STILL IMAGE) | | |
| LUNG FIELD (DYNAMIC IMAGE) | | |

| IMAGING TABLE |
|---|
| UPRIGHT IMAGING TABLE |
| UPRIGHT IMAGING TABLE (ELONGATED) |
| DECUBITUS IMAGING TABLE |
| DECUBITUS IMAGING TABLE (ELONGATED) |
| PANEL IMAGING |

43

AVAILABLE PANEL — 43b

IMAGING APPARATUS (A) — 14 × 17
- POWER 95%
- COMMUNICATION WIRED
- MEMORY CAPACITY 2.3G
- SIZE 1717
- RESOLUTION 100 / 200 μm
- CORRESPONDING IMAGING DYNAMIC IMAGING IS AVAILABLE
- F RATE 15 / 7.5 / 3.75Hz
- TRANSMISSION METHOD DURING IMAGING/AFTER IMAGING

IMAGING APPARATUS (B) — 17 × 17
- POWER 95%
- COMMUNICATION WIRED
- MEMORY CAPACITY 2.3G
- SIZE 1717
- RESOLUTION 100 / 200 μm
- CORRESPONDING IMAGING ONLY STILL IMAGE
- F RATE —
- TRANSMISSION METHOD DURING IMAGING/AFTER IMAGING

IMAGING APPARATUS (C) — 14 × 17
- POWER 95%
- COMMUNICATION WIRED
- MEMORY CAPACITY 2.3G
- SIZE 1717
- RESOLUTION 100 / 200 μm
- CORRESPONDING IMAGING DYNAMIC IMAGING IS AVAILABLE
- F RATE 20 / 10 / 5 Hz
- TRANSMISSION METHOD DURING IMAGING/AFTER IMAGING

RADIATION GENERATION APPARATUS (A) — 43a
- FOCUS SIZE 0.6 / 1.2 mm
- F RATE 15 / 10 / 5 Hz

DISPLAY WHETHER IMAGING IS AVAILABLE/STATUS
IMAGING IS AVAILABLE

CAPTURED IMAGE

SELECTION OF IMAGING

| CAPTURE OF STILL IMAGE | DYNAMIC IMAGING |
|---|---|
| STILL-IMAGE CAPTURE CONDITIONS | DYNAMIC IMAGING CONDITIONS |
| VOLTAGE 100kV | VOLTAGE 100kV |
| CURRENT 125mA | CURRENT 125mA |
| TIME 8ms | TIME 8ms |
| mAs VALUE 1.0mAs | mAs VALUE 1.0mAs |
| FOCUS SHORT 0.6 mm | FOCUS SHORT 0.6 mm |
| IMAGING TIME 20 SECONDS (300 IMAGES) | IMAGING TIME 20 SECONDS (300 IMAGES) |
| RESOLUTION 100/200μm | RESOLUTION 100/200μm |
| F RATE 15Hz | IMAGING F RATE 15Hz |
| | IRRADIATION F RATE 5 Hz |
| IMAGE TRANSMISSION WIRED | IMAGE TRANSMISSION WIRED |

FIG.10

ORDER LIST
- LUNG FIELD (STILL IMAGE)
- LUNG FIELD (DYNAMIC IMAGE)

IMAGING TABLE
- UPRIGHT IMAGING TABLE
- UPRIGHT IMAGING TABLE (ELONGATED)
- DECUBITUS IMAGING TABLE
- DECUBITUS IMAGING TABLE (ELONGATED)
- PANEL IMAGING

AVAILABLE PANEL — 43b

IMAGING APPARATUS (A): 14 × 17
- POWER 95%
- COMMUNICATION WIRED
- MEMORY CAPACITY 2.3G
- SIZE 1717
- RESOLUTION 100/200 μm
- CORRESPONDING IMAGING DYNAMIC IMAGING IS AVAILABLE
- F RATE 15/7.5/3.75 Hz
- TRANSMISSION METHOD DURING IMAGING/AFTER IMAGING

IMAGING APPARATUS (B): 17 × 17
- POWER 95%
- COMMUNICATION WIRED
- MEMORY CAPACITY 2.3G
- SIZE 1717
- RESOLUTION 100/200 μm
- CORRESPONDING IMAGING DYNAMIC IMAGING IS AVAILABLE
- F RATE 20/10/5 Hz
- TRANSMISSION METHOD ONLY STILL IMAGE DURING IMAGING/AFTER IMAGING 15/7.5 Hz

IMAGING APPARATUS (C): 14 × 17
- POWER 95%
- COMMUNICATION WIRED
- MEMORY CAPACITY 2.3G
- SIZE 1717
- RESOLUTION 100/200 μm
- CORRESPONDING IMAGING DYNAMIC IMAGING IS AVAILABLE
- F RATE 20/10/5 Hz
- TRANSMISSION METHOD DURING IMAGING/AFTER IMAGING

RADIATION GENERATION APPARATUS (A)
- FOCUS SIZE 0.6/1.2 mm
- F RATE 15/10/5 Hz

DISPLAY WHETHER IMAGING IS AVAILABLE/STATUS
IMAGING IS AVAILABLE

CAPTURED IMAGE

SELECTION OF IMAGING

CAPTURE OF STILL IMAGE
STILL IMAGE CAPTURE CONDITIONS
- VOLTAGE 100kV
- CURRENT 125mA
- TIME 8ms
- mAs VALUE 1.0mAs
- FOCUS SHORT 0.6 mm
- IMAGING TIME 20 SECONDS (300 IMAGES)
- RESOLUTION 100/200 μm
- F RATE 15Hz
- IMAGE TRANSMISSION WIRED

DYNAMIC IMAGING — 43c
DYNAMIC IMAGING CONDITIONS
- VOLTAGE 100kV
- CURRENT 125mA
- TIME 8ms
- mAs VALUE 1.0mAs
- FOCUS SHORT 0.6 mm
- IMAGING TIME 20 SECONDS (300 IMAGES)
- RESOLUTION 100/200 μm
- IMAGING F RATE 15Hz
- IRRADIATION F RATE 10 Hz (NOT AVAILABLE)
- IMAGE TRANSMISSION WIRED

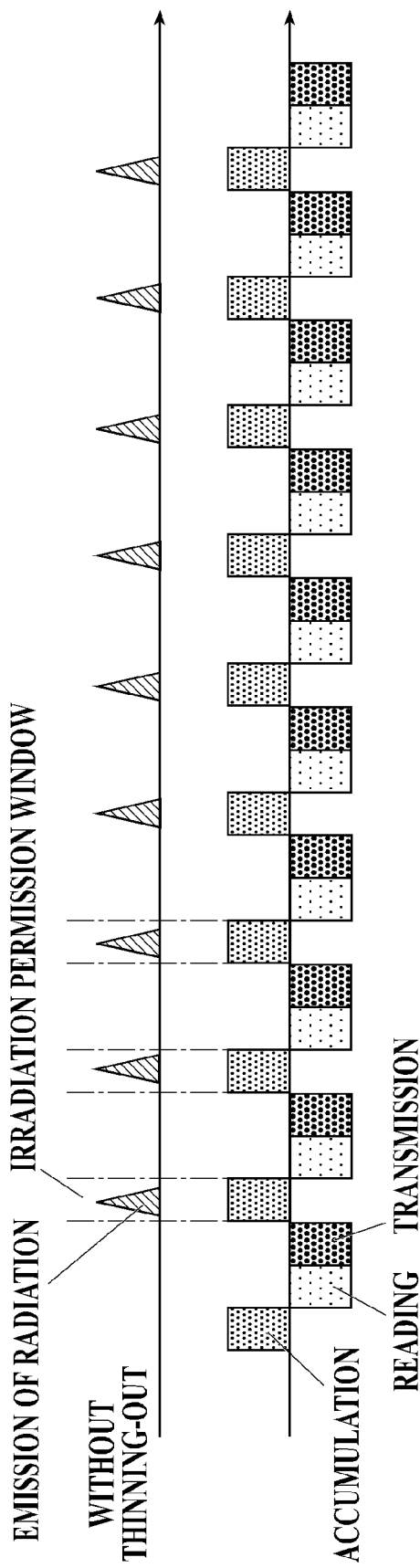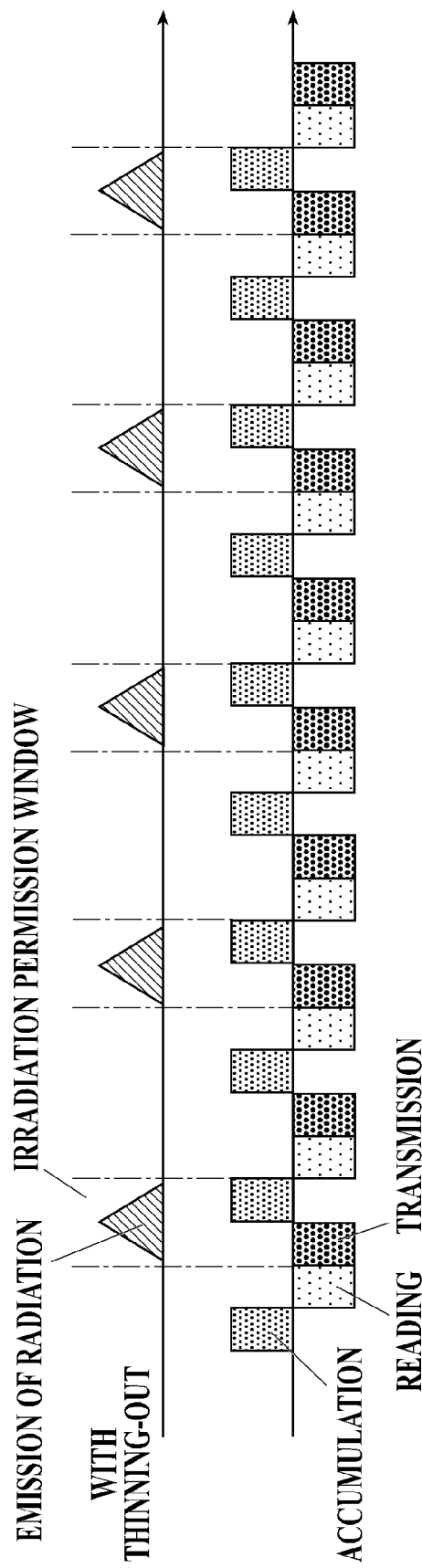

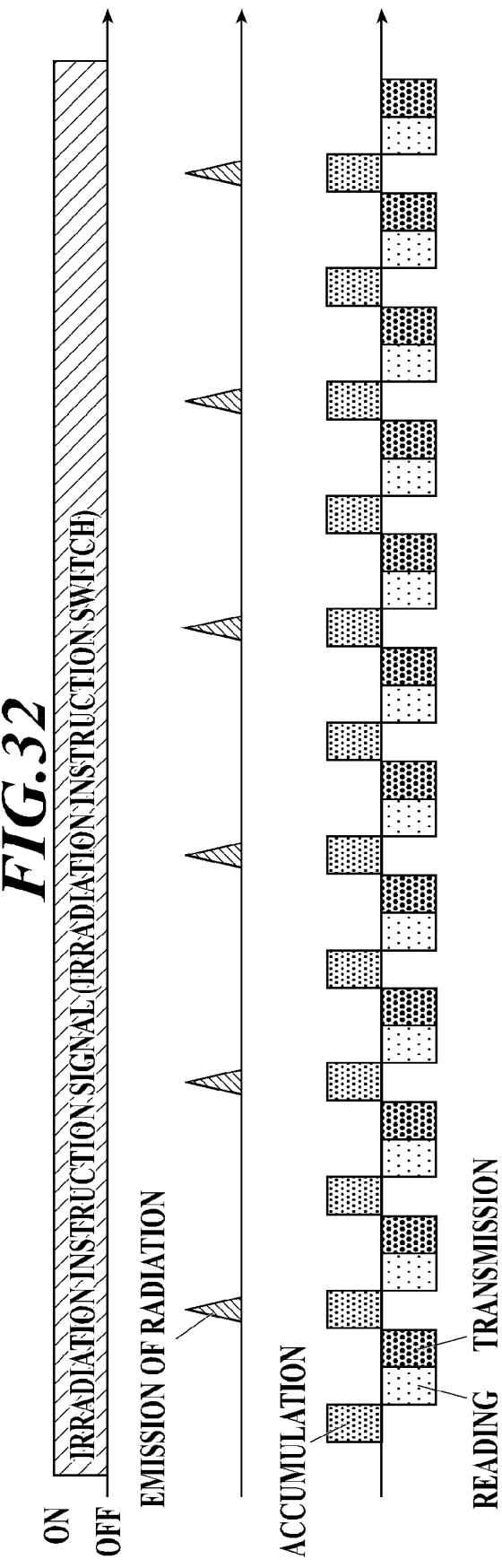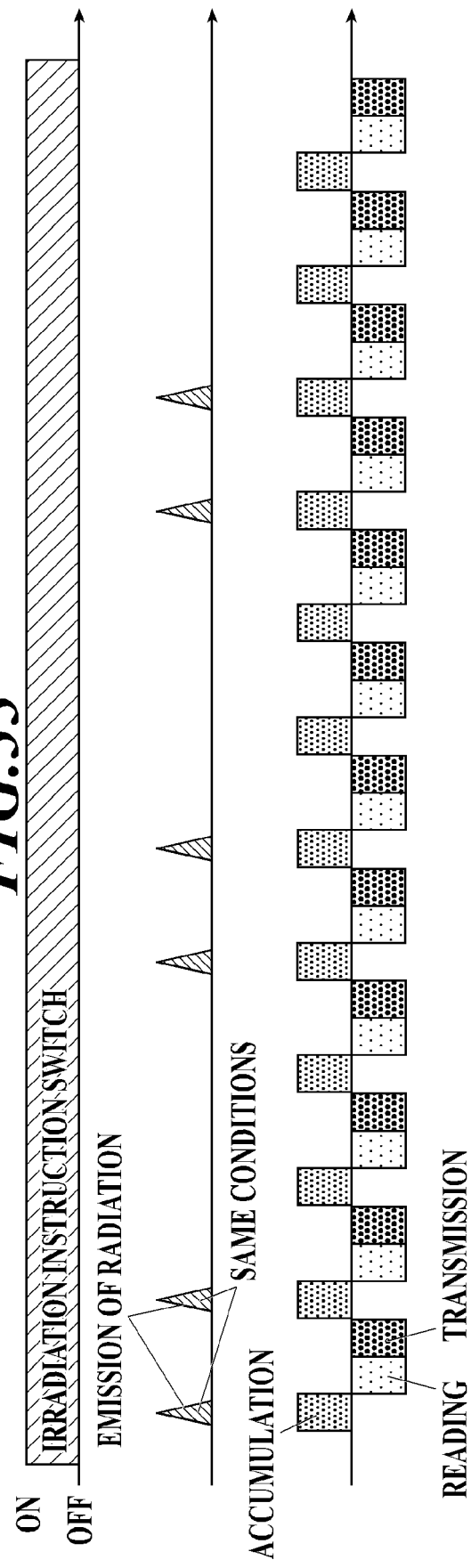

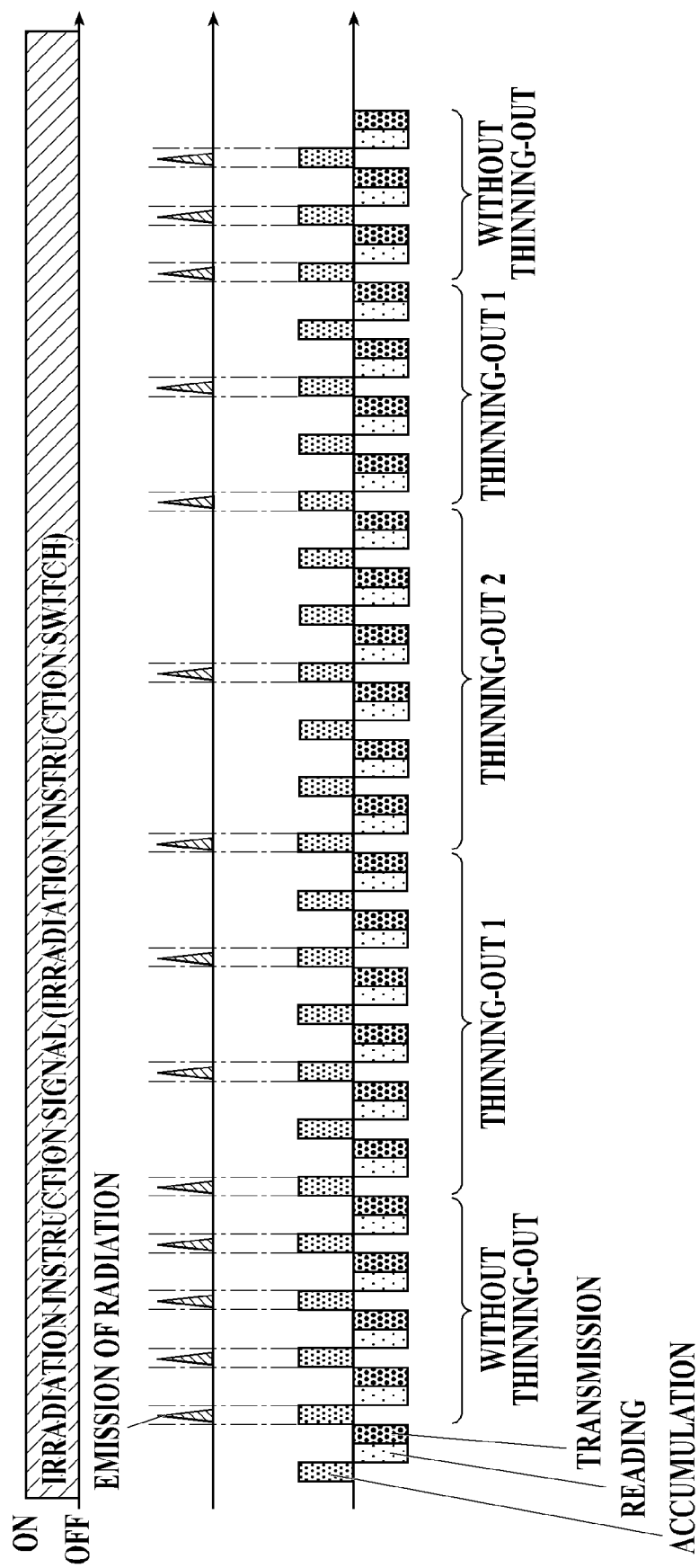

FIG.36

| FRAME NO. | WITHOUT THINNING-OUT | | WITH THINNING-OUT 1 | | WITH THINNING-OUT 2 | |
|---|---|---|---|---|---|---|
| | BEFORE PROCESS | AFTER PROCESS | BEFORE PROCESS | AFTER PROCESS | BEFORE PROCESS | AFTER PROCESS |
| 0 | 0 | 0.00 | 0 | 0.00 | 0 | 0.00 |
| 1 | 1 | 0.80 | 1 | 0.80 | 0 | 0.00 |
| 2 | 1 | 0.96 | 0 | 0.16 | 0 | 0.00 |
| 3 | 1 | 0.99 | 1 | 0.83 | 1 | 0.80 |
| 4 | 1 | 1.00 | 0 | 0.17 | 0 | 0.16 |
| 5 | 1 | 1.00 | 1 | 0.83 | 0 | 0.03 |
| 6 | 1 | 1.00 | 0 | 0.17 | 0 | 0.01 |
| 7 | 1 | 1.00 | 1 | 0.83 | 1 | 0.80 |
| 8 | 1 | 1.00 | 0 | 0.17 | 0 | 0.16 |
| 9 | 1 | 1.00 | 1 | 0.83 | 0 | 0.03 |
| 10 | 1 | 1.00 | 0 | 0.17 | 0 | 0.01 |
| 11 | 1 | 1.00 | 1 | 0.83 | 1 | 0.80 |
| 12 | 1 | 1.00 | 0 | 0.17 | 0 | 0.16 |
| 13 | 1 | 1.00 | 1 | 0.83 | 0 | 0.03 |
| 14 | 1 | 1.00 | 0 | 0.17 | 0 | 0.01 |
| 15 | 1 | 1.00 | 1 | 0.83 | 1 | 0.80 |
| 16 | 1 | 1.00 | 0 | 0.17 | 0 | 0.16 |
| 17 | 1 | 1.00 | 1 | 0.83 | 0 | 0.03 |
| 18 | 1 | 1.00 | 0 | 0.17 | 0 | 0.01 |
| 19 | 1 | 1.00 | 1 | 0.83 | 1 | 0.80 |
| 20 | 1 | 1.00 | 0 | 0.17 | 0 | 0.16 |
| 21 | 1 | 1.00 | 1 | 0.83 | 0 | 0.03 |
| 22 | 1 | 1.00 | 0 | 0.17 | 0 | 0.01 |
| 23 | 1 | 1.00 | 1 | 0.83 | 1 | 0.80 |
| 24 | 1 | 1.00 | 0 | 0.17 | 0 | 0.16 |
| 25 | 1 | 1.00 | 1 | 0.83 | 0 | 0.03 |
| 26 | 1 | 1.00 | 0 | 0.17 | 0 | 0.01 |
| 27 | 1 | 1.00 | 1 | 0.83 | 1 | 0.80 |
| 28 | 1 | 1.00 | 0 | 0.17 | 0 | 0.16 |
| 29 | 1 | 1.00 | 1 | 0.83 | 0 | 0.03 |
| 30 | 1 | 1.00 | 0 | 0.17 | 0 | 0.01 |
| 31 | 1 | 1.00 | 1 | 0.83 | 1 | 0.80 |
| 32 | 1 | 1.00 | 0 | 0.17 | 0 | 0.16 |
| 33 | 1 | 1.00 | 1 | 0.83 | 0 | 0.03 |
| 34 | 1 | 1.00 | 0 | 0.17 | 0 | 0.01 |
| 35 | 1 | 1.00 | 1 | 0.83 | 1 | 0.80 |
| 36 | 1 | 1.00 | 0 | 0.17 | 0 | 0.16 |
| 37 | 1 | 1.00 | 1 | 0.83 | 0 | 0.03 |
| 38 | 1 | 1.00 | 0 | 0.17 | 0 | 0.01 |
| 39 | 1 | 1.00 | 1 | 0.83 | 1 | 0.80 |
| 40 | 1 | 1.00 | 0 | 0.17 | 0 | 0.16 |
| 41 | 1 | 1.00 | 1 | 0.83 | 0 | 0.03 |
| 42 | 1 | 1.00 | 0 | 0.17 | 0 | 0.01 |
| 43 | 1 | 1.00 | 1 | 0.83 | 1 | 0.80 |
| 44 | 1 | 1.00 | 0 | 0.17 | 0 | 0.16 |
| 45 | 1 | 1.00 | 1 | 0.83 | 0 | 0.03 |
| 46 | 1 | 1.00 | 0 | 0.17 | 0 | 0.01 |
| 47 | 1 | 1.00 | 1 | 0.83 | 1 | 0.80 |
| 48 | 1 | 1.00 | 0 | 0.17 | 0 | 0.16 |
| 49 | 1 | 1.00 | 1 | 0.83 | 0 | 0.03 |
| 50 | 1 | 1.00 | 0 | 0.17 | 0 | 0.01 |
| 51 | 1 | 1.00 | 1 | 0.83 | 1 | 0.80 |

RADIATION GENERATION CONTROL DEVICE, RADIATION GENERATION CONTROL SYSTEM, AND RADIOGRAPHY SYSTEM

BACKGROUND

1. Technological Field

The present invention relates to a radiation generation control device, a radiation generation control system, and a radiography system.

2. Description of the Related Art

The fluoroscopic techniques according to the related art which capture the images of the inside of a subject using radiation are mainly divided into a technique that captures a low-quality moving image using a camera and a technique that captures a high-quality still image using a film or a fluorescent plate.

As a means for capturing a moving image, for example, there is an X-ray imaging apparatus as disclosed in JP H09-270955 A which includes a TV camera that generates an X-ray transmission image and an X-ray high voltage device which applies a pulsed high voltage synchronized with an image acquisition operation of the TV camera to an X-ray tube while an irradiation switch is pressed.

In the field of still image capture, a new radiography apparatus (flat panel detector) has been developed which includes a substrate in which a plurality of pixels are two-dimensionally arranged and reads, as image data, the amount of charge generated in each pixel according to the intensity of radiation emitted from a radiation generation apparatus through a subject to capture a still image.

For example, JP 5203467 B2 discloses a technique which enables the radiography apparatus to be used instead of a film or a fluorescent plate in the existing radiography system.

In recent years, a radiography apparatus has been proposed which has an imaging capability to further improve the performance of the radiography apparatus and to repeatedly capture still images a plurality of times in a short time. In addition, an attempt has been made which repeatedly emits pulsed radiation to the radiography apparatus with a predetermined period to capture a series of still images of the dynamics of the part to be examined in the subject and applies the captured images to diagnosis. Hereinafter, the imaging which repeatedly generates still images in a short time is referred to as dynamic imaging.

However, in the existing X-ray imaging system described in JP 5203467 B2, even in a case where the radiography apparatus can be replaced with an apparatus corresponding to the dynamic imaging, a radiation generation apparatus can perform only one radiation emission operation in response to one radiation emission instruction. Therefore, it is difficult to perform dynamic imaging.

SUMMARY

An object of the invention is to provide a technique that can easily modify the existing radiation generation apparatus capable of performing only one radiation emission operation in response to one radiation emission instruction so as to respond to dynamic imaging.

To achieve at least one of the abovementioned objects, according to an aspect of the present invention, a radiation generation control device includes:

an acquirer that acquires a first signal which instructs emission of radiation;

a first connector that inputs a second signal which indicates a driving state of a radiography apparatus that generates a radiographic image;

a second connector that connects with a radiation generation apparatus that generates radiation; and a controller that makes the second connector repeatedly output a third signal which instructs emission of radiation with a predetermined period based on the acquired first signal and the input second signal.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 3 is a block diagram illustrating a radiography apparatus included in a radiography system according to the first to fourth embodiments of the invention.

FIG. 4 is a block diagram illustrating a configuration example in which the radiography system according to the first to fourth embodiments includes a plurality of constituent apparatuses.

FIG. 5 is a ladder chart illustrating the first half of the operation of the radiography system according to the first embodiment.

FIG. 6 is a ladder chart illustrating the second half of the operation of the radiography system according to the first embodiment.

FIG. 7 is a timing chart illustrating the operation of the radiography system according to the first embodiment.

FIG. 8 is a table illustrating the correspondence between radiography apparatuses and radiation generation apparatuses that can be connected to the radiography system according to the second embodiment and frame rates corresponding to these apparatuses.

FIG. 9 illustrates an example of a display screen of a display of a console included in the radiography system according to the second embodiment.

FIG. 10 illustrates an example of a display screen of the display of the console included in the radiography system according to the second embodiment.

FIG. 11 illustrates an example of a display screen of the display of the console included in the radiography system according to the second embodiment.

FIGS. 29A and 29B are timing charts illustrating the operation of a radiography system according to an example of the first to fourth embodiments.

FIG. 32 is a timing chart illustrating the operation of a radiography system according to an example of the first to fourth embodiments.

FIG. 33 is a timing chart illustrating the operation of a radiography system according to an example of the first to fourth embodiments.

FIG. 34 is a timing chart illustrating the operation of a radiography system according to an example of the first to fourth embodiments.

FIG. 36 is a table illustrating a steady-state value after a recursive filtering process is performed for a dynamic image captured by a radiography system according to an example of the first to fourth embodiments.

DETAILED DESCRIPTION OF EMBODIMENTS

Hereinafter, one or more embodiments of the present invention will be described with reference to the drawings. However, the scope of the invention is not limited to the disclosed embodiments.

Conventional Technology 1 which is the basis of first and second embodiments, the first embodiment, and the second embodiment will be described in this order. Then, Conventional Technology 2 which is the basis of third and fourth embodiments, the third embodiment, and the fourth embodiment will be described in this order.

Conventional Technology 1

First, Conventional Technology 1 which is the basis of a system 100 (will be described in detail below) according to the first embodiment of the invention will be described with reference to FIG. 1.

System Configuration

First, the schematic configuration of a radiography system (hereinafter, referred to as a conventional system 100A) according to Conventional Technology 1 will be described. FIG. 1 is a block diagram illustrating the conventional system 100A.

Figure 1:
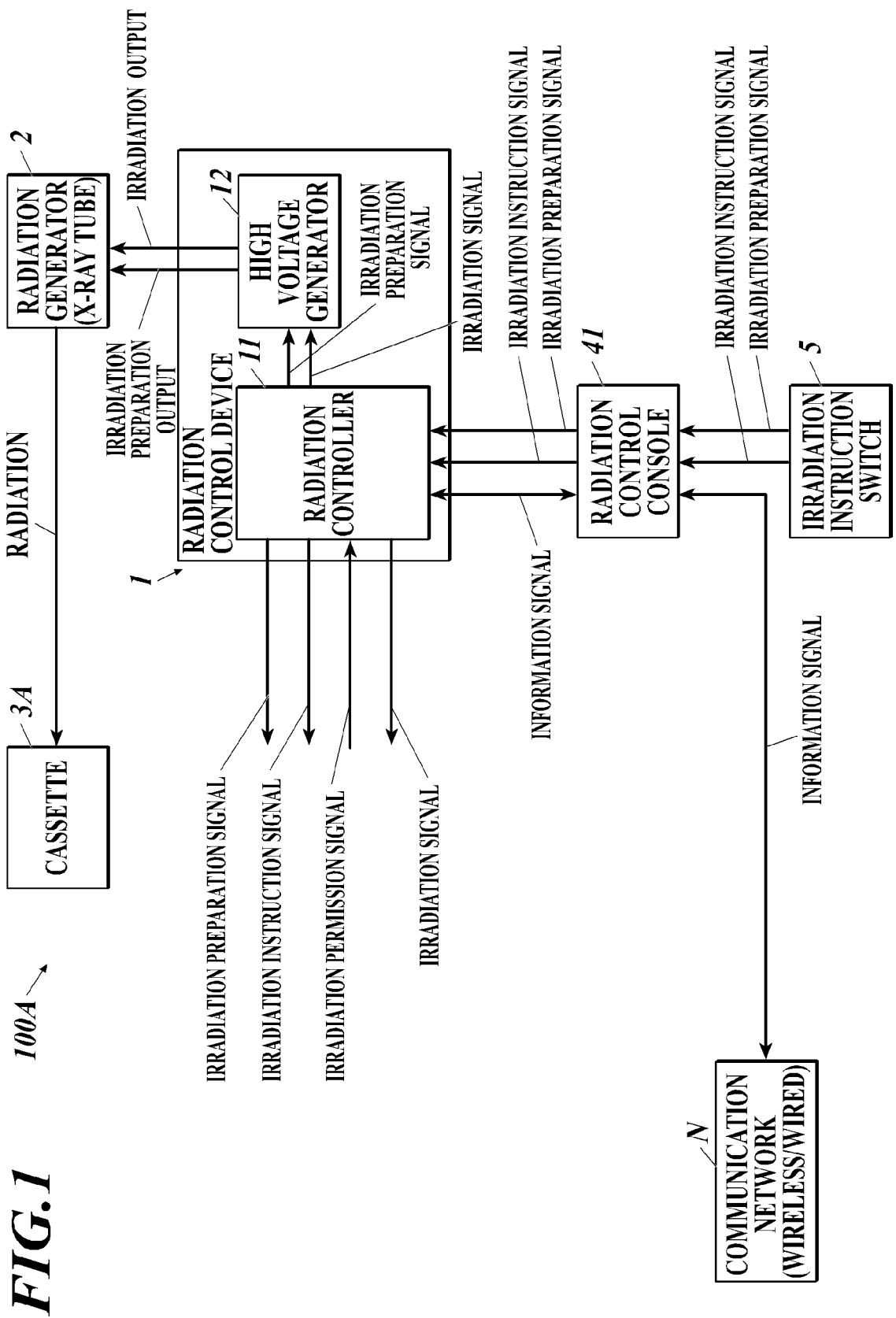
FIG. 1 is a block diagram illustrating a radiography system according to Conventional Technology 1.

As illustrated in FIG. 1, the conventional system 100A includes, for example, a radiation controller 11, a high voltage generator 12, a radiation generator 2, a cassette 3A, a radiation control console 41, and an irradiation instruction switch 5 and is configured to capture still images in which the radiation emission timing is not operatively associated with the imaging timing, using a radiographic film or CR.

FIG. 1 illustrates a case where the radiation controller 11 and the high voltage generator 12 form a radiation control device 1 (for example, are accommodated in one housing). However, the radiation controller 11 and the high voltage generator 12 may be separately provided. For example, the radiation controller 11 and the high voltage generator 12 may be provided in different housings.

The radiation controller 11, the high voltage generator 12, and the radiation generator 2 form a radiation generation apparatus (hereinafter, referred to as a generation apparatus) according to the invention.

The radiation controller 11 is for controlling the emission of radiation.

Specifically, the radiation controller 11 can turn on an irradiation preparation signal to be output to the high voltage generator 12 or can control the irradiation preparation signal such that the irradiation preparation signal can be output to other external apparatuses, on the basis of the detection of the turn-on of the irradiation preparation signal from the radiation control console 41.

In addition, the radiation controller 11 can control an irradiation instruction signal (first signal) for instructing the emission of radiation such that the irradiation instruction signal can be output to an external apparatus, on the basis of the detection of the turn-on of the irradiation instruction signal from the radiation control console 41, and can transmit an irradiation signal corresponding to imaging conditions set by the radiation control console 41 to the high voltage generator 12.

The irradiation preparation signal or the irradiation instruction signal that can be transmitted from the radiation controller 11 to an external apparatus is used, for example, in a case where the external apparatus is connected to the radiation controller 11.

The irradiation preparation signal or the irradiation instruction signal enables the external apparatus to prepare imaging on the basis of the irradiation preparation signal or the irradiation instruction signal output from the radiation controller 11 in imaging in which the external apparatus other than the cassette 3A is required at the time of the emission of radiation.

An example of the external apparatus is a grid rocking apparatus that is provided on a radiation incident surface of the cassette 3A and is used to rock the grid in a case where imaging is performed.

Some of the external apparatuses have a configuration in which an irradiation permission signal is transmitted to the radiation controller 11 after preparation for imaging is completed. Therefore, the radiation controller 11 may include a connector for receiving the irradiation permission signal from the external apparatus and may transmit the irradiation signal to the high voltage generator 12 only in a case where both the irradiation instruction signal from the radiation control console 41 and the irradiation permission signal from the external apparatus are turned on.

In this case, the irradiation permission signal is not input to the radiation controller 11 before the imaging preparation of the external apparatus is completed. Therefore, it is possible to prevent radiation from being emitted before the imaging preparation of the external apparatus is completed.

For example, in a case where the external apparatus is the above-mentioned grid rocking apparatus, after the grid rocking apparatus starts rocking and reaches a designated rocking speed, the grid rocking apparatus may input the irradiation permission signal to the radiation controller 11. In this configuration, in a case where the radiation controller 11 receives both the irradiation instruction signal from an irradiation instruction switch 5 based on an operation of a radiographer and the irradiation permission signal from the external apparatus, the radiation controller 11 outputs the irradiation signal first. Therefore, it is possible to prevent radiation from being emitted before the preparation of the external apparatus is completed.

In contrast, in a case where the radiation controller 11 does not want to use the irradiation permission signal from the external apparatus, for example, it is necessary to invalidate the irradiation permission signal or to keep the irradiation permission signal in an on or off state.

For example, in a case where the radiation controller 11 is configured to switch whether to use the irradiation permission signal from the external apparatus for determining whether or not the irradiation signal can be output, the switching may be invalidated such that the irradiation permission signal is not used for the determination.

In a case where the switching is not capable of being performed and, for example, the irradiation permission signal is configured to be instructed by opening or closing two signal lines, the two signal lines are always opened or closed to keep the irradiation permission signal in an on or off state.

Further, the radiation controller 11 may be configured not to transmit the irradiation signal until a predetermined standby time elapses after the detection of the turn-on of the irradiation preparation signal even if the turn-on of the irradiation instruction signal has been detected.

In this configuration, even in a case where the high voltage generator 12 or the radiation generator is configured to require some time for preparation after the turn-on of the irradiation preparation signal is detected, it is possible to prevent radiation from being emitted even through preparation for irradiation is not completed.

The high voltage generator 12 is configured to output an irradiation preparation output to the radiation generator 2 on the basis of the detection of the turn-on of the irradiation preparation signal from the radiation controller 11.

In addition, the high voltage generator 12 is configured to apply, as an irradiation output, a high voltage (corresponding to the input irradiation signal) required for the radiation generator 2 to generate radiation to the radiation generator 2, on the basis of the reception of the irradiation signal from the radiation controller 11.

FIG. 1 illustrates the configuration in which, when the high voltage generator 12 detects that the irradiation preparation signal from the radiation controller 11 has been turned on, the high voltage generator 12 transmits the irradiation preparation output to the radiation generator 2. However, the invention is not limited thereto. For example, the radiation controller 11 may directly output the irradiation preparation signal to the radiation generator 2 and the radiation generator 2 may convert the irradiation preparation signal into the irradiation preparation output and prepare irradiation.

The radiation generator 2 (radiation tube) includes, for example, an electron gun and an anode and is configured to generate radiation (for example, X-rays) corresponding to the high voltage applied from the high voltage generator 12.

Specifically, when the high voltage is applied, the electron gun emits electron beams to the anode and the anode receives the electron beams and generates radiation.

When radiation is generated, a portion that receives the electron beams generates heat and reaches a high temperature. Therefore, it is necessary to constantly change the position of the anode where the electron beams are emitted in order to stably emit the radiation. For this reason, in some cases, a rotating anode that emits electron beams while being rotated can be used.

The irradiation preparation output from the high voltage generator 12 can be used, for example, as a rotation start instruction of the rotating anode.

The cassette 3A has a radiation film or a fluorescent plate provided therein and can form a radiographic image of a subject when radiation transmitted through the subject is incident.

The radiation control console 41 is configured to set information related to the subject or imaging conditions (for example, a tube voltage, a tube current, and an irradiation time) in the radiation controller 11, using the connection of an information signal.

Figure 17:
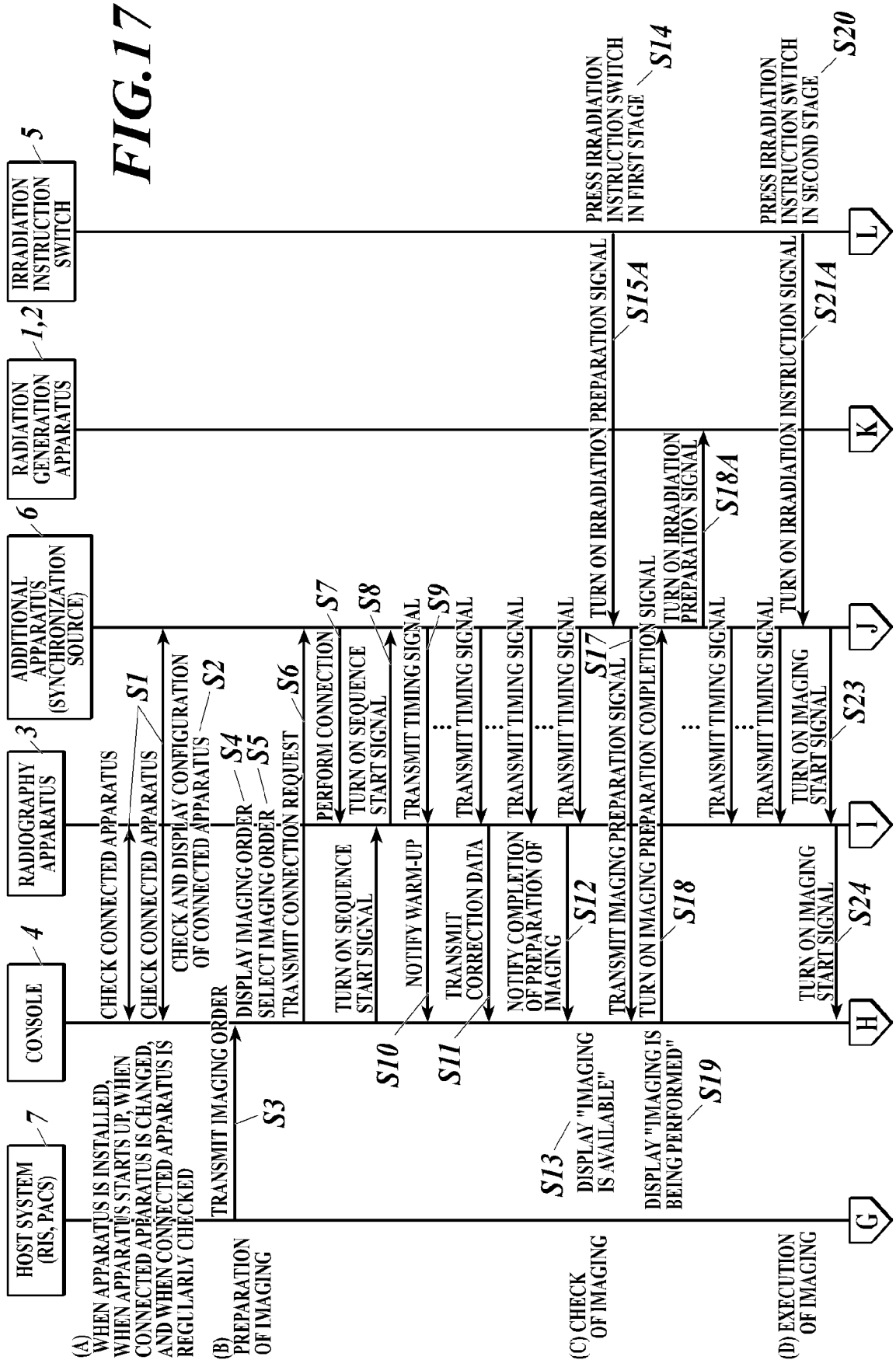
FIG. 17 is a ladder chart illustrating the first half of the operation of the radiography system according to the third embodiment.

In addition, the radiation control console 41 may communicate with a host system 7 (for example, a radiology information system (RIS)) or a picture archiving and communication system (PACS); see FIGS. 5 and 17) through the external communication network N such as a hospital LAN.

The irradiation instruction switch 5 is used by the radiographer to instruct the emission of radiation.

The irradiation instruction switch 5 according to this embodiment is configured to operate in two stages. Specifically, the irradiation instruction switch 5 is pressed to the first stage to turn on the irradiation preparation signal output to the radiation control console 41 and the irradiation instruction switch 5 is pressed to the second stage to turn on the irradiation instruction signal output to the radiation control console 41.

FIG. 1 illustrates the configuration in which the irradiation instruction switch 5 is connected to the radiation control console 41, the irradiation preparation signal or the irradiation instruction output from the signal irradiation instruction switch 5 is input to the radiation controller 11 through the radiation control console 41. However, the invention is not limited thereto. The irradiation instruction switch 5 may be connected to the radiation controller 11 such that the irradiation preparation signal or the irradiation instruction signal is directly input to the radiation controller 11.

Operation

The operation of the conventional system 100A will be described.

Irradiation Preparation Operation

If the radiographer presses the irradiation instruction switch 5 to the first stage, the irradiation instruction switch 5 turns on the irradiation preparation signal output to the radiation controller 11 through the radiation control console 41.

If it is detected that the irradiation preparation signal has been turned on, the radiation controller 11 turns on the irradiation preparation signal output to the high voltage generator 12 and performs control such that the irradiation preparation signal can be output to the external apparatus.

If the high voltage generator 12 detects that the irradiation preparation signal has been turned on, it outputs the irradiation preparation output to the radiation generator 2.

If the irradiation preparation output is input, the radiation generator 2 starts preparation for generating radiation.

The preparation for generating radiation indicates, for example, an operation of rotating a rotating anode in a case where the anode is the rotating anode.

Irradiation Operation

Then, if the radiographer presses the irradiation instruction switch to the second stage, the irradiation instruction switch 5 turns on the irradiation instruction signal output to the radiation controller 11 through the radiation control console 41.

If it is detected that the irradiation instruction signal has been turned on, the radiation controller 11 performs control such that the irradiation instruction signal can be output to the external apparatus and transmits the irradiation signal to the high voltage generator 12.

In addition, the radiation controller 11 transmits the irradiation signal to the high voltage generator 12 in the following case: the radiation controller 11 is configured to determine whether to emit radiation on the basis of the irradiation permission signal from the external apparatus; the irradiation instruction signal from the irradiation instruction switch 5 or the radiation control console 41 is in an on state; and the irradiation permission signal is received from the external apparatus.

If the irradiation signal is received, the high voltage generator 12 applies the high voltage required for the radiation generator 2 to emit radiation to the radiation generator 2 (performs irradiation output).

If the high voltage is applied from the high voltage generator 12, the radiation generator 2 generates radiation corresponding to the applied voltage.

For example, the irradiation direction, irradiation region, and quality of the generated radiation are adjusted by a controller (not illustrated), such as a collimator, and the adjusted radiation is emitted to the subject and the cassette 3A behind the subject. A portion of the radiation passes through the subject and is then incident on the cassette 3A.

If the radiation is incident on the cassette 3A, a radiographic image is formed on the film or the fluorescent plate provided in the cassette 3A.

In a case where the timing when the irradiation preparation signal is turned on and the timing when the irradiation instruction signal are close to each other, for example, irradiation is performed before the rotation of the rotating anode of the radiation generator 2 reaches a sufficient speed and a local part of the rotating anode is excessively heated. As a result, the rotating anode is likely to be damaged or the amount of radiation emitted is likely to be unstable (for example, the amount of radiation is insufficient or excessive with respect to the irradiation intensity of the electron beams).

However, the above-mentioned configuration in which the radiation controller 11 does not to transmit the irradiation signal until a predetermined standby time elapses from the detection of the turn-on of the irradiation preparation signal even if the turn-on of the irradiation instruction signal has been detected makes it possible to prevent the occurrence of the above-mentioned problem.

As such, in radiography using the conventional system 100A, only one radiographic image (still image) of the subject is captured on the basis of one imaging operation.

First Embodiment

A first embodiment of the invention will be described with reference to FIGS. 2 to 7. The same configurations as those in Conventional Technology 1 are denoted by the same reference numerals and the description thereof will not be repeated.

System Configuration

Figure 2:
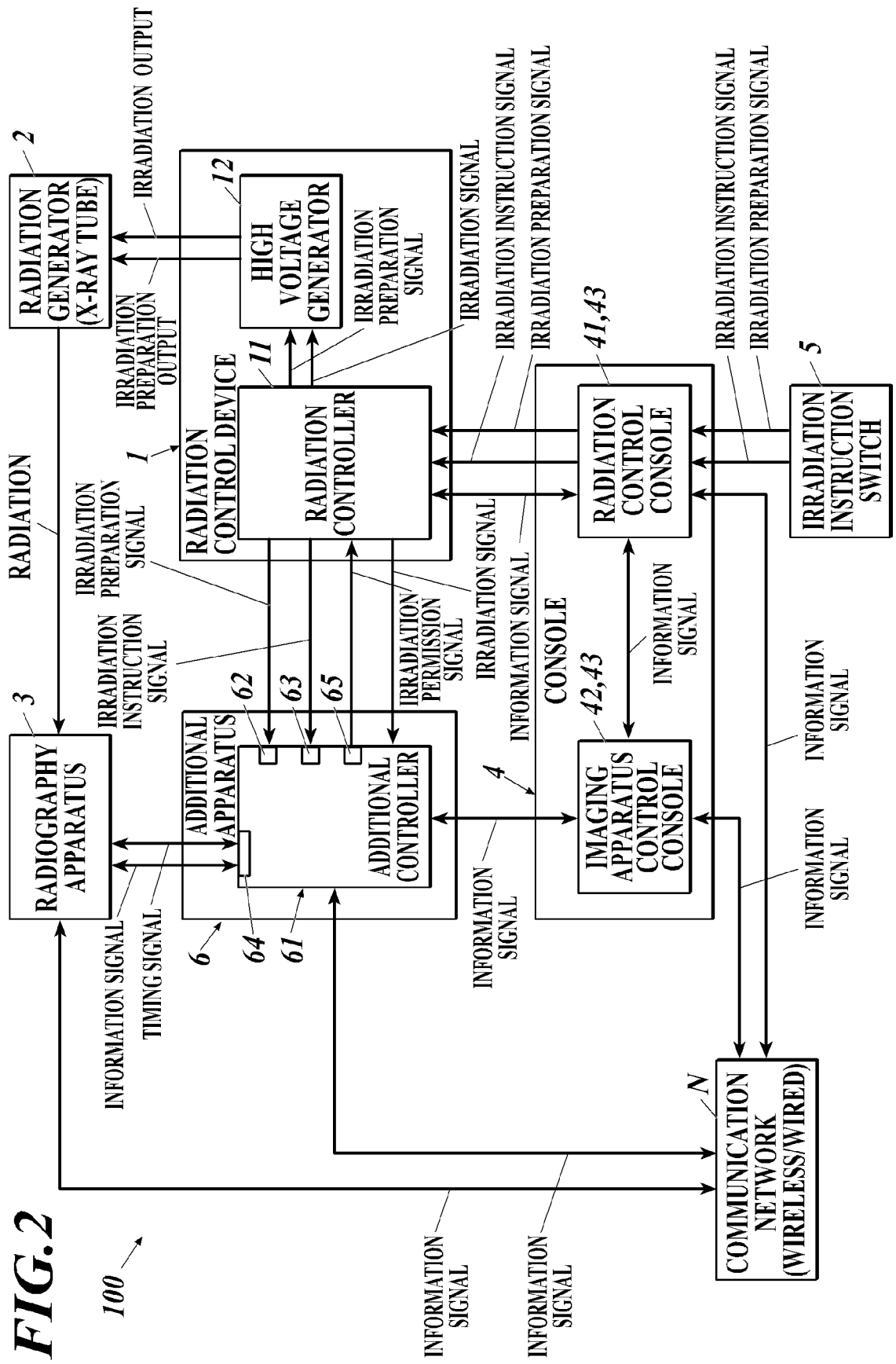
FIG. 2 is a block diagram illustrating a radiography system according to first and second embodiments of the invention.

First, a system configuration of a radiography system (hereinafter, referred to as a system 100) according to this embodiment will be described. FIG. 2 is a block diagram illustrating the system 100 and FIG. 3 is a block diagram illustrating a radiography apparatus 3.

For example, the system 100 according to this embodiment differs from the conventional system 100A in that the radiography apparatus (hereinafter, referred to as the imaging apparatus 3) replaces the cassette 3A and an imaging apparatus control console 42 and an additional apparatus 6 are added, as illustrated in FIG. 2.

The imaging apparatus 3 according to this embodiment includes, for example, an imaging controller 31, a radiation detector 32, a scanning driver 33, a reader 34, a storage 35, and a communicator 36, in addition to a housing (not illustrated) and a scintillator (not illustrated), as illustrated in FIG. 3. The components 31 to 36 are supplied with power from a battery 37.

The housing is provided with, for example, a power switch (not illustrated), a changeover switch (not illustrated), an indicator (not illustrated), a connector 36b of the communicator 36 which will be described below.

When the scintillator receives radiation, it emits electromagnetic waves having a longer wavelength than radiation, such as visible light.

The imaging controller 31 is, for example, a computer in which a central processing unit (CPU), a read only memory (ROM), a random access memory (RAM), and an input/output interface are connected to a bus or a field programmable gate array (FPGA) which is not illustrated. In addition, the imaging controller 31 may be a dedicated control circuit.

The radiation detector 32 receives radiation and generates charge. The radiation detector 32 includes, for example, a substrate 32a, a plurality of scanning lines 32b, a plurality of signal lines 32c, a plurality of radiation detection elements 32d, a plurality of switching elements 32e, a plurality of bias lines 32f, and a power supply circuit 32g.

The substrate 32a is formed in a plate shape and is disposed so as to face the scintillator in parallel.

The plurality of scanning lines 32b are provided so as to extend in parallel at predetermined intervals.

The plurality of signal lines 32c are provided such that they extend in parallel at predetermined intervals, extend in a direction perpendicular to the scanning line 32b, and are not electrically connected to the scanning lines.

That is, the plurality of scanning lines 32b and the signal lines 32c are provided so as to form a lattice.

Each of the radiation detection elements 32d generates an electric signal (current or charge) corresponding to the amount of radiation emitted to the radiation detection element (or the amount of light of electromagnetic waves converted by the scintillator) and is, for example, a photodiode or a phototransistor.

The plurality of radiation detection elements 32d are provided in a plurality of regions partitioned by the plurality of scanning lines 32b and the plurality of signal lines 32c on a surface of the substrate 32a. That is, the plurality of radiation detection elements 32d are arranged in a matrix. Therefore, each radiation detection element 32d faces the scintillator.

A drain terminal of the switching element 32e which is a switching element is connected to one terminal of each radiation detection element 32d and the bias line is connected to the other terminal of the switching element 32e.

The plurality of switching elements 32e are provided in a plurality of regions partitioned by the plurality of scanning lines 32b and the plurality of signal lines 32c, similarly to the radiation detection elements 32d.

Each switching element 32e has a gate electrode that is connected to the neighboring scanning line 32b, a source electrode that is connected to the neighboring signal line 32c, and a drain electrode that is connected to one terminal of the radiation detection element 32d in the same region.

The plurality of bias lines 32f are connected to the other terminal of each radiation detection element 32d.

The power supply circuit 32g generates a reverse bias voltage and applies the reverse bias voltage to each radiation detection element through the bias lines 32f.

The scanning driver 33 includes, for example, a power supply circuit 33a and a gate driver 33b.

The power supply circuit 33a generates an on-voltage and an off-voltage which are different from each other and supplies the generated voltages to the gate driver 33b.

The gate driver 33b switches the voltage applied to each scanning line 32b to the on-voltage or the off-voltage.

The reader 34 includes, for example, a plurality of reading circuits 34a, an analog multiplexer 34b, and an A/D converter 34c.

The plurality of reading circuits 34a are connected to each signal line 32c of the radiation detector 32 and apply a reference voltage to each signal line 32c.

Each reading circuit 34a includes, for example, an integration circuit 34d and a correlated double sampling circuit (hereinafter, referred to as a CDS circuit) 34e.

The integration circuit 34d integrates the charge transmitted to the signal line 32c and outputs a voltage value corresponding to the integrated amount of charge to the CDS circuit 34e.

The CDS circuit 34e samples and holds the output voltage of the integration circuit 34d before the on-voltage is applied to the scanning line 32b to which the radiation detection element 32d, from which a signal is to be read, is connected (while the off-voltage is applied). After the on-voltage is applied to the scanning line 32b to read signal charge from the radiation detection element and the off voltage is applied to the scanning line 32b, the CDS circuit 34e outputs the difference between the output voltages of the integration circuit 34d.

The analog multiplexer 34b outputs a plurality of difference signals output from the CDS circuits 34e one by one to the A/D converter 34c.

The A/D converter 34c sequentially converts image data of the input analog voltage value into image data of a digital value.

The storage 35 is, for example, a static RAM (SRAM), a synchronous DRAM (SDRAM), a NAND flash memory, or a hard disk drive (HDD).

The communicator 36 includes an antenna 36a for communication with the outside and the connector 36b.

The communicator 36 can select one of wireless communication and wired communication on the basis of a control signal from the outside. That is, in a case where wireless communication is selected, the communicator 36 can perform wireless communication using the antenna 36a. In a case where wired communication is selected, the communicator 36 can transmit and receive information using, for example, a wired LAN. In addition, in a case where the user wants to perform synchronization using wired communication, for example, it is possible to perform synchronization using a protocol, such as the Network Time Protocol (NTP), or a method defined by the international standard IEEE1588.

If power is turned on, the imaging apparatus 3 having the above-mentioned configuration is switched to one of an "initialization state", an "accumulation state", and a "reading and transmission state". The timing when the state is switched will be described below.

In the "initialization state", the on-voltage is applied to each switching element 32e and the charge generated by the radiation detection element 32d is not accumulated in each pixel (the charge is output to the signal line 32c).

In the "accumulation state", the off-voltage is applied to each switching element 32e and the charge generated by the radiation detection element 32d can be accumulated in the pixel (the charge is not transmitted to the signal line 32c).

In the "reading and transmission state", the on-voltage is applied to each switching element 32e, the reader 34 is driven to read image data based on the transmitted charge and can transmit the image data to other devices.

The accumulated charge is cleared by reading, depending on the configuration of the elements and the devices. Therefore, "reading" and "initialization" are not distinguished as separate operations and may be performed as the same operations at the same time.

In this embodiment, a so-called indirect type that converts the emitted radiation into electromagnetic waves with other wavelengths, such as visible light, to obtain an electric signal has been described as an example. However, the invention is not limited thereto. A so-called direct-type imaging apparatus may be used in which a detection element directly converts radiation into an electric signal.

In addition, other configurations of the imaging apparatus 3 do not need to be limited to those illustrated in FIG. 3 as long as they can generate the image data of the radiographic image.

As illustrated in FIG. 2, the imaging apparatus control console 42 is configured to transmit and receive an information signal to and from a radiation control console 41 and to set, for example, information related to the subject or imaging conditions in the imaging apparatus 3.

The radiation control console 41 performs setting for the radiation controller 11 and the imaging apparatus control console 42 performs setting for the imaging apparatus 3. However, since both the radiation control console 41 and the imaging apparatus control console 42 perform setting related to the same imaging operation, they may be collectively referred to as a console 4 in a broad sense in the following description.

The console 4 and the additional apparatus 6 form a radiation generation control system according to the invention.

In addition, FIG. 2 illustrates the configuration in which the imaging apparatus control console 42 sets, for example, imaging conditions in a radiation controller 11 through the radiation control console 41 (the radiation control console 41 and the imaging apparatus control console 42 transmit and receive information signals). However, the imaging apparatus control console 42 may directly perform setting for the radiation controller 11.

Further, the radiation control console 41 may perform setting for the imaging apparatus 3.

FIG. 2 illustrates the configuration in which the console 4 is connected to the imaging apparatus 3 through the additional apparatus 6. However, for example, the console 4 may be directly connected to the imaging apparatus 3 or may be connected to the imaging apparatus 3 through a communication network N as illustrated in FIG. 2.

Further, the console 4 may set the operation of the additional apparatus 6.

Specifically, it is possible to set, in the additional apparatus 6, the number of times the irradiation permission signal (a third signal in the invention) is output (maximum number of images captured) or the output time for which the output of the irradiation permission signal is repeated set in the additional apparatus 6 until the additional apparatus 6 outputs the irradiation permission signal.

The console 4 may include a display 43 and the number of outputs or the output time set in the additional apparatus 6 may be displayed on the display 43.

In addition, when an imaging start signal (a second signal according to the invention which will be described in detail below) input to the additional apparatus 6 is turned on, the console 4 may display information indicating that irradiation is possible on the display 43.

Further, while the additional apparatus 6 is being output the irradiation permission signal, the console 4 may display information indicating that radiation is being emitted on the display 43.

The additional apparatus 6 is a radiation generation control device according to the invention and includes an additional controller 61 having a first acquirer 62, a second acquirer 63, a first connector 64, and a second connector 65.

The additional controller 61 includes, for example, a CPU and a RAM and is configured to control the overall operation of each component of the additional apparatus 6.

In this case, the additional controller 61 reads various processing programs stored in a storage (not illustrated), expands the programs in the RAM, and performs various processes according to the processing programs.

The first acquirer 62 forms a contact (for example, a connector) with the radiation controller 11 and acquires the irradiation preparation signal output from an irradiation instruction switch 5 through the radiation controller 11 (radiation generation apparatus) in this embodiment.

The second acquirer 63 forms a contact (for example, a connector) with the radiation controller 11 and acquires the irradiation instruction signal output from the irradiation instruction switch 5 through the radiation controller 11 (radiation generation apparatus) in this embodiment.

Since the irradiation instruction signal corresponds to the first signal according to the invention as described above, the second acquirer 63 forms an acquirer according to the invention.

The first connector 64 forms a contact (for example, a connector) with the imaging apparatus 3 and is configured to input the irradiation start signal.

The irradiation start signal is turned on when the imaging apparatus 3 is in a state in which it can capture images and is turned off when the imaging apparatus 3 is in a state in which it is not capable of capturing images. Therefore, the irradiation start signal is a signal indicating the driving state of the imaging apparatus 3 in the invention.

The second connector 65 is a connector in this embodiment and is connected to the radiation controller 11 (radiation generation apparatus) by inserting the other end of a cable whose one end is connected to radiation controller 11 (radiation generation apparatus) into the second connector 65.

Therefore, the irradiation permission signal can be output to the radiation controller 11.

FIG. 2 illustrates the configuration in which the first acquirer 62, the second acquirer 63, the first connector 64, and the second connector 65 directly transmit and receive information or signals to and from other apparatuses (the first and second acquirers 63 and the second connector 65 directly transmit and receive information or signals to and from the radiation control device 1 and the first connector 64 directly transmits and receives information or signals to and from the imaging apparatus 3). However, at least one of the first acquirer 62, the second acquirer 63, the first connector 64, and the second connector 65 may be connected to other apparatuses through a relay (not illustrated) that can relay signals.

Further, FIG. 2 illustrates a case where the first acquirer 62, the second acquirer 63, the first connector 64, and the second connector 65 are separately provided. However, at least two of the first acquirer 62, the second acquirer 63, the first connector 64, and the second connector 65 may be integrated (the components 62 to 65 may be shared).

The additional controller 61 of the additional apparatus 6 having the above-mentioned configuration can repeatedly output a pulsed irradiation permission signal for instructing the emission of radiation with a predetermined period from the second connector 65 to the radiation controller 11, on the basis of the irradiation instruction signal acquired from the radiation controller 11 through the second acquirer 63 and the irradiation start signal input from the imaging apparatus 3 through the first connector 64.

The additional controller 61 may not output the irradiation permission signal until a predetermined standby time elapses from the detection of the turn-on of the irradiation start signal even if the turn-on of the imaging start signal has been turned on.

The additional controller 61 outputs a timing signal (a fourth signal in the invention) indicating the imaging timing of a radiographic image from the first connector 64 to the imaging apparatus 3 on the basis of the output timing of the irradiation permission signal.

The imaging timing is, for example, the timing when an operation of accumulating charge of a radiographic image starts. That is, the imaging apparatus 3 according to this embodiment performs an operation which starts to accumulate charge according to the timing signal, sequentially ends the accumulation using a timer of the imaging apparatus 3, reads out the charge of each pixel, changes the charge of each pixel to an image, and stores or transmits the image.

This control enables the additional controller 61 to control both the radiation emission timing based on the irradiation permission signal and the accumulation timing when charge is accumulated in the emission of radiation based on the timing signal. As a result, it is possible to reliably accumulate charge obtained by the emission of radiation and to reliably acquire an image obtained by the emission of radiation.

In a case where the time when the charge accumulation operation starts is set as the imaging timing as described above, the imaging apparatus 3 may stand by in a state in which it can shift to the accumulation timing corresponding to the imaging operation by the emission of radiation and may start the accumulation operation according to the timing signal.

This control enables the additional controller 61 to reliably acquire the image obtained by the emission of radiation as in the above-mentioned case.

The imaging timing triggered by the input of the timing signal may be the timing when any one of various operations repeatedly performed by the imaging device 3 starts in addition to the charge accumulation operation.

For example, in a case where it is necessary to reset the charge accumulated in each pixel before the accumulation operation, the timing when the reset starts may be the imaging timing.

In this case, the imaging apparatus 3 may be sequentially shifted to the accumulation operation after the reset is completed.

This control enables the imaging apparatus to shift to the accumulation operation that accumulates charge obtained by the emission of radiation in a state in which dark charge, which is a noise component accumulated in each pixel over time before charge is accumulated by the emission of radiation, is output by the reset operation. Therefore, it is possible to acquire an image with less noise.

Alternatively, the timing when the accumulate operation is ended may be the imaging timing. Alternatively, the timing when the reading of the charge accumulated by the timing signal starts may be the imaging timing.

This control enables the additional controller 61 to control both the radiation emission timing based on the irradiation permission signal and the timing when the accumulation of charge by the emission of radiation based on the timing signal ends or the timing when the charge accumulated by the emission of radiation is read. As a result, it is possible to reliably accumulate the charge obtained by the emission of radiation and to reliably acquire the images obtained by the emission of radiation.

The timing signal may not be used for the start of each operation, but may be used for the end of each operation. For example, the accumulation operation may start at the timing when the timing signal changes from an off state an on state and may end at the timing when the timing signal changes from the on state to the off state.

This control enables the additional controller 61 to reliably acquire the images obtained by the emission of radiation as in each of the above-mentioned cases.

In this embodiment, the timing signal is repeatedly output with the same period as the irradiation permission signal.

In this embodiment, the additional controller 61 repeatedly outputs the irradiation permission signal until the number of outputs reaches a predetermined value or until a predetermined output time elapses from the first output.

The timing signal may be output with a predetermined time delay after the irradiation permission signal is output or may be output before the irradiation permission signal is output.

The additional controller 61 may be configured to include a time for controlling the timing in order to repeatedly transmit the timing signal or the irradiation permission signal with a predetermined period.

Further, the additional controller 61 may be configured to have a counter that counts the number of outputs in order to repeatedly output the timing signal or the irradiation permission signal until the number of times the timing signal or the irradiation permission signal is output reaches a predetermined value. Alternatively, the additional controller 61 may be configured to have a timer in order to repeatedly output the timing signal or the irradiation permission signal until a predetermined output time elapses from the first output of the timing signal or the irradiation permission signal.

The timing signal may be output in a stage before the irradiation instruction switch 5 is pressed to the second stage (the irradiation instruction signal is acquired).

Specifically, for example, the timing signal may be output until the irradiation instruction signal is acquired after a sequence start signal (a fifth signal in the invention) is acquired (the turn-on of the sequence start signal is detected) or until the irradiation preparation signal (a sixth signal in the invention) is acquired (the turn-on of the irradiation preparation signal is detected).

In some cases, a plurality of generation apparatuses are connected in the system 100. In this case, one of the generation apparatuses is selected and used.

Similarly, in some cases, a plurality of imaging apparatuses 3 are connected in the system 100. In this case, one of the imaging apparatuses 3 is selected and used.

FIG. 4 illustrates an example of the system 100 including a plurality of generation apparatuses and a plurality of imaging apparatuses 3. In the example of the system 100 illustrated in FIG. 4, one decubitus imaging table 8A and an upright imaging table 8B are installed in an imaging room (not illustrated) and a generation apparatus (A) and a generation apparatus (B) are installed so as to mainly correspond to imaging with these tables.

An imaging apparatus (A) is mainly installed in the decubitus imaging table 8A and an imaging apparatus (B) is mainly installed in the upright imaging table 8B. Each of the decubitus imaging table 8A and the upright imaging table 8B is configured to accommodate the imaging apparatus 3 such that the imaging apparatus 3 can be changed.

An imaging apparatus (C) for capturing an image of a part, such as a hand or a foot, without using an imaging table is installed in the imaging room, separately from the imaging apparatuses (A) and (B). In a case where the imaging apparatus (C) is used, for example, imaging may be performed using the generation apparatus (A) placed on the decubitus imaging table 8A or may be performed while changing the irradiation direction of the generation apparatus (B).

In addition, the console 4 and a plurality of apparatuses (the radiation control devices 1 and 1A and the additional apparatuses 6 and 6A) may be connected to each other through a communication device 9 illustrated in FIG. 4 or the communication network N.

In this configuration, for example, in the capture of still images, particularly, in a case where there are no restrictions on the size of the image that can be captured, it is possible to minimize the replacement of the imaging apparatus 3 or the movement the radiation generator 2 and thus to effectively perform imaging.

However, for example, in a case where the size or resolution of the image that can be captured by each imaging apparatus 3 are not matched with an imaging method to be performed, imaging is performed while changing the imaging apparatuses (A), (B), and (C).

Operation

The operation of the system 100 will be described. FIGS. 5 and 6 are ladder charts illustrating the operation of the system 100 according to this embodiment and FIG. 7 is a timing chart illustrating the operation of the system 100.

A: When Apparatus is Installed, when Apparatus Starts Up, when Connected Apparatus is Changed, and when Connected Apparatus is Periodically Checked First, the console 4, particularly, the imaging apparatus control console 42 checks the imaging apparatus 3 or the additional apparatus 6 connected to an imaging environment controlled by the console 4 when an apparatus is installed, an imaging system starts up, when the connected apparatus is changed, and when the connected apparatus is periodically checked as illustrated in FIG. 5 (Step S1) and displays an apparatus configuration and a connection configuration on the display 43 of the console 4 (Step S2).

The imaging apparatus 3 and the additional apparatus 6 connected to the imaging environment controlled by the console 4 can be checked by, for example, a method in which the console 4 requests the imaging apparatus 3 and the additional apparatus 6 to transmit information indicating whether the apparatuses are connected and IDs and the imaging apparatus 3 and the additional apparatus 6 return the information indicating whether the apparatuses are connected and IDs.

For example, the unique ID of each apparatus, such as a MAC address uniquely set to an apparatus, the unique BSSID of an apparatus, or a serial number uniquely set to an apparatus, may be used as the ID. In addition, an ID that is set later, such as a set IP address or a set ESSID, may be used.

B: Preparation for Imaging

Then, if the console 4 receives an imaging order from the host system 7 such as RIS or HIS (Step S3), the console 4 displays the received imaging order on a screen of the console 4 (Step S4).

At that time, the reception of a new imaging order may be notified to an operator using light or sound.

The radiographer performs, for example, an operation of changing an imaging sequence from the displayed imaging order and selects an imaging order for the next imaging (Step S5).

At that time, an imaging apparatus 3 to be used may be selected from a plurality of connected imaging apparatuses 3.

In addition, a recommended imaging apparatus 3 may be automatically selected from the plurality of connected imaging apparatuses 3 according to the imaging technique of the radiographer.

In a case where there is no particular change in the imaging order, the imaging apparatus 3 used in the previous imaging operation may be continuously selected.

If the imaging apparatus 3 to be used is selected, the console 4 transmits a connection request to the imaging apparatus 3 and the additional apparatus 6 (Step S6).

If the imaging apparatus 3 or the additional apparatus 6 receives the connection request, it is connected to the console 4 (Step S7).

As illustrated in FIG. 5, the connection request may be transmitted from the console 4 to the additional apparatus 6 and may be further transmitted from the additional apparatus 6 to the imaging apparatus 3.

As illustrated in FIG. 2, the imaging apparatus 3 and the console 4 can be connected to each other through the communication network N or can be directly connected to each other. In a case where the console 4 and the imaging apparatus 3 are directly connected to each other, the console 4 is connected to the imaging apparatus 3 that is not connected to the additional apparatus 6 and there is a possibility that a connection configuration will not be established in a state in which the additional apparatus 6 and the imaging apparatus 3 cooperate with each other.

However, this connection between the imaging apparatus 3 and the console 4 through the additional apparatus 6 makes it possible for the console 4 to be reliably connected to the imaging apparatus 3 connected to the additional apparatus 6.

Alternatively, the console 4 may transmit a connection request to each imaging apparatus 3 and then each imaging apparatus 3 may transmit a connection request to the additional apparatus 6, which is not illustrated.

Since the console 4 sets the imaging apparatus 3 to be used for imaging, this configuration makes it possible to reliably select the imaging apparatus 3 to be used, to connect the imaging apparatus 3 and the additional apparatus 6, and to establish a state in which the additional apparatus 6 and the imaging apparatus 3 that is used cooperate with each other, without selecting a wrong imaging apparatus 3.

In addition, this configuration makes it possible to select an imaging apparatus 3 not only from the imaging apparatus 3 connected to the additional apparatus 6 as described above but also from all of the usable imaging apparatuses 3.

In a case where the imaging apparatus 3 starts connection, the imaging apparatus 3 may automatically change its state from the above-mentioned mode in which preparation for imaging or imaging is possible and power consumption is low to a mode in which power consumption is higher than that in the low-power-consumption mode.

Then, if the radiographer sets, for example, imaging conditions with the console 4 and instructs the console 4 to start imaging, the console 4 turns on the sequence start signal that instructs the imaging apparatus 3 and the additional apparatus 6 to start an imaging sequence. Then, the console 4 transmits the sequence start signal to the imaging apparatus 3 and the additional apparatus 6 (Step S8). The sequence start signal can be transmitted using, for example, the information signal which is transmitted and received between the console 4 and the additional apparatus 6 and the information signal which is transmitted and received between the additional apparatus 6 and the imaging apparatus 3.

If the imaging apparatus 3 and the additional apparatus 6 detect that the sequence start signal has been turned on, they start preparation for imaging.

In a case where the additional apparatus 6 is configured to transmit the timing signal in a stage before the irradiation instruction switch 5 is pressed, the additional apparatus 6 may perform control such that a reading instruction signal (see FIG. 22) is turned on and the timing signal is repeatedly transmitted to the imaging apparatus 3 at predetermined intervals after it is detected that the sequence start signal has been turned on (Step S9).

The imaging apparatus 3 repeats a reading operation whenever the timing signal is received. Then, the temperature of the circuit in the imaging apparatus 3 rises. That is, the reading operation which is repeatedly performed by the imaging apparatus 3 in this stage is the warm-up of the imaging apparatus 3.

In an initial stage in which the imaging apparatus 3 repeats the reading operation, the imaging apparatus 3 notifies the console 4 that a warm-up has started (Step S10).

The imaging apparatus 3 needs to perform a reading operation (reset operation) for removing the charge accumulated immediately before imaging.

Since the imaging apparatus 3 consumes power in the reading operation, the temperature of the imaging apparatus 3 rises with an increase in the power consumption. The sensitivity of a light receiver of the imaging device 3 is particularly changed by the temperature rise and image density based on the incident amount of radiation also changes. The change in image density due to the temperature rise is not a problem in a case where one still image is captured. However, in a case where dynamic imaging (for repeatedly capturing still images) is performed as in the system 100 according to this embodiment, the change in image density due to the temperature rise during imaging becomes a problem.

However, the above-mentioned configuration in which the imaging apparatus performs a warm-up makes it possible to reduce the change in image density due to the temperature rise.

The imaging apparatus 3 may acquire a correction image at any timing when Step S9 is repeated a plurality of times.

For example, in a case where the imaging apparatus 3 is configured to perform a warm-up (to perform the reading operation before the irradiation instruction switch 5 is pressed), the imaging apparatus 3 may transmit an image which has been read in the second half of the warm-up as the correction image to the console 4 (Step S11).

A plurality of pixels of the imaging apparatus 3 have different characteristics and the charge levels corresponding to the brightness of the image are different in the pixels even when radiation is not emitted. Therefore, the image read in the second half of the warm-up is acquired as the correction image and, for example, each signal value of the correction image is subtracted from each signal value of a captured image which is obtained later to obtain a captured image in which a variation for each pixel has been removed.

In this embodiment, a case where the correction image is simply subtracted from the captured image has been described as an example of the method of using the correction image. However, noise components may be removed using various operations.

In a case where the read operation (reset operation) for removing the charge accumulated immediately before imaging other than the acquisition of the correction image is performed, at least one of the following processes may be performed as the same operation as that in normal imaging:

a process of converting the removed charge into an image;

a process of storing the image data of the obtained image in the storage of the imaging apparatus 3; and a process of transmitting the imaged data or the image data stored in the storage of the imaging apparatus 3 to the console 4.

The above-mentioned process which is the same as that in normal imaging is performed under the conditions close to those of actual imaging Therefore, according to this configuration, a difference in imaging in the subsequent steps is small and it is possible to reduce, for example, the influence of the temperature rise.

In contrast, in a case where the above-mentioned process which is the same as that in normal imaging is performed, the following problems arise:

the amount of power consumption increases;

since an unnecessary image obtained while no radiation is emitted is stored in the storage of the imaging apparatus 3, the capacity of the storage that can be used at the time of imaging is reduced;

since the unnecessary image obtained while no radiation is emitted is transmitted to the console, the transmission of the unnecessary image occupies a part of communication capacity; and since the unnecessary image is stored in the storage of the console, the capacity of the storage that can be used at the time of imaging is reduced.

Therefore, some of the processes may be omitted in order to avoid the problems.

The imaging apparatus 3 can be configured to complete the warm-up in a case where the number of reading operations as the warm-up reaches a predetermined value or the reading operation period has elapsed. For example, in Step S25 (see FIG. 6) in which the irradiation start signal is turned on, which will be described below, control is performed such that the irradiation start signal is not turned on until the number of reading operations reaches a predetermined value or the reading operation period elapses, which makes it possible not to start imaging using the emission of radiation until the warm-up is completed.

Then, the imaging apparatus 3 notifies the console 4 that preparation for imaging has been completed (Step S12).

At that time, "Imaging is available" may be displayed on the display 43 of the console 4 (Step S13).

C: Imaging Check

The additional apparatus 6 continues to repeatedly transmit the timing signal to the imaging apparatus 3 and the imaging apparatus 3 repeats the reading operation of the imaging apparatus 3 whenever the timing signal is received.

If the radiographer ends the positioning of the subject and presses the irradiation instruction switch 5 to the first stage (Step S14), the irradiation instruction switch 5 turns on the irradiation preparation signal output to the radiation controller 11 through the console 4 (Step S15).

If the radiation controller 11 of the radiation generation apparatus detects that the irradiation preparation signal has been turned on, it turns on the irradiation preparation signal output to the high voltage generator 12 and the additional apparatus 6 (Step S16). Then, the first acquirer 62 of the additional apparatus 6 acquires the irradiation preparation signal (which is output before the irradiation instruction signal and after the sequence start signal is turned on).

As such, the radiation generation apparatus including the radiation controller 11 starts preparation for the emission of radiation in response to the irradiation preparation signal.

If the additional controller 61 of the additional apparatus 6 detects that the irradiation preparation signal from the radiation controller 11 has been turned on, it transmits the imaging preparation signal to the console 4 (Step S17).

If the console 4 receives the imaging preparation signal, it starts preparation for imaging. The preparation for imaging in the console 4 is, for example, an operation of checking whether the settings of the imaging apparatus control console 42 and the settings of the radiation control console 41 that controls the emission of radiation in the console 4 are the same or an operation of checking whether the designated imaging conditions are set in the imaging apparatus 3.

If preparation for imaging is completed, the console 4 turns on an imaging preparation completion signal output to the additional apparatus 6 (Step S18).

At that time, "Imaging is being performed" may be displayed on the display 43 of the console 4 (Step S19).

In the stage in which the preparation for imaging has been completed, for example, the input of an instruction to change the imaging conditions to the console 4 may be locked such that the imaging conditions are not changed.

In a case where a still image is captured, imaging ends in a short time. Therefore, the risk of changing the conditions during imaging is low and there is little need for this configuration. However, in the case of dynamic imaging, since the imaging period is long, there is a high risk that the radiographer or a third party other than the radiographer will intentionally or unintentionally operate a console screen to change the imaging conditions.

For this reason, in the process from this stage to the end of the sequence after Step S45 which will be described below, the input of, for example, an instruction to change the imaging conditions to the console 4 is locked, which makes it possible to reliably prevent the change in the imaging conditions.

FIG. 5 illustrates a case where the imaging preparation signal is output from the additional apparatus 6 to the console 4. However, in some cases, the imaging preparation signal is not output to the console 4, but is output to the imaging apparatus 3 such that the imaging apparatus 3 prepares imaging and the imaging preparation completion signal is output from the imaging apparatus 3 to the additional apparatus 6 after the imaging apparatus 3 completes preparation for imaging.

Further, in some cases, the imaging preparation signal is input to both the console 4 and the imaging apparatus 3 such that both the console 4 and the imaging apparatus 3 prepare imaging and the imaging preparation completion signal is output from the console 4 and the imaging apparatus 3 to the additional apparatus 6 after both the console 4 and the imaging apparatus 3 complete preparation for imaging. Then, it is determined that the entire preparation for imaging has been completed in a stage in which the additional apparatus 6 has received the imaging preparation completion signal from both the console 4 and the imaging apparatus 3.

In a case where the radiation controller 11 of the radiation generation apparatus has a connector that can input the imaging preparation completion signal indicating that preparation for imaging in the external device has been completed, the additional apparatus 6 may output the imaging preparation completion signal to the radiation controller 11, which is not illustrated.

The radiation controller 11 detects that the imaging preparation completion signal from the additional apparatus 6 has been turned on to detect that the imaging apparatus 3 is in a state in which it can perform imaging Since the radiation control device 1 performs control such that radiation is emitted after it is detected that the imaging preparation completion signal has been turned on, it is possible to surely eliminate the risk that the imaging apparatus 3 will emit radiation while imaging is not possible and the subject will be unnecessarily exposed to radiation.

D: Execution of Imaging

Then, if the radiographer presses the irradiation instruction switch 5 to the second stage (Step S20), the irradiation instruction switch 5 turns on the irradiation instruction signal transmitted to the radiation controller 11 through the console 4 (Step S21).

In this case, the additional apparatus 6 continues to repeatedly transmit the timing signal to the imaging apparatus 3 and the imaging apparatus 3 repeats the reading operation whenever the timing signal is received.

Even if the irradiation instruction signal is input from the irradiation instruction switch 5, the radiation controller 11 of the radiation generation apparatus does not transmit the irradiation signal to the high voltage generator 12 since the irradiation permission signal from the additional apparatus 6 is in an off state at this time.

The radiation controller 11 turns on the irradiation instruction signal transmitted to the additional controller 61 (Step S22).

In a case where the additional apparatus 6 receives the irradiation instruction signal, the additional apparatus 6 turns on the imaging start signal which notifies whether to permit the start of imaging and is output to the imaging apparatus 3 and the console 4 (Steps S23 and S24).

In a case where it is detected that the imaging start signal has been turned on, for example, the imaging apparatus 3 turns on the irradiation start signal output to the additional apparatus 6, using the end of its reading operation performed at that time as a trigger, as illustrated in FIG. 6 (Step S25). The reason is as follows. The reading operation of the imaging apparatus 3 sequentially reads the charge accumulated in the pixels which are two-dimensionally arranged to acquire the image of the entire light receiving surface. In a case where the irradiation start signal is turned on to emit radiation during the reading operation, there is a difference between the signal value of the pixel from which the reading of charge has been completed and the signal value of the pixel from which the reading of charge has not been completed. As a result, image quality is significantly degraded.

In contrast, in this embodiment, the emission of radiation and the image reading operation of the imaging apparatus 3 are performed on the basis of the irradiation permission signal and the timing signal from the additional apparatus 6, which will be described below. Therefore, the emission of radiation during the reading operation does not occur in a normal routine. Thus, the irradiation start signal may be turned on, without considering the reading timing of the imaging apparatus 3.

The imaging apparatus 3 repeats the image reading operation even after the irradiation start signal is turned on. The image read after the irradiation start signal is turned on is stored as the captured image in the memory of the imaging apparatus 3 or is transmitted to the console 4.

If the additional apparatus 6 detects that the irradiation start signal from the imaging apparatus 3 has been turned on, it detects that the imaging apparatus 3 is in a state in which the imaging apparatus 3 can perform imaging and repeatedly transmits the irradiation permission signal to the radiation controller 11 whenever the timing signal is transmitted to the imaging apparatus 3 (Step S26).

The radiation controller 11 of the radiation generation apparatus repeatedly transmits the irradiation signal to the high voltage generator 12 since the imaging instruction signal and the irradiation permission signal are aligned whenever the irradiation permission signal is received.

Whenever the irradiation signal is received, the high voltage generator 12 repeatedly generates a high voltage required for emitting radiation and repeatedly outputs the high voltage as an irradiation output to the radiation generator 2.

The radiation generator 2 repeatedly emits radiation to the imaging apparatus 3 whenever the irradiation output is input (Step S27).

The emitted radiation is transmitted through the subject (not illustrated) disposed between the imaging apparatus 3 and the radiation generator 2 and is then incident on the imaging apparatus 3.

Whenever the timing signal is received, the imaging apparatus 3 repeats a process of accumulating the amount of charge corresponding to the intensity of the incident radiation (Step S28) and reading the charge as a captured image (Step S29).

The imaging apparatus 3 transmits the read radiographic image to the console 4 (Step S30).

In a case where the captured image is configured to be transmitted to the console 4 and is not transmitted to the console 4 in time due to the amount of data or a communication environment, some of a plurality of captured images or a part of one captured image may be stored in the imaging apparatus 3 and the rest may be transmitted to the console 4.

An example of the operation of the imaging apparatus 3 will be further described. Here, a case where the accumulation of charge starts in response to the timing signal will be described.

Reset Operation/Correction Image Acquisition Operation

In the reset operation performed before imaging, the imaging apparatus 3 can repeat the above-mentioned operation while there is no radiation emitted from the radiation generation apparatus to output the charge (a dark charge or a dark current) which has been accumulated in each pixel and is not based on the emission of radiation, thereby resetting the charge which has been accumulated in each pixel, is not based on the emission of radiation, and is a noise component with respect to the image obtained by the charge based on the emission of radiation. Further, in the reset operation, control may be performed which the reader 34 does not convert the input charge into image data (operation before t1).

In a correction image acquisition operation performed before or after imaging, the imaging device 3 can repeat the above-mentioned operation while there is no radiation emitted from the radiation generation apparatus to output the charge (a dark charge or a dark current) which has been accumulated in each pixel and is not based on the emission of radiation, thereby resetting the charge which has been accumulated in each pixel, is not based on the emission of radiation, and is a noise component with respect to the image obtained by the charge based on the emission of radiation. In the correction image acquisition operation, the reader 34 converts the input charge into image data and the image data is stored. Therefore, it is possible to store a noise component while radiation is not emitted and to remove the noise component by subtracting the noise component from the image data obtained while radiation is emitted. The correction image acquisition operation may be performed as a part of the reset operation (operation before t1).

Operation of Ending Reset Operation/Correction Image Acquisition Operation

If the irradiation instruction signal in Step S21 is turned on following the reset operation or the correction image acquisition operation, the imaging start signal input to the imaging apparatus 3 is turned on (Step S23). Then, the imaging apparatus 3 stops the reset operation or the correction image acquisition operation.

In a case where the correction image acquisition operation has not completed the acquisition of a predetermined number of correction images even though the imaging start signal has been turned on, the correction image acquisition operation is not stopped and is continuously performed until a predetermined number of correction images are acquired. Then, the correction image acquisition operation is stopped.

If the reset operation or the correction image acquisition operation is stopped, the imaging apparatus 3 stops the reset operation or the correction image acquisition operation and turns on the irradiation start signal in Step S25 to notify that the imaging apparatus 3 is in a state in which it can perform imaging (t1).

Operation

In a case where the imaging apparatus 3 receives the timing signal from the additional controller 61, it applies the off-voltage to each scanning line 32b and changes to a state in which the charge generated by the radiation detection element 32d can be accumulated in the pixel, as illustrated in FIG. 7 (t2, t6, t10, . . . ).

The additional controller 61 outputs the irradiation permission signal at the timing that is operatively associated with the timing when the timing signal is transmitted. The radiation generation apparatus irradiates the imaging apparatus 3 with radiation in response to the irradiation permission signal (Step S27; t3, t7, t11, . . . ).

The imaging apparatus 3 continues the mode for accumulating charge for a predetermined period of time, using a timer provided in the imaging apparatus 3 (t2 to t4, t6 to t8, t10 to t12, . . . ).

In a case where the imaging apparatus 3 receives radiation in the mode for accumulating charge, each radiation detection element 32d of the radiation detector 32 generates charge and the charge is accommodated in each pixel (Step S28).

Then, the imaging apparatus 3 performs the reading operation which applies the on-voltage to each switching element 32e after the predetermined period of time elapses using the timer provided in the imaging apparatus 3 to output the charge accumulated in each pixel to the signal line 32c. In the reading operation of the imaging apparatus 3, the reader 34 reads the input charge and converts the charge into image data. In addition, the imaging apparatus 3 transmits at least a part of the image data to the console 4 (Steps S29 and S30; t4 to t5, t8 to t9, t12 to t13, . . . ).

Another Embodiment of Operation Control Method

The example in which the imaging apparatus changes to a state in which it can accumulate charge in the pixels in response to the timing signal from the additional controller 61 has been described above. However, control may be performed such that the imaging apparatus performs other operations in response to the timing signal.

For example, another control method may perform control such that, after the imaging apparatus 3 ends the reading operation (t4 to 5, t8 to t9, t12 to t13, . . . ) of discharging the charge accumulated in each pixel to the signal line 32c, the imaging apparatus 3 changes to the state (t6 to t8, t10 to t12, . . . ) in which it can accumulate charge in the pixels, without waiting for the timing signal from the additional controller 61.

Then, the additional controller 61 performs control such that the timing signal is output at the timing which is operatively associated with the timing when the radiation generation apparatus transmits the irradiation permission signal for radiation emission control.

The imaging apparatus 3 changes to the reading operation that outputs the charge accumulated in each pixel to the signal line 32c in response to the received timing signal (t4, t8, t12, . . . ).

The repetition of the above-mentioned operation control makes it possible to perform imaging while matching the radiation emission timing of the radiation generation apparatus and the image generation timing of the imaging apparatus.

E: End of Imaging

The additional apparatus 6 counts the number of times the irradiation permission signal is transmitted from the time when the emission of radiation starts and determines whether the number of captured images reaches a predetermined maximum value whenever the number of times the irradiation permission signal is transmitted is counted. In a case where it is determined that the counted number of times the irradiation permission signal is transmitted (the number of captured images) reaches the maximum number of captured images, the additional apparatus 6 turns off the imaging start signal (Step S31) and stops the output of the timing signal or/and the irradiation permission signal.

Control may be performed such that the imaging apparatus 3 performs the operation of accumulating the amount of charge corresponding to the intensity of the incident radiation (Step S28) and reading the charge as a captured image (Step S29) at least once after the additional apparatus 6 outputs the irradiation permission signal last. In this case, it is possible to reliably read the image obtained by the last emission of radiation, to use the read image as the captured image, and to reliably prevent the subject from being unnecessarily exposed to radiation.

In addition, control may be performed such that the imaging apparatus 3 further performs the operation of accumulating charge and reading the charge as a captured image after the additional apparatus 6 outputs the irradiation permission signal last, and then the imaging apparatus 3 performs the operation of accumulating charge (Step S28) and reading the charge as a captured image (Step S29). Since the captured image is an image captured while no radiation is emitted, these images can be used to correct the images captured while radiation is emitted, similarly to the correction image.

In other words, for the correction image, an image captured before imaging using radiation as described above may be used as the correction image or an image captured after imaging using radiation as described above may be used as the correction image.

Alternatively, the correction images captured before and after imaging using radiation may be used. In this case, the correction images captured before and after imaging using radiation may be used to predict a change in the correction image during imaging and the correction image may be generated on the basis of the prediction result. The correction image can be generated, for example, by averaging the correction images captured before and after radiography or by performing linear or curve compensation for fluctuations.

In a case where a still image is captured, since the time required for imaging is short, a change in the correction image before and after imaging is small. However, in the case of dynamic imaging, the time required for imaging is longer than that in a case where a still image is captured. Therefore, in a case where the correction images before and after imaging are used as described above, it is possible to perform correction, also considering fluctuations during imaging.

The number of captured images may not be counted on the basis of the number of times the irradiation permission signal is transmitted as described above, but may be counted on the basis of the number of times the timing signal is output after the start of imaging.

In addition, the number of captured images may not be counted on the basis of the number of times the irradiation permission signal is transmitted as described above, but may be counted on the basis of the time elapsed since the start of imaging.

If it is detected that the imaging start signal has been turned off and imaging after radiation is emitted or imaging for acquiring the correction image ends, the imaging apparatus 3 turns off the reading instruction signal (see FIG. 22) and transmits the images remaining in the memory of the imaging apparatus 3 (the captured images which have not been transmitted) to the console 4 (Step S32). Then, if the transmission of the remaining images is completed, the imaging apparatus 3 transmits a remaining image transmission completion signal to the console 4 (Step S33).

If the console 4 detects that the imaging start signal has been turned off, it starts an operation of checking the transmitted captured image.

If the console 4 receives the remaining image transmission completion signal, it transmits an image deletion signal for instructing the deletion of an image to the imaging apparatus 3 (Step S34).

Control may be performed such that the image deletion signal is transmitted after the captured image check operation is completed and it is checked that there is no problem in all of the transmitted images.

At that time, "End of imaging" may be displayed on the display 43 of the console 4 (Step S35).

In a case where the imaging apparatus 3 receives the image deletion signal, it deletes the captured images stored in the memory (Step S36). Therefore, the free space of the memory can be ensured for the next imaging.

If the radiographer who has checked the end of imaging (for example, who has seen "the end of imaging" displayed on the console 4) releases the second stage of the irradiation instruction switch 5 (Step S37), the irradiation instruction switch 5 turns off the irradiation instruction signal (Step S38) and the radiation controller 11 also turns off the irradiation instruction signal (Step S39).

Then, if the radiographer opens the first stage of the irradiation instruction switch 5 (Step S40), the irradiation instruction switch 5 turns off the irradiation preparation signal (Step S41) and the radiation controller 11 also turns off the irradiation preparation signal (Step S42).

If the additional apparatus 6 detects that the irradiation preparation signal has been turned off, it notifies the console 4 that the irradiation preparation signal has been turned off.

If the console 4 receives the notification from the additional apparatus 6, it turns off the imaging preparation completion signal and changes a sequence state to an irradiation preparation state.

If the additional apparatus 6 detects that the irradiation instruction signal and the irradiation preparation signal have been turned off, it transmits an imaging end signal indicating that imaging has ended to the imaging apparatus 3 and the console 4 (Steps S43 and S44).

If the imaging apparatus 3 receives the imaging end signal, it transmits a standby signal to the console 4 (Step S45).

If the console 4 receives the standby signal, it monitors the presence and absence of re-imaging or another imaging for a predetermined period. In a case where there is no re-imaging or another imaging for a predetermined period, the console 4 turns off the sequence start signal to change the sequence state to a standby state in which it waits for an imaging instruction.

In this way, a series of imaging operations ends.

The system 100 according to this embodiment operates as described above and dynamic imaging that repeatedly captures a plurality of still images in a short time is performed.

Effect

As described above, the system 100 according to the first embodiment is configured by connecting the additional controller 61 to the radiation control device 1 that can perform the emission of radiation only once in response to one radiation emission instruction in the conventional system 100A illustrated in FIG. 1. In the system 100, the radiation control device 1 can output the irradiation signal a plurality of times in response to one irradiation instruction signal acquisition operation (the detection of the turn-on of the irradiation instruction signal). Therefore, it is possible to perform imaging that repeatedly captures still images a plurality of times in a short time, that is, dynamic imaging using the imaging apparatus 3.

The conventional system 100A illustrated in FIG. 1 is widely used as a radiography apparatus that captures a simple still image. Therefore, a medical institution using the conventional system 100A can easily modify the conventional system 100A including the existing radiation generation apparatus so as to respond to the dynamic imaging only by adding the imaging apparatus 3 and the additional apparatus 6, without updating the expensive radiation generation apparatus.

Second Embodiment

A second embodiment of the invention will be described with reference to FIGS. 2 to 5 and 8 to 14. The same configurations as those in Conventional Technology 1 and the first embodiment are denoted by the same reference numerals and the description thereof will not be repeated. In addition, various modification patterns described in the first embodiment may also be applied to this embodiment.

System Configuration

First, a system configuration of a radiography system (hereinafter, referred to as a system 100) according to this embodiment will be described. FIG. 2 is a block diagram illustrating the system 100 and FIG. 3 is a block diagram illustrating a radiography apparatus 3.

For example, similarly to the system 100 according to the first embodiment, the system 100 according to this embodiment differs from the conventional system 100A in that the radiography apparatus (hereinafter, referred to as the imaging apparatus 3) replaces the cassette 3A and the imaging apparatus control console 42 and the additional apparatus 6 are added, as illustrated in FIG. 2.

Operation

Figure 11:
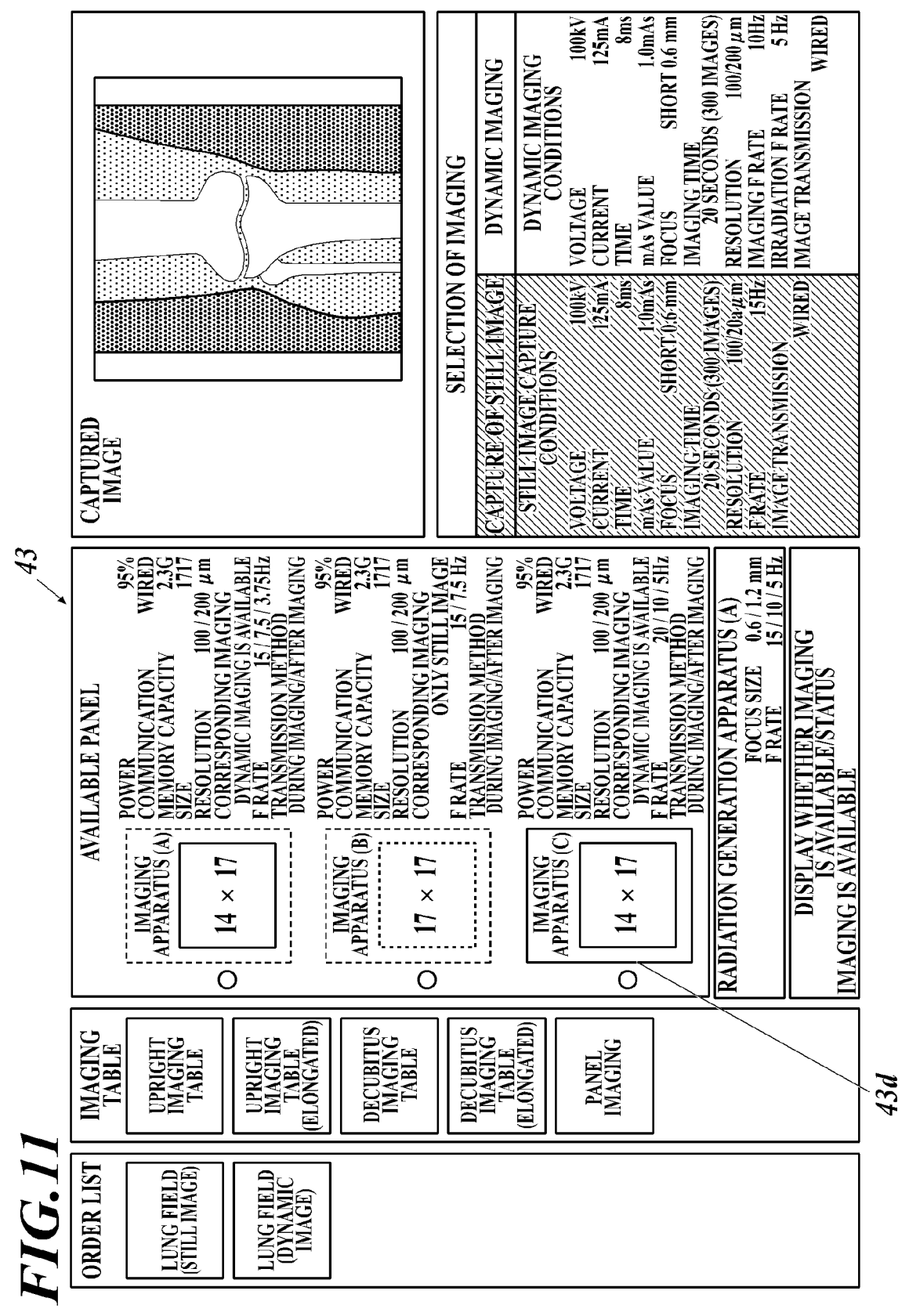
Figure 12:
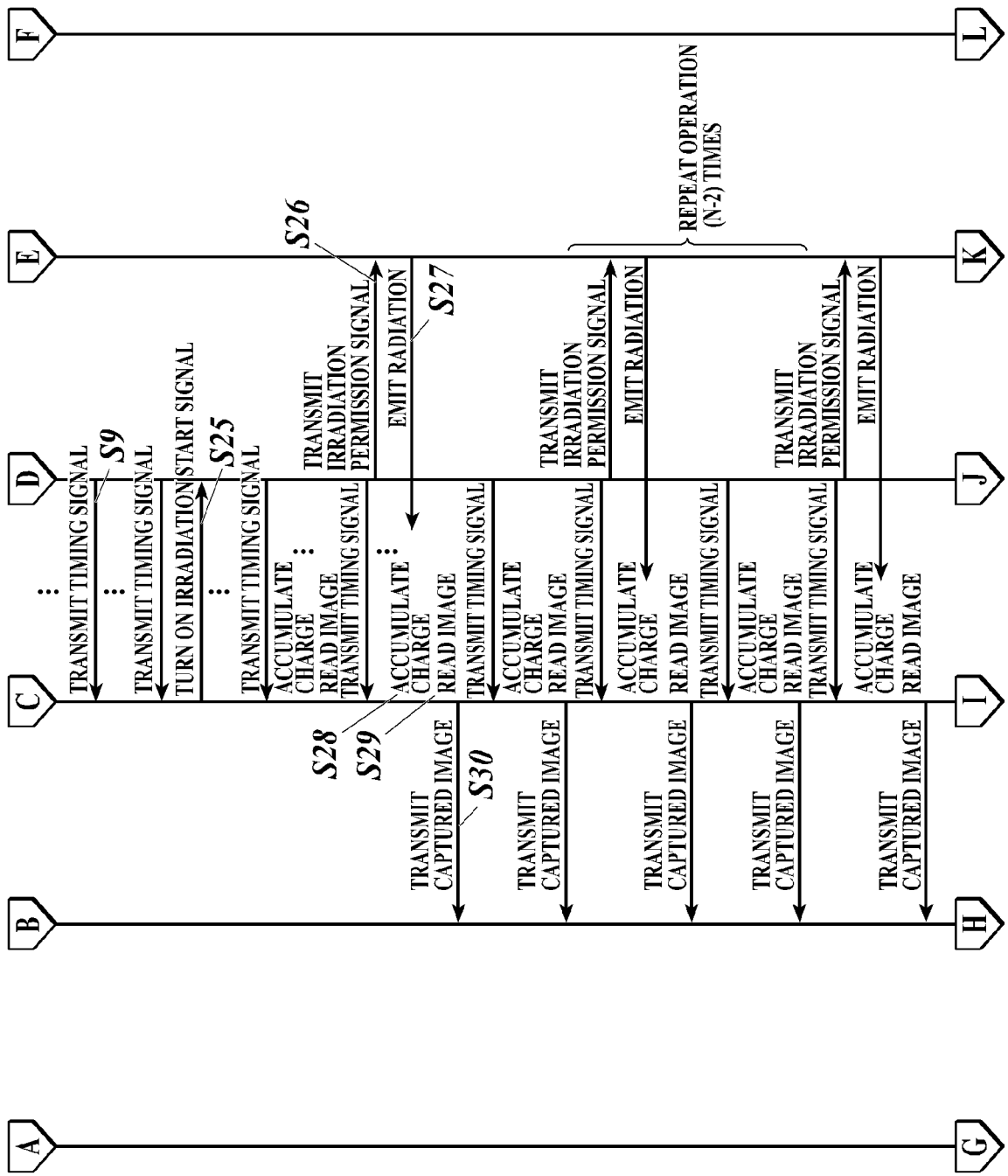
FIG. 12 is a ladder chart illustrating the middle of the operation of the radiography system according to the second embodiment.
Figure 13:
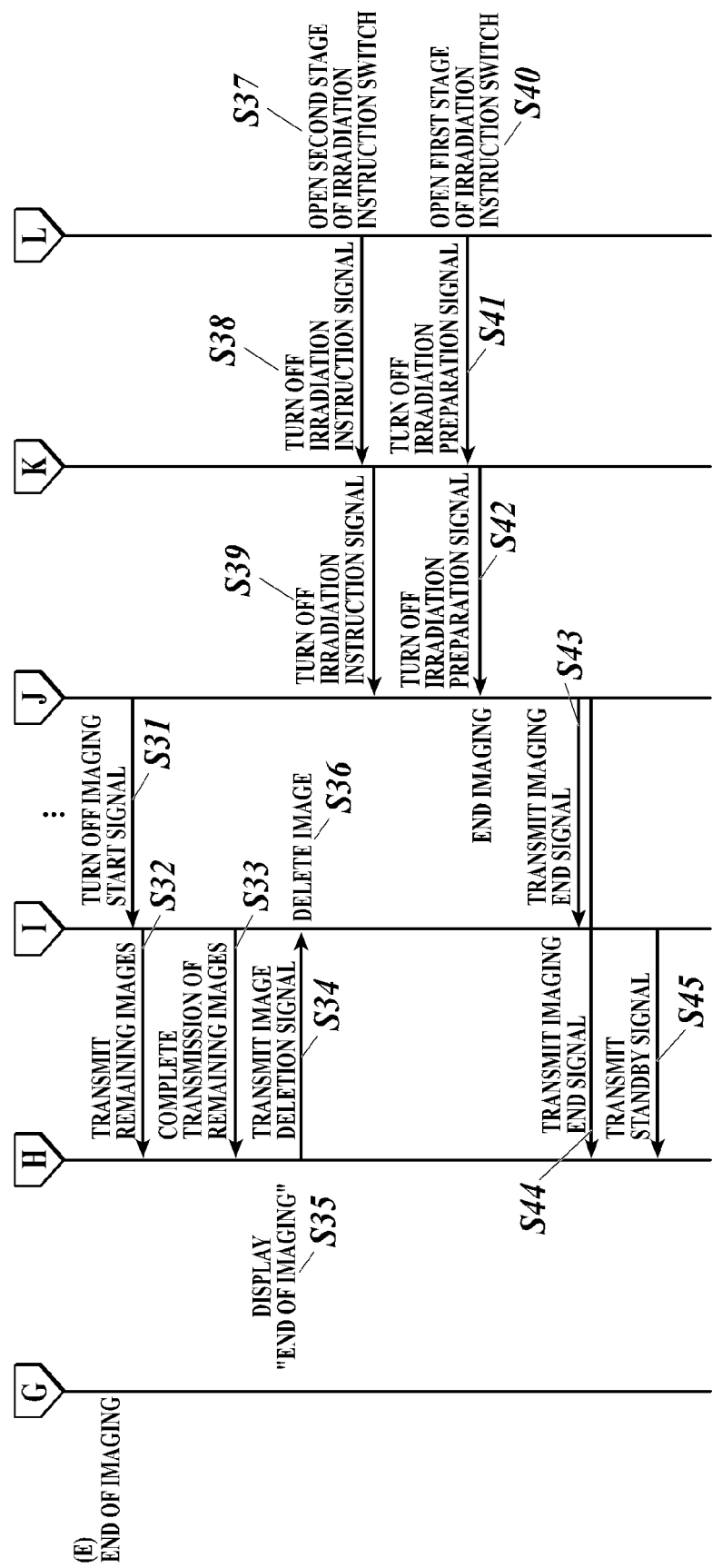
FIG. 13 is a ladder chart illustrating the second half of the operation of the radiography system according to the second embodiment.
Figure 14:
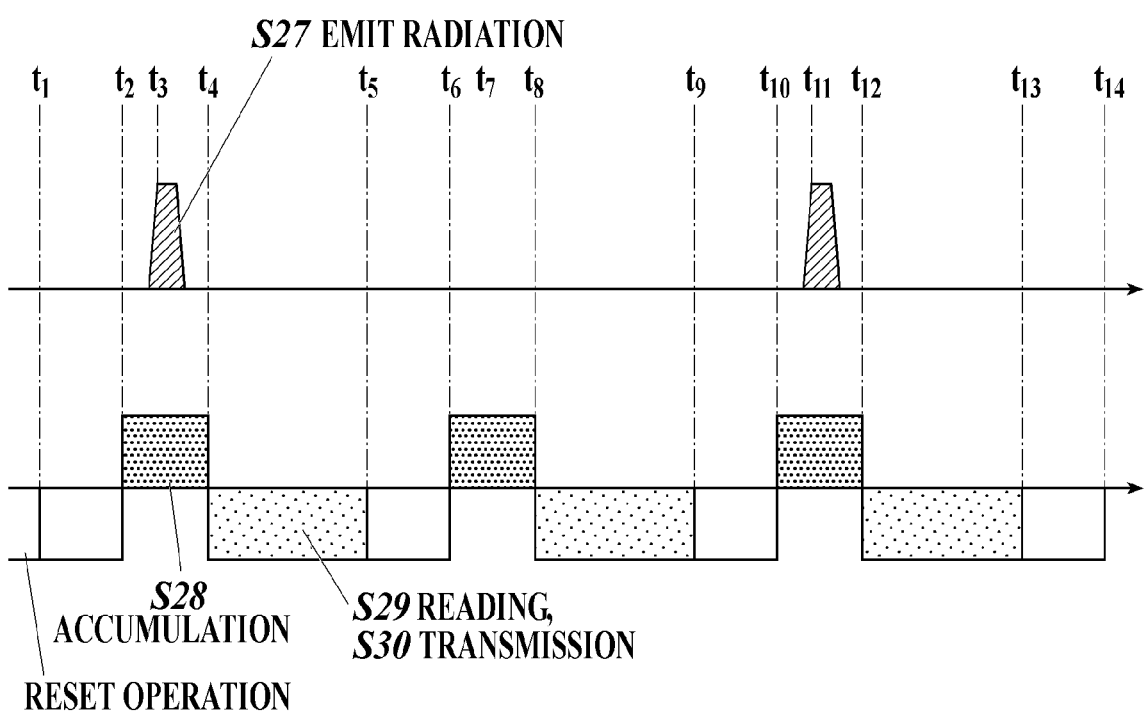
FIG. 14 is a timing chart illustrating the operation of the radiography system according to the second embodiment.

The operation of the system 100 will be described. FIGS. 5, 12, and 13 are ladder charts illustrating the operation of the system 100 according to this embodiment. FIG. 8 is a table illustrating the correspondence between generation apparatuses and the imaging apparatuses 3 that can be connected to the system 100 and the frame rates corresponding to these apparatuses. FIGS. 9 to 11 illustrate examples of the display screen of the display 43 of the console 4. FIG. 14 is a timing chart illustrating the operation of the system 100.

A: When Apparatus is Installed, when Apparatus Starts Up, when Connected Apparatus is Changed, and when Connected Apparatus is Periodically Checked First, the console 4, particularly, the imaging apparatus control console 42 checks the imaging apparatus 3 or the additional apparatus 6 connected to an imaging environment controlled by the console 4 when an apparatus is installed, an imaging system starts up, when the connected apparatus is changed, and when the connected apparatus is periodically checked as illustrated in FIG. 5 (Step S1) and displays an apparatus configuration and a connection configuration on the display 43 of the console 4 (Step S2).

The imaging apparatus 3 and the additional apparatus 6 connected to the imaging environment controlled by the console 4 can be checked by, for example, a method in which the console 4 requests the imaging apparatus 3 and the additional apparatus 6 to transmit information indicating whether the apparatuses are connected and IDs and the imaging apparatus 3 and the additional apparatus 6 return the information indicating whether the apparatuses are connected and IDs.

For example, the unique ID of each apparatus, such as a MAC address uniquely set to an apparatus, the unique BSSID of an apparatus, or a serial number uniquely set to an apparatus, may be used as the ID. In addition, an ID that is set later, such as a set IP address or a set ESSID, may be used.

B: Preparation for Imaging

Then, if the console 4 receives an imaging order from the host system 7 such as RIS or HIS (Step S3), it displays the received imaging order on the screen of the console 4 (Step S4).

At that time, the reception of a new imaging order may be notified to the operator using light or sound.

The radiographer performs, for example, an operation of changing an imaging sequence from the displayed imaging order and selects an imaging order for the next imaging (Step S5).

Unlike a fluoroscopic apparatus in which a combination of a radiation generating apparatus and a radiography apparatus is fixed, the system 100 according to this embodiment can perform imaging even in a case where a combination of the generation apparatus and the imaging apparatus 3 is changed. Therefore, it is possible to select an imaging apparatus suitable for the imaging order and the imaging technique from a plurality of cassette-type imaging apparatuses 3 having different sizes and performances and then perform imaging.

In this case, for example, an imaging apparatus 3 (for example, an imaging apparatus (A) or (C)) suitable for the current imaging is selected from a plurality of imaging apparatuses 3 that can be connected to the console 4 and can be used for imaging as illustrated in FIG. 8 and imaging is performed.

In the case of a system 100 in which a plurality of generation apparatuses are connected to one console 4, a generation apparatus (for example, a generation apparatus (A) or (B)) used for imaging is selected and imaging is performed.

If at least one of the generation apparatus and the imaging apparatus 3 is selected, the additional controller 61 of the additional apparatus 6 or the console 4 according to this embodiment can acquire an irradiation frame rate or an imaging frame rate.

The irradiation frame rate or the imaging frame rate to be acquired may be input (selected) to the console 4 by the radiographer or may be received from the generation apparatus or the imaging apparatus 3.

In a case where the irradiation frame rate or the imaging frame rate is received from the generation apparatus or the imaging apparatus 3, one frame rate selected in each apparatus may be received or all of a plurality of frame rates corresponding to each apparatus may be received.

It is necessary to satisfy all of the following determination conditions (1) to (3) in order to perform imaging without any problem.

(1) The acquired irradiation frame rate is a value corresponding to the generation apparatus.

(2) The acquired imaging frame rate is a value corresponding to the imaging apparatus 3.

(3) The ratio of the irradiation frame rate to the imaging frame rate is 1:N, where N is an integer equal to or greater than 1 (the imaging frame rate is N times the irradiation frame rate).

Therefore, the additional controller 61 or the console 4 determines whether or not all of the determination conditions are satisfied.

Here, the "irradiation frame rate" indicates the number of times radiation is generated by the generation apparatus per unit time and corresponds to the transmission period of the irradiation permission signal by the additional controller 61.

The "imaging frame rate" indicates the number of times a radiographic image is generated by the imaging apparatus 3 per unit time and corresponds to the transmission period of the timing signal by the additional controller 61.

In a case where at least one of the number of irradiation frame rates and the number of imaging frame rates is two or more, there are a plurality of combinations of the irradiation frame rates and the imaging frame rates. Therefore, determination may be performed a plurality of times in accordance with the plurality of combinations.

Here, N is an integer equal to or greater than 1. However, for example, in a case where imaging is performed while the emission of radiation is thinned out at predetermined intervals, it is preferable that N is an integer equal to or greater than 2.

In a case where at least one of the number of imaging frame rates received from the imaging apparatus 3 and the number of irradiation frame rates received from the generation apparatus is two or more, there may be a plurality of combinations of the imaging frame rates and the irradiation frame rates. Therefore, it may be determined in advance whether each combination satisfies all of the above-mentioned determination conditions.

In a case where the generation apparatus or the imaging apparatus is configured to select only the corresponding irradiation frame rate or the corresponding imaging frame rate, the generation apparatus, the imaging apparatus 3, or the console 4 can omit the determination of whether the determination conditions (1) and (2) are satisfied.

If any of the determination conditions is not satisfied as a result of checking whether all of the determination conditions are satisfied, at least one of the following measures (4) to (6) may be taken.

(4) Among the imaging apparatus 3 used, the generation apparatus used, the imaging frame rate of the imaging apparatus 3, and the irradiation frame rate of the generation apparatus, a component that does not satisfy the above-mentioned relationship is not selected or an input value is not received (not set).

(5) A setting candidate that does not satisfy the above-mentioned relationship is grayed out (display to notify the determination result is performed) and is excluded from a selection target such that it is not selectable.

(6) Even if a component can be selected, it does not advance to the next sequence. Alternatively, imaging is not permitted.

The system may notify the photographer of an error to warn the photographer that the relationship is not satisfied when the above-described measures are taken. The warning may be performed by voice or may be performed by display for notifying the determination result using the display 43.

That is, the additional controller 61 or the console 4 has a function of notifying the determination result in a manner that the photographer can recognize the determination result or a function of outputting the determination result.

In a case where all of the determination conditions (1) to (3) are satisfied, the additional controller 61 or the console 4 permits the generation apparatus to emit radiation.

This configuration makes it possible to reliably prevent imaging in a state in which a selection that does not satisfy the above-mentioned relationship is made.

An operation of setting the irradiation frame rate and the imaging frame rate in an imaging room where there are a combination of imaging apparatuses other than the imaging apparatuses (A) and (C) and a combination of the generation apparatuses (A) and (B) illustrated in FIG. 8A will be described as an example.

First, it is assumed that the radiographer selects the generation apparatus (A) as the generation apparatus to be used, as illustrated in FIG. 9 (the generation apparatus (A) is displayed in a selected generation apparatus display field 43a). The irradiation frame rates corresponding to the generation apparatus (A) (that can perform irradiation) are, for example, three types of 15 frames/s (Hz), 10 frames/s (Hz), and 5 frames/s (Hz).

FIG. 9 illustrates a case where the generation apparatus (A) is selected and only the information of the generation apparatus (A) is displayed in the display field 43a. However, the display field 43a may be configured such that the information of a plurality of generation apparatuses can be displayed in the form of options and the information of the selected generation apparatus (A) may be displayed differently from the information of other generation apparatuses.

Then, the radiographer selects the imaging apparatus 3 to be used. Here, the imaging apparatus (A) and the imaging apparatus (C) can be selected since they include values that are N times (N is an integer equal to or greater than 1) the irradiation frame rates (15, 10, and 5) which can correspond to the generation apparatus (A) selected first among the corresponding imaging frame rates.

Therefore, in a case where the imaging apparatus (A) is selected (a corresponding icon 43b is displayed by a solid line), the selectable imaging frame rate is 15 Hz (that is three times an irradiation frame rate of 5 Hz) from the relationship with a combination of the irradiation frame rates corresponding to the generation apparatus (A).

Among the selectable imaging frame rates, an imaging frame rate with a relatively large (high) value may be selected as a basic imaging frame rate.

In a technique that changes the irradiation frame rate and then performs imaging, if the imaging frame rate is changed in accordance with a change in the irradiation frame rate, an operation that is complicated and takes a lot of time, such as an operation of restarting the imaging apparatus (A) in association with a change in the setting of the imaging apparatus (A), is required. However, the fixation of the imaging frame rate of the imaging apparatus (A) to the basic imaging frame rate makes it possible to eliminate the switching time.

As such, if 15 Hz is selected as the basic imaging frame rate, 15 Hz or 5 Hz that is 1/N times (where N is an integer equal to or greater than 1) the basic imaging frame rate among the irradiation frame rates, to which the generation apparatus (A) can correspond, can be selected as the irradiation frame rate.

If 10 Hz is selected as the irradiation frame rate, the system may be configured such that 10 Hz is not selectable. At this time, for example, as illustrated in FIG. 10, information indicating that the irradiation frame rate is not selectable (information for notifying the determination result: for example, characters 43c of "impossible") may be displayed in the vicinity of the displayed irradiation frame rate.

As another example, as illustrated in FIG. 11, in a case where the imaging apparatus (C) has been selected (a corresponding icon 43d is displayed by a solid line), 10 Hz can be selected as the basic imaging frame rate from the relationship with the corresponding frame rate of the generation apparatus.

In addition, 10 Hz or 5 Hz can be selected as the irradiation frame rate.

It is desirable to set a necessary value to the irradiation frame rate according to an imaging technique. For example, it is desirable to set an irradiation frame rate of at least 2 Hz or more in order to capture the image of the dynamics of a slow change such as breathing.

Therefore, in a case where the set irradiation frame rate is equal to or greater than 2 Hz, the additional controller 61 or the console 4 can be configured to permit the generation apparatus to emit radiation.

Alternatively, the minimum necessary frame rate may be stored for each imaging part or imaging technique. In a case where the irradiation frame rate set according to the selected imaging part or imaging technique is higher than the minimum necessary frame rate, the generation apparatus may be permitted to emit radiation.

Among a plurality of connected imaging apparatuses 3, a recommended imaging apparatus 3 may be automatically selected according to the imaging technique of the radiographer.

Further, in a case where there is no particular change, the imaging apparatus 3 which has been used in the previous imaging may be continuously selected.

If the imaging apparatus 3 to be used is selected, as illustrated in FIG. 5, the console 4 transmits a connection request to the imaging apparatus 3 and the additional apparatus 6 (Step S6).

If the imaging apparatus 3 or the additional apparatus 6 receives the connection request, it is connected to the console 4 (Step S7).

As illustrated in FIG. 5, the connection request may be transmitted from the console 4 to the additional apparatus 6 and may be further transmitted from the additional apparatus 6 to the imaging apparatus 3.

As illustrated in FIG. 2, the imaging apparatus 3 and the console 4 can be connected to each other through the communication network N or can be directly connected to each other. In a case where the console 4 and the imaging apparatus 3 are directly connected to each other, the console 4 is connected to the imaging apparatus 3 that is not connected to the additional apparatus 6 and there is a possibility that a connection configuration will not be established in a state in which the additional apparatus 6 and the imaging apparatus 3 cooperate with each other.

However, this connection between the imaging apparatus 3 and the console 4 through the additional apparatus 6 makes it possible for the console 4 to be reliably connected to the imaging apparatus 3 connected to the additional apparatus 6.

Alternatively, the console 4 may transmit a connection request to each imaging apparatus 3 and then each imaging apparatus 3 may transmit a connection request to the additional apparatus 6, which is not illustrated.

Since the console 4 sets the imaging apparatus 3 to be used for imaging, this configuration makes it possible to reliably select the imaging apparatus 3 to be used, to connect the imaging apparatus 3 and the additional apparatus 6, and to establish a state in which the additional apparatus 6 and the imaging apparatus 3 that is used cooperate with each other, without selecting a wrong imaging apparatus 3.

In addition, this configuration makes it possible to select an imaging apparatus 3 not only from the imaging apparatus 3 connected to the additional apparatus 6 as described above but also from all of the usable imaging apparatuses 3.

When the imaging apparatus 3 starts connection, the imaging apparatus 3 may automatically change its state from the above-mentioned mode in which preparation for imaging or imaging is possible and power consumption is low to a mode in which power consumption is higher than that in the low-power-consumption mode.

Then, if the radiographer sets, for example, imaging conditions with the console 4 and instructs the console 4 to start imaging, the console 4 turns on the sequence start signal that instructs the imaging apparatus 3 and the additional apparatus 6 to start an imaging sequence. Then, the console 4 transmits the sequence start signal to the imaging apparatus 3 and the additional apparatus 6 (Step S8). The sequence start signal can be transmitted using, for example, the information signal which is transmitted and received between the console 4 and the additional apparatus 6 and the information signal which is transmitted and received between the additional apparatus 6 and the imaging apparatus 3.

If the imaging apparatus 3 and the additional apparatus 6 detect that the sequence start signal has been turned on, they start preparation for imaging.

In a case where the additional apparatus 6 is configured to transmit the timing signal in a stage before the irradiation instruction switch 5 is pressed, the additional apparatus 6 may perform control such that the reading instruction signal (see FIG. 22) is turned on and the timing signal is repeatedly transmitted to the imaging apparatus 3 at predetermined intervals after it is detected that the sequence start signal has been turned on (Step S9).

The imaging apparatus 3 repeats the reading operation whenever the timing signal is received. Then, the temperature of the circuit in the imaging apparatus 3 rises. That is, the reading operation which is repeatedly performed by the imaging apparatus 3 in this stage is the warm-up of the imaging apparatus 3.

In the initial stage in which the imaging apparatus 3 repeats the reading operation, the imaging apparatus 3 notifies the console 4 that a warm-up has started (Step S10).

The imaging apparatus 3 needs to perform a reading operation (reset operation) for removing the charge accumulated immediately before imaging.

Since the imaging apparatus 3 consumes power in the reading operation, the temperature of the imaging apparatus 3 rises with an increase in the power consumption. The sensitivity of a light receiver of the imaging device 3 is particularly changed by the temperature rise and image density based on the incident amount of radiation also changes. The change in image density due to the temperature rise is not a problem in a case where one still image is captured. However, in a case where dynamic imaging (for repeatedly capturing still images) is performed as in the system 100 according to this embodiment, the change in image density due to the temperature rise during imaging becomes a problem.

However, the above-mentioned configuration in which the imaging apparatus performs a warm-up makes it possible to reduce the change in image density due to the temperature rise.

The imaging apparatus 3 may acquire a correction image at any timing when Step S9 is repeated a plurality of times.

For example, in a case where the imaging apparatus 3 is configured to perform a warm-up (to perform the reading operation before the irradiation instruction switch 5 is pressed), the imaging apparatus 3 may transmit an image which has been read in the second half of the warm-up as the correction image to the console 4 (Step S11).

A plurality of pixels of the imaging apparatus 3 have different characteristics and the charge levels corresponding to the brightness of the image are different in the pixels even when radiation is not emitted. Therefore, the image read in the second half of the warm-up is acquired as the correction image and, for example, each signal value of the correction image is subtracted from each signal value of a captured image which is obtained later to obtain a captured image in which a variation for each pixel has been removed.

In this embodiment, a case where the correction image is simply subtracted from the captured image has been described as an example of the method of using the correction image. However, noise components may be removed using various operations.

When the read operation (reset operation) for removing the charge accumulated immediately before imaging other than the acquisition of the correction image is performed, at least one of the following processes may be performed as the same operation as that in normal imaging:

a process of converting the removed charge into an image;

a process of storing the image data of the obtained image in the storage of the imaging apparatus 3; and a process of transmitting the imaged data or the image data stored in the storage of the imaging apparatus 3 to the console 4.

The above-mentioned process which is the same as that in normal imaging is performed under the conditions close to those of actual imaging Therefore, according to this configuration, a difference in imaging in the subsequent steps is small and it is possible to reduce, for example, the influence of the temperature rise.

In contrast, in a case where the above-mentioned process which is the same as that in normal imaging is performed, the following problems arise:

the amount of power consumption increases;

since an unnecessary image obtained while no radiation is emitted is stored in the storage of the imaging apparatus 3, the capacity of the storage that can be used at the time of imaging is reduced;

since the unnecessary image obtained while no radiation is emitted is transmitted to the console, the transmission of the unnecessary image occupies a part of communication capacity; and since the unnecessary image is stored in the storage of the console, the capacity of the storage that can be used at the time of imaging is reduced.

Therefore, some of the processes may be omitted in order to avoid the problems.

The imaging apparatus 3 can be configured to complete the warm-up in a case where the number of reading operations as the warm-up reaches a predetermined value or the reading operation period has elapsed. For example, in Step S25 (see FIG. 12) in which the irradiation start signal is turned on, which will be described below, control is performed such that the irradiation start signal is not turned on until the number of reading operations reaches a predetermined value or the reading operation period elapses, which makes it possible not to start imaging using the emission of radiation until the warm-up is completed.

Then, the imaging apparatus 3 notifies the console 4 that preparation for imaging has been completed (Step S12).

At that time, "Imaging is available" may be displayed on the display 43 of the console 4 (Step S13).

C: Imaging Check

The additional apparatus 6 continues to repeatedly transmit the timing signal to the imaging apparatus 3 and the imaging apparatus 3 repeats the reading operation whenever the timing signal is received.

If the radiographer ends the positioning of the subject and presses the irradiation instruction switch 5 to the first stage (Step S14), the irradiation instruction switch 5 turns on the irradiation preparation signal output to the radiation controller 11 through the console 4 (Step S15).

If the radiation controller 11 of the generation apparatus detects that the irradiation preparation signal has been turned on, it turns on the irradiation preparation signal output to the high voltage generator 12 and the additional apparatus 6 (Step S16). Then, the first acquirer 62 of the additional apparatus 6 acquires the irradiation preparation signal (which is output before the irradiation instruction signal and after the sequence start signal is turned on).

As such, the generation apparatus including the radiation controller 11 starts preparation for the emission of radiation in response to the irradiation preparation signal.

If the additional controller 61 of the additional apparatus 6 detects that the irradiation preparation signal from the radiation controller 11 has been turned on, it transmits the imaging preparation signal to the console 4 (Step S17).

In this case, the additional controller 61 or the console 4 may check again the following determination conditions (1) to (3).

(1) The set irradiation frame rate is a value corresponding to the generation apparatus.

(2) The set imaging frame rate is a value corresponding to the imaging apparatus 3.

(3) The ratio of the irradiation frame rate to the imaging frame rate is 1:N, where N is an integer equal to or greater than 1 (the imaging frame rate is N times the irradiation frame rate).

If the above-mentioned relationship is not satisfied, the console 4 may prohibit an advance to the subsequent sequence or may not permit imaging.

The system may be configured to notify the radiographer of an error to warn the radiographer that the above-mentioned relationship is not satisfied when the above-described measures are taken.

If the console 4 receives the imaging preparation signal, it starts preparation for imaging. The preparation for imaging in the console 4 is, for example, an operation of checking whether the settings of the imaging apparatus control console 42 and the settings of the radiation control console 41 that controls the emission of radiation in the console 4 are the same or an operation of checking whether the designated imaging conditions are set in the imaging apparatus 3.

If preparation for imaging is completed, the console 4 turns on the imaging preparation completion signal output to the additional apparatus 6 (Step S18).

At that time, "Imaging is being performed" may be displayed on the display 43 of the console 4 (Step S19).

In the stage in which the preparation for imaging has been completed, for example, the input of an instruction to change the imaging conditions to the console 4 may be locked such that the imaging conditions are not changed.

In a case where a still image is captured, imaging ends in a short time. Therefore, the risk of changing the imaging conditions during imaging is low and there is little need for this configuration. However, in the case of dynamic imaging, since the imaging period is long, there is a high risk that the radiographer or a third party other than the radiographer will intentionally or unintentionally operate the console screen to change the imaging conditions.

For this reason, in the process from this stage to the end of the sequence after Step S45 which will be described below, the input of, for example, an instruction to change the imaging conditions to the console 4 is locked, which makes it possible to reliably prevent the change in the imaging conditions.

FIG. 5 illustrates a case where the imaging preparation signal is output from the additional apparatus 6 to the console 4. However, in some cases, the imaging preparation signal is not output to the console 4, but is output to the imaging apparatus 3 such that the imaging apparatus 3 prepares imaging and the imaging preparation completion signal is output from the imaging apparatus 3 to the additional apparatus 6 after the imaging apparatus 3 completes preparation for imaging.

Further, in some cases, the imaging preparation signal is input to both the console 4 and the imaging apparatus 3 such that both the console 4 and the imaging apparatus 3 prepare imaging and the imaging preparation completion signal is output from the console 4 and the imaging apparatus 3 to the additional apparatus 6 after both the console 4 and the imaging apparatus 3 complete preparation for imaging. Then, it is determined that the entire preparation for imaging has been completed in a stage in which the additional apparatus 6 has received the imaging preparation completion signal from both the console 4 and the imaging apparatus 3.

In a case where the radiation controller 11 of the generation apparatus has a connector that can input the imaging preparation completion signal indicating that preparation for imaging in the external device has been completed, the additional apparatus 6 may output the imaging preparation completion signal to the radiation controller 11, which is not illustrated.

The radiation controller 11 detects that the imaging preparation completion signal from the additional apparatus 6 has been turned on to detect that the imaging apparatus 3 is in a state in which it can perform imaging Since the radiation control device 1 performs control such that radiation is emitted after it is detected that the imaging preparation completion signal has been turned on, it is possible to surely eliminate the risk that the imaging apparatus 3 will emit radiation while imaging is not possible and the subject will be unnecessarily exposed to radiation.

D: Execution of Imaging

Then, in a case where the radiographer presses the irradiation instruction switch 5 to the second stage (Step S20), the irradiation instruction switch 5 turns on the irradiation instruction signal transmitted to the radiation controller 11 through the console 4 (Step S21).

In this case, the additional apparatus 6 continues to repeatedly transmit the timing signal to the imaging apparatus 3 and the imaging apparatus 3 repeats the reading operation whenever the timing signal is received.

Even in a case where the irradiation instruction signal is input from the irradiation instruction switch 5, the radiation controller 11 of the generation apparatus does not transmit the irradiation signal to the high voltage generator 12 since the irradiation permission signal from the additional apparatus 6 is in an off state at this time.

The radiation controller 11 turns on the irradiation instruction signal transmitted to the additional controller 61 (Step S22).

If the additional apparatus 6 receives the irradiation instruction signal, it turns on the imaging start signal which notifies whether to permit the start of imaging and is output to the imaging apparatus 3 and the console 4 (Steps S23 and S24).

In this case, the additional controller 61 or the console 4 may check again the following determination conditions (1) to (3).

(1) The set irradiation frame rate is a value corresponding to the generation apparatus.

(2) The set imaging frame rate is a value corresponding to the imaging apparatus 3.

(3) The ratio of the irradiation frame rate to the imaging frame rate is 1:N, where N is an integer equal to or greater than 1 (the imaging frame rate is N times the irradiation frame rate).

If the above-mentioned relationship is not satisfied, the console 4 may prohibit an advance to the subsequent sequence or may not permit imaging.

The system may be configured to notify the radiographer of an error to warn the radiographer that the above-mentioned relationship is not satisfied when the above-described measures are taken.

If it is detected that the imaging start signal has been turned on, for example, the imaging apparatus 3 turns on the irradiation start signal output to the additional apparatus 6, using the end of its reading operation performed at that time as a trigger, as illustrated in FIG. 12 (Step S25). The reason is as follows. The reading operation of the imaging apparatus 3 sequentially reads the charge accumulated in the pixels which are two-dimensionally arranged to acquire the image of the entire light receiving surface. If the irradiation start signal is turned on to emit radiation during the reading operation, there is a difference between the signal value of the pixel from which the reading of charge has been completed and the signal value of the pixel from which the reading of charge has not been completed. As a result, image quality is significantly degraded.

In contrast, in this embodiment, the emission of radiation and the image reading operation of the imaging apparatus 3 are performed on the basis of the irradiation permission signal and the timing signal from the additional apparatus 6, which will be described below. Therefore, the emission of radiation during the reading operation does not occur in a normal routine. Thus, the irradiation start signal may be turned on, without considering the reading timing of the imaging apparatus 3.

The imaging apparatus 3 repeats the image reading operation even after the irradiation start signal is turned on. The image read after the irradiation start signal is turned on is stored as the captured image in the memory of the imaging apparatus 3 or is transmitted to the console 4.

If the additional apparatus 6 detects that the irradiation start signal from the imaging apparatus 3 has been turned on, it detects that the imaging apparatus 3 is in a state in which the imaging apparatus 3 can perform imaging and repeatedly transmits the irradiation permission signal to the radiation controller 11 (Step S26).

In a case where the irradiation frame rate and the imaging frame rate are set such that the ratio of the irradiation frame rate to the imaging frame rate is 1:N, the additional controller 61 outputs the imaging permission signal once whenever it transmits the timing signal N times (FIG. 12 illustrates a case where N is 2).

The radiation controller 11 of the generation apparatus repeatedly transmits the irradiation signal to the high voltage generator 12 since the imaging instruction signal and the irradiation permission signal are aligned whenever the irradiation permission signal is received.

Whenever the irradiation signal is received, the high voltage generator 12 repeatedly generates a high voltage required for emitting radiation and repeatedly outputs the high voltage as an irradiation output to the radiation generator 2.

The radiation generator 2 repeatedly emits radiation to the imaging apparatus 3 whenever the irradiation output is input (Step S27).

The emitted radiation is transmitted through the subject (not illustrated) disposed between the imaging apparatus 3 and the radiation generator 2 and is then incident on the imaging apparatus 3.

Whenever the timing signal is received, the imaging apparatus 3 repeats a process of accumulating the amount of charge corresponding to the intensity of the incident radiation (Step S28) and reading the charge as a captured image (Step S29).

The imaging apparatus 3 continuously repeats accumulation and reading. Whenever accumulation and reading are repeated N times, the imaging apparatus 3 is irradiated with radiation from the generation apparatus once and generates an exposed image.

The imaging apparatus 3 transmits the read radiographic image to the console 4 (Step S30).

In a case where the captured image is configured to be transmitted to the console 4 and is not transmitted to the console 4 in time due to the amount of data or a communication environment, some of a plurality of captured images or a part of one captured image may be stored in the imaging apparatus 3 and the rest may be transmitted to the console 4.

An example of the operation of the imaging apparatus 3 will be further described. Here, a case where the accumulation of charge starts in response to the timing signal will be described.

Reset Operation/Correction Image Acquisition Operation

In the reset operation performed before imaging, the imaging apparatus 3 can repeat the above-mentioned operation while there is no radiation emitted from the radiation generation apparatus to output the charge (a dark charge or a dark current) which has been accumulated in each pixel and is not based on the emission of radiation, thereby resetting the charge which has been accumulated in each pixel, is not based on the emission of radiation, and is a noise component with respect to the image obtained by the charge based on the emission of radiation. Further, in the reset operation, control may be performed which the reader 34 does not convert the input charge into image data (operation before t1).

In the correction image acquisition operation performed before or after imaging, the imaging device 3 can repeat the above-mentioned operation while there is no radiation emitted from the radiation generation apparatus to output the charge (a dark charge or a dark current) which has been accumulated in each pixel and is not based on the emission of radiation, thereby resetting the charge which has been accumulated in each pixel, is not based on the emission of radiation, and is a noise component with respect to the image obtained by the charge based on the emission of radiation. In the correction image acquisition operation, the reader 34 converts the input charge into image data and the image data is stored. Therefore, it is possible to store a noise component while radiation is not emitted and to remove the noise component by subtracting the noise component from the image data obtained while radiation is emitted. The correction image acquisition operation may be performed as a part of the reset operation (operation before t1).

Operation of Ending Reset Operation/Correction Image Acquisition Operation

If the irradiation instruction signal in Step S21 is turned on following the reset operation or the correction image acquisition operation, the imaging start signal input to the imaging apparatus 3 is turned on (Step S23). Then, the imaging apparatus 3 stops the reset operation or the correction image acquisition operation.

In a case where the correction image acquisition operation has not completed the acquisition of a predetermined number of correction images even though the imaging start signal has been turned on, the correction image acquisition operation is not stopped and is continuously performed until a predetermined number of correction images are acquired. Then, the correction image acquisition operation is stopped.

If the reset operation or the correction image acquisition operation is stopped, the imaging apparatus 3 stops the reset operation or the correction image acquisition operation and turns on the irradiation start signal in Step S25 to notify that the imaging apparatus 3 is in a state in which it can perform imaging (t1).

Operation

If the imaging apparatus 3 receives the timing signal from the additional controller 61, it applies the off-voltage to each scanning line 32*b* and changes to a state in which the charge generated by the radiation detection element 32*d* can be accumulated in the pixel, as illustrated in FIG. 14 (t2, t6, t10, . . . ).

The additional controller 61 outputs the irradiation permission signal at the timing that is operatively associated with the timing when the timing signal is transmitted. The radiation generation apparatus irradiates the imaging apparatus 3 with radiation in response to the irradiation permission signal (Step S27; t3, t7, t11, . . . ).

In a case where the irradiation frame rate is 1/N times the imaging frame rate (FIG. 14 illustrates a case where N is 2), the additional controller 61 outputs the irradiation permission signal once whenever it repeatedly outputs the timing signal N times. As a result, whenever the imaging apparatus 3 repeats accumulation and reading N times in response to the timing signal and the irradiation permission signal, the radiation generation apparatus emits radiation once (Step S27; t3, t11, . . . ). At that time, radiation is not emitted at the other timings (t7, . . . ).

The imaging apparatus 3 continues the mode for accumulating charge for a predetermined period of time, using a timer provided in the imaging apparatus 3 (t2 to t4, t6 to t8, t10 to t12, . . . ).

If the imaging apparatus 3 receives radiation in the mode for accumulating charge, each radiation detection element 32d of the radiation detector 32 generates charge and the charge is accommodated in each pixel (Step S28).

Then, the imaging apparatus 3 performs the reading operation which applies the on-voltage to each switching element 32e after the predetermined period of time elapses using the timer provided in the imaging apparatus 3 to output the charge accumulated in each pixel to the signal line 32c. In the reading operation of the imaging apparatus 3, the reader 34 reads the input charge and converts the charge into image data. In addition, the imaging apparatus 3 transmits at least a part of the image data to the console 4 (Steps S29 and S30; t4 to t5, t8 to t9, t12 to t13, . . . ).

Another Embodiment of Operation Control Method

The example in which the imaging apparatus changes to a state in which it can accumulate charge in the pixels in response to the timing signal from the additional controller 61 has been described above. However, control may be performed such that the imaging apparatus performs other operations in response to the timing signal.

For example, another control method may perform control such that, after the imaging apparatus 3 ends the reading operation (t4 to 5, t8 to t9, t12 to t13, . . . ) of discharging the charge accumulated in each pixel to the signal line 32c, the imaging apparatus 3 changes to a state (t6 to t8, t10 to t12, . . . ) in which it can accumulate charge in the pixels, without waiting for the timing signal from the additional controller 61.

Then, the additional controller 61 performs control such that the timing signal is output at the timing which is operatively associated with the timing when the radiation generation apparatus transmits the irradiation permission signal for radiation emission control.

The imaging apparatus 3 changes to the reading operation that outputs the charge accumulated in each pixel to the signal line 32c in response to the received timing signal (t4, t8, t12, . . . ).

The repetition of the above-mentioned operation control makes it possible to perform imaging while matching the radiation emission timing of the radiation generation apparatus and the image generation timing of the imaging apparatus.

E: End of Imaging

The additional apparatus 6 counts the number of times the irradiation permission signal is transmitted from the time when the emission of radiation starts and determines whether the number of captured images reaches a predetermined maximum value whenever the number of times the irradiation permission signal is transmitted is counted. If it is determined that the counted number of times the irradiation permission signal is transmitted (the number of captured images) reaches the maximum number of captured images, the additional apparatus 6 turns off the imaging start signal (Step S31) and stops the output of the timing signal or/and the irradiation permission signal, as illustrated in FIG. 13.

Control may be performed such that the imaging apparatus 3 performs the operation of accumulating the amount of charge corresponding to the intensity of the incident radiation (Step S28) and reading the charge as a captured image (Step S29) at least once after the additional apparatus 6 outputs the irradiation permission signal last. In this case, it is possible to reliably read the image obtained by the last emission of radiation, to use the read image as the captured image, and to reliably prevent the subject from being unnecessarily exposed to radiation.

In addition, control may be performed such that the imaging apparatus 3 performs the operation of accumulating charge (Step S28) and reading the charge as a captured image (Step S29) after the additional apparatus 6 outputs the irradiation permission signal last, and then performs the operation of accumulating charge and reading the charge as a captured image. Since the captured image is an image captured while no radiation is emitted, these images can be used to correct the images captured in a case where radiation is emitted, similarly to the correction image.

In other words, for the correction image, an image captured before imaging using radiation as described above may be used as the correction image or an image captured after imaging using radiation as described above may be used as the correction image.

Alternatively, the correction images captured before and after imaging using radiation may be used. In this case, the correction images captured before and after imaging using radiation may be used to predict a change in the correction image during imaging and the correction image may be generated on the basis of the prediction result. The correction image can be generated, for example, by averaging the correction images captured before and after radiography or by performing linear or curve compensation for fluctuations.

In a case where a still image is captured, since the time required for imaging is short, a change in the correction images before and after imaging is small. However, in the case of dynamic imaging, the time required for imaging is longer than that in a case where a still image is captured. Therefore, in a case where the correction images before and after imaging are used as described above, it is possible to perform correction, also considering fluctuations during imaging.

The number of captured images may not be counted on the basis of the number of times the irradiation permission signal is transmitted as described above, but may be counted on the basis of the number of times the timing signal is output after the start of imaging.

In addition, the number of captured images may not be counted on the basis of the number of times the irradiation permission signal is transmitted as described above, but may be counted on the basis of the time elapsed since the start of imaging.

If it is detected that the imaging start signal has been turned off and imaging after radiation is emitted or imaging for acquiring the correction image ends, the imaging apparatus 3 turns off the reading instruction signal (see FIG. 22) and transmits the images remaining in the memory of the imaging apparatus 3 (the captured images which have not been transmitted) to the console 4 (Step S32). Then, when the transmission of the remaining images is completed, the imaging apparatus 3 transmits the remaining image transmission completion signal to the console 4 (Step S33).

If the console 4 detects that the imaging start signal has been turned off, it starts an operation of checking the transmitted captured image.

If the console 4 receives the remaining image transmission completion signal, it transmits an image deletion signal for instructing the deletion of an image to the imaging apparatus 3 (Step S34).

Control may be performed such that the image deletion signal is transmitted after the captured image check operation is completed and it is checked that there is no problem in all of the transmitted images.

At that time, "End of imaging" may be displayed on the display 43 of the console 4 (Step S35).

If the imaging apparatus 3 receives the image deletion signal, it deletes the captured images stored in the memory (Step S36). Therefore, the free space of the memory can be ensured for the next imaging.

If the radiographer who has checked the end of imaging (for example, who has seen "End of imaging" displayed on the console 4) releases the second stage of the irradiation instruction switch 5 (Step S37), the irradiation instruction switch 5 turns off the irradiation instruction signal (Step S38) and the radiation controller 11 also turns off the irradiation instruction signal (Step S39).

Then, if the radiographer releases the first stage of the irradiation instruction switch 5 (Step S40), the irradiation instruction switch 5 turns off the irradiation preparation signal (Step S41) and the radiation controller 11 also turns off the irradiation preparation signal (Step S42).

If the additional apparatus 6 detects that the irradiation preparation signal has been turned off, it notifies the console 4 that the irradiation preparation signal has been turned off.

If the console 4 receives the notification from the additional apparatus 6, it turns off the imaging preparation completion signal and changes a sequence state to an irradiation preparation state.

If the additional apparatus 6 detects that the irradiation instruction signal and the irradiation preparation signal have been turned off, it transmits an imaging end signal indicating that imaging has ended to the imaging apparatus 3 and the console 4 (Steps S43 and S44).

If the imaging apparatus 3 receives the imaging end signal, it transmits a standby signal to the console 4 (Step S45).

If the console 4 receives the standby signal, it monitors the presence and absence of re-imaging or another imaging is performed for a predetermined period. If there is no re-imaging or another imaging for a predetermined period, the console 4 turns off the sequence start signal to change the sequence state to a standby state in which it waits for an imaging instruction.

In this way, a series of imaging operations ends.

The system 100 according to this embodiment operates as described above and dynamic imaging that repeatedly captures a plurality of still images in a short time is performed.

Selection of Image after Imaging

Then, the console 4 extracts only exposed images from a plurality of frames including every N exposed images which form the obtained dynamic image and have been captured at the timing when radiation is emitted (N−1 unexposed images generated without emitting radiation are interposed between the exposed images) and uses the extracted exposed images as a new dynamic image, which makes it possible to obtain a dynamic image with a radiation exposure of 1/N.

The extraction of the exposed image may be performed on the basis of the set irradiation frame rate, the imaging frame rate, and the frame number assigned to the dynamic image or may be performed by determining the pixel value of a predetermined pixel of each frame.

When the exposed image is extracted, an image correction process may be performed for the exposed image, using an unexposed image generated at the timing other than the timing when the exposed image is generated, if necessary.

Effect

In radiography systems that include a radiation generation apparatus capable of generating radiation and a radiography apparatus capable of generating a radiographic image based on the received radiation and can capture a dynamic image having a series of radiographic images as each frame, in recent years, a radiography system has been proposed which can perform imaging while switching the frame rate to a desired frame rate among a plurality of different frame rates.

For example, JP 2005-287773 A discloses a technique in which, while a radiography apparatus repeats charge accumulation and reading a predetermined number of times, a radiation generation apparatus emits radiation a number of times that is less than a predetermined value (thins out some of the radiation) such that the frame rate is less than usual and imaging is performed in this state. In addition, JP 2005-287773 A discloses a technique in which a controller controls the emission of radiation, accumulation, and reading and a thinned-out image generated at the timing when radiation is not emitted is used for correction.

Some radiography systems can use a plurality of cassette-type radiography apparatuses according to various situations. In these systems, in a case where the frame rate is switched according to the situation as in JP 2005-287773 A, for example, there is a problem that it is difficult to perform imaging since the frame rate designated by the radiographer does not correspond to at least one of the radiography apparatus and the radiation generation apparatus to be used, which does not occur in a case where imaging is performed with a fluoroscopic apparatus in which a combination of a radiation generation apparatus and an imaging apparatus is fixed.

In particular, in a situation in which the frame rate designated by the radiographer corresponds to the radiation generation apparatus, but does not correspond to the radiography apparatus, even though the radiation generation apparatus emits radiation in imaging, the radiography apparatus is not capable of performing accumulation and reading at that timing. Therefore, there is a risk that the subject will be unnecessarily exposed to radiation.

That is, in the imaging in which, while the radiography apparatus repeats charge accumulation and reading a predetermined number of times, the radiation generation apparatus emits radiation a number of times that is less than a predetermined value, it is necessary to reliably prevent the risk of starting imaging in a state in which the frame rate that does not correspond to at least one of the radiography apparatus and the radiation generation apparatus is set.

In order to solve the problems, in the system 100 according to the second embodiment, the additional controller 61 is connected to the radiation control device 1 which can perform the emission of radiation only once in response to one radiation emission instruction in the conventional system 100A illustrated in FIG. 1 such that the radiation control device 1 can output an irradiation signal a plurality of times in response to one irradiation instruction signal acquisition (turn-on detection) operation. That is, the generation apparatus can repeatedly generate radiation with a predetermined period. Therefore, it is possible to perform imaging which repeatedly generates a frame based on the received radiation with a predetermined period using the imaging apparatus 3, that is, dynamic imaging.

The conventional system 100A illustrated in FIG. 1 is widely used as a system that can capture a simple still image. Therefore, a medical institution using the conventional system 100A can easily modify the conventional system 100A including the existing generation apparatus so as to respond to the dynamic imaging only by adding the imaging apparatus 3 and the additional apparatus 6, without updating the expensive generation apparatus.

The system 100 according to this embodiment notifies the radiographer of the result of determining whether the irradiation frame rate acquired by the additional controller 61 or the console 4 is N times the acquired imaging frame rate (where N is an integer equal to or greater than 1) in a manner that the radiographer can recognize the determination result. Therefore, in the imaging in which, while the imaging apparatus 3 repeats charge accumulation and reading a predetermined number of times, the generation apparatus emits radiation a number of times that is equal to or less than a predetermined value, it is necessary to reliably prevent the risk of starting imaging in a state in which the frame rate that does not correspond to at least one of the imaging apparatus 3 and the generation apparatus is set.

Modification Example 1

The example in which all of the captured images are transmitted from the imaging apparatus 3 to the console 4 and the console 4 extracts necessary images (exposed images) and generates a dynamic image has been described above. However, all of the captured images may not be transmitted to the console 4 and the imaging apparatus 3 selects an exposed image or an unexposed image generated at other timings and transmits the selected image to the console 4. In addition, the imaging apparatus 3 may perform an image correction process for the exposed image if necessary.

Modification Example 2: Imaging Apparatus 3 Counts Number of Captured Images

In the above-described embodiments, the example in which the additional apparatus 6 counts the number of times the irradiation permission signal is transmitted and determines that the number of images reaches the maximum value when the counted number of times the irradiation permission signal is transmitted reaches the maximum number of captured images has been described. However, an apparatus configuration may be used which counts the number of times the imaging apparatus 3 receives the timing signal after the irradiation start signal is transmitted, the number of times the imaging apparatus 3 receives the timing signal and performs reading, the number of times the imaging apparatus 3 performs reading and stores an image, or the number of times the image is transmitted to the console 4 and determines whether the counted number of times reaches the maximum number of captured images.

Modification Example 3: Permission of Imaging According to State of Imaging Apparatus When the imaging apparatus 3, the console 4, and the additional apparatus 6 are connected or when imaging starts, it may be determined whether the designated dynamic imaging can be performed until the end with reference to the remaining power or remaining memory capacity of the imaging apparatus 3.

If the imaging is possible on the basis of the determination result, information indicating that the imaging is possible may be displayed.

If the imaging is not possible on the basis of the determination result, information indicating that the imaging is not possible may be displayed.

Modification Example 4: Operation of Radiation Controller in Dynamic Imaging

In the above-described embodiments, the radiation controller 11 receives the irradiation instruction signal from the irradiation instruction switch 5 and repeatedly receives the irradiation permission signal from the additional controller 61.

For example, the irradiation permission signal is transmitted as a pulse signal corresponding to the emission of radiation for capturing each frame of a dynamic image to the radiation controller 11. Then, the radiation controller 11 transmits the irradiation signal to the high voltage generator 12 in response to each of the repeatedly received irradiation permission signals on a one-to-one basis such that radiation is emitted.

In a case where one still image is captured, it is sufficient for the radiation controller 11 to perform one irradiation permission signal transmission operation in response to one irradiation instruction signal reception operation.

In order to capture a still image, even if the irradiation permission signal is received a plurality of times in response to one irradiation instruction signal, radiation should not be emitted a plurality of times. Therefore, the radiation controller 11 may be configured to transmit the irradiation signal only once in response to the first input of the irradiation permission signal even if the irradiation permission signal is received a plurality of times in response to one irradiation instruction signal.

However, in a case where the radiation controller 11 transmits the irradiation signal only once in response to one irradiation permission signal as described above, it is difficult to perform dynamic imaging by repeatedly emitting radiation a plurality of times in response to one irradiation instruction signal as in the system 100 according to this embodiment.

Therefore, the radiation controller 11 may be configured to transmit the irradiation signal a plurality of times to the high voltage generator 12 in a case where the irradiation permission signal is received a plurality of times for one irradiation instruction signal input period, for which the radiographer presses the irradiation instruction switch 5.

In this case, the emission of radiation is repeatedly performed a plurality of times in response to one irradiation instruction signal to perform dynamic imaging.

The control mode (1) in which the irradiation signal is transmitted only once in response to one irradiation permission signal and the control mode (2) in which the irradiation signal is transmitted to the high voltage generator 12 a plurality of times in response to the input of the irradiation permission signal in a case where the irradiation permission signal is input a plurality of times for the irradiation instruction signal input period may be switched according to the type of imaging (whether imaging is the capture of a still image or dynamic imaging).

The console 4 can switch the control mode of the radiation controller 11 according to the type of imaging. Alternatively, the control mode may be changed on the basis of the reception of a signal indicating the type of imaging from the console 4.

This configuration makes it possible to reliably prevent the risk that radiation will be erroneously emitted a plurality of times when a still image is captured and the subject will be unnecessarily exposed to radiation.

Modification Example 5: Limit of Timing of Radiation Controller in Dynamic Imaging For example, in a case where electrical noise is mixed in the irradiation permission signal transmitted from the additional controller 61 to the radiation controller 11 and the radiation controller 11 receives the same signal as the irradiation permission signal at an unintended timing, the same situation as that in which the irradiation permission signal is repeatedly received at intervals that are so short that the high voltage generator 12 does not generate the high voltage required for emitting radiation in time is likely to occur. If the radiation controller 11 forcibly transmits the irradiation signal to the high voltage generator 12, it is likely that an excessive current will flow through the high voltage generator 12 and the high voltage generator 12 will be out of order.

In the above-described embodiments, the radiation controller 11 may be configured as follows: in a case where the irradiation permission signal is repeatedly received from the additional controller 61 while the irradiation instruction signal input from the irradiation instruction switch 5 is in an on state, the radiation controller 11 compares the length of the reception interval of two consecutive irradiation permission signals with a predetermined minimum reception interval and does not transmits the irradiation signal to the high voltage generator 12 in a case where it is determined that the reception interval is shorter than the minimum reception interval.

This configuration makes it possible to prevent the high voltage generator 12 from being out of order due to the flow of an excessive current to the high voltage generator 12.

Conventional Technology 2

Conventional Technology 2 which is the basis of systems 200 (will be described in detail below) according to third and fourth embodiments of the invention will be described with reference to FIG. 15. The same configurations as those in Conventional Technology 1 are denoted by the same reference numerals and the description thereof will not be repeated.

System Configuration

First, the schematic configuration of a radiography system (hereinafter, referred to as a conventional system 200A) according to Conventional Technology 2 will be described. FIG. 15 is a block diagram illustrating the schematic configuration of the conventional system 200A.

Figure 15:
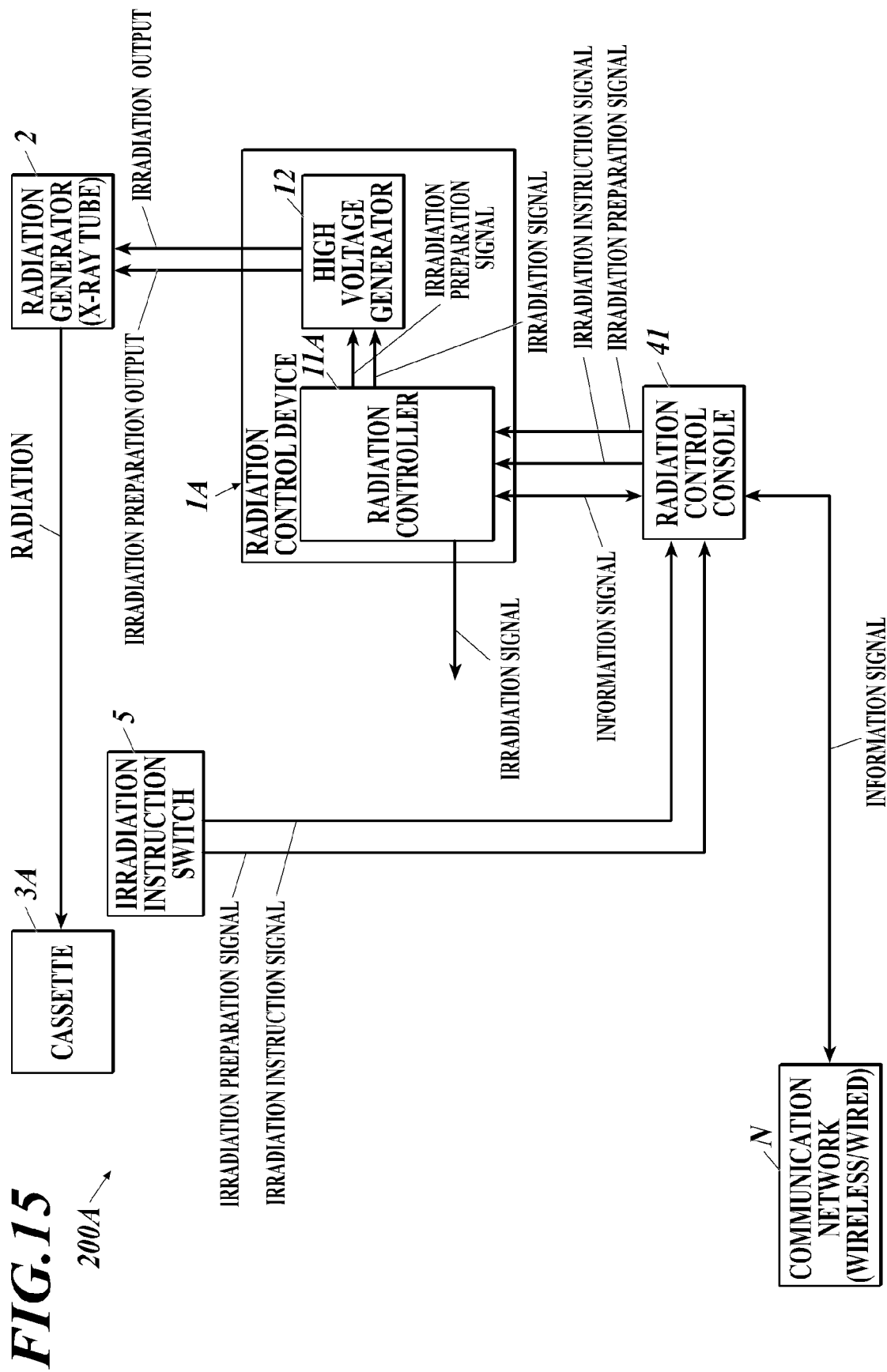
FIG. 15 is a block diagram illustrating a radiography system according to Conventional Technology 2.

For example, as illustrated in FIG. 15, the conventional system 200A differs from the conventional system 100A in the configuration of a radiation controller 11A of a radiation control device 1A.

Specifically, the radiation controller 11 of the conventional system 100A is configured to output the irradiation preparation signal and the irradiation instruction signal from the radiation control console 41 to an external apparatus on the basis of the detection of the turn-on of the irradiation preparation signal or the irradiation instruction signal. However, the radiation controller 11A of the conventional system 200A does not have this configuration.

In addition, the radiation controller 11 of the conventional system 100A is configured to receive the irradiation permission signal from the external apparatus. However, the radiation controller 11A of the conventional system 200A does not have this configuration.

Operation

The operation of the conventional system 200A will be described.

Irradiation Preparation Operation

If the radiographer presses the irradiation instruction switch 5 to the first stage, the irradiation instruction switch 5 turns on the irradiation preparation signal output to the radiation controller 11A through the radiation control console 41.

If it is detected that the irradiation preparation signal has been turned on, the radiation controller 11A turns on the irradiation preparation signal output to the high voltage generator 12.

FIG. 15 does not illustrate the output of the irradiation preparation signal from the radiation controller 11A to an external apparatus. However, in a case where the radiation controller 11A cooperates with the external apparatus, it may output the irradiation preparation signal to the external apparatus.

If the high voltage generator 12 detects that the irradiation preparation signal has been turned on, it outputs the irradiation preparation output to the radiation generator 2.

If the irradiation preparation output is input, the radiation generator 2 starts preparation for generating radiation.

In a case where an anode is a rotating anode, for example, an operation of rotating the rotating anode is performed.

Irradiation Operation

Then, if the radiographer presses the irradiation instruction switch to the second stage, the irradiation instruction switch 5 turns on the irradiation instruction signal output to the radiation controller 11A through the radiation control console 41.

FIG. 15 does not illustrate the output of the irradiation instruction signal from the radiation controller 11A to the external apparatus. However, in a case where the radiation controller 11A cooperates with the external apparatus, it may output the irradiation instruction signal to the external apparatus.

In Conventional Technology 2, since the irradiation permission signal is not received from the external apparatus, the control process of transmitting the irradiation signal in a case where the irradiation instruction signal is aligned with the irradiation permission signal is not performed. Therefore, the radiation controller 11A transmits the irradiation signal to the high voltage generator 12 on the basis of only the detection of the turn-on of the irradiation instruction signal.

If the high voltage generator 12 receives the irradiation signal, it applies a high voltage required for the radiation generator 2 to emit radiation as an irradiation output to the radiation generator 2.

If the high voltage generator 12 applies the high voltage, the radiation generator 2 generates radiation corresponding to the applied voltage.

For example, the irradiation direction, irradiation region, and quality of the generated radiation are adjusted by a controller (not illustrated), such as a collimator, and the adjusted radiation is emitted to the subject and the cassette 3A behind the subject. A portion of the radiation passes through the subject and is then incident on the cassette 3A.

If the radiation is incident on the cassette 3A, a radiographic image is formed on a film or a fluorescent plate provided in the cassette 3A.

Similarly to Conventional Technique 1, the radiation controller 11A may be configured not to transmit the irradiation signal until a predetermined standby time elapses from the detection of the turn-on of the irradiation preparation signal even if the turn-on of the irradiation instruction signal has been detected, in order to prevent radiation from being emitted before the rotating anode reaches a sufficient rotation speed.

As such, in radiography using the conventional system 200A, only one radiographic image (still image) of the subject is captured on the basis of one imaging operation, similarly to a case where the conventional system 100A is used.

Third Embodiment

The third embodiment of the invention will be described with reference to FIGS. 16 to 18. The same configurations as those in the first and second embodiments are denoted by the same reference numerals and the description thereof will not be repeated. In addition, various modification patterns described in the first and second embodiments may also be applied to this embodiment.

Premise, Background, and Task

There is a radiography system including the radiation controller 11 illustrated in Conventional Technology 1 which has an input port for the irradiation permission signal from the outside and transmits the irradiation signal according to the irradiation instruction from the radiographer and the irradiation permission from the outside. In addition, there is a radiography system including the radiation controller 11A illustrated in Conventional Technology 2 which has only an input port for the irradiation instruction signal from the outside and captures a still image.

A radiography system (hereinafter, referred to as a system 200) according to this embodiment is configured such that an additional apparatus 6A is added to the radiation controller 11A to continuously perform imaging System Configuration First, the system configuration of the radiography system 200 will be described. FIG. 16 is a block diagram illustrating the schematic configuration of the system 200 according to the third embodiment.

Figure 16:
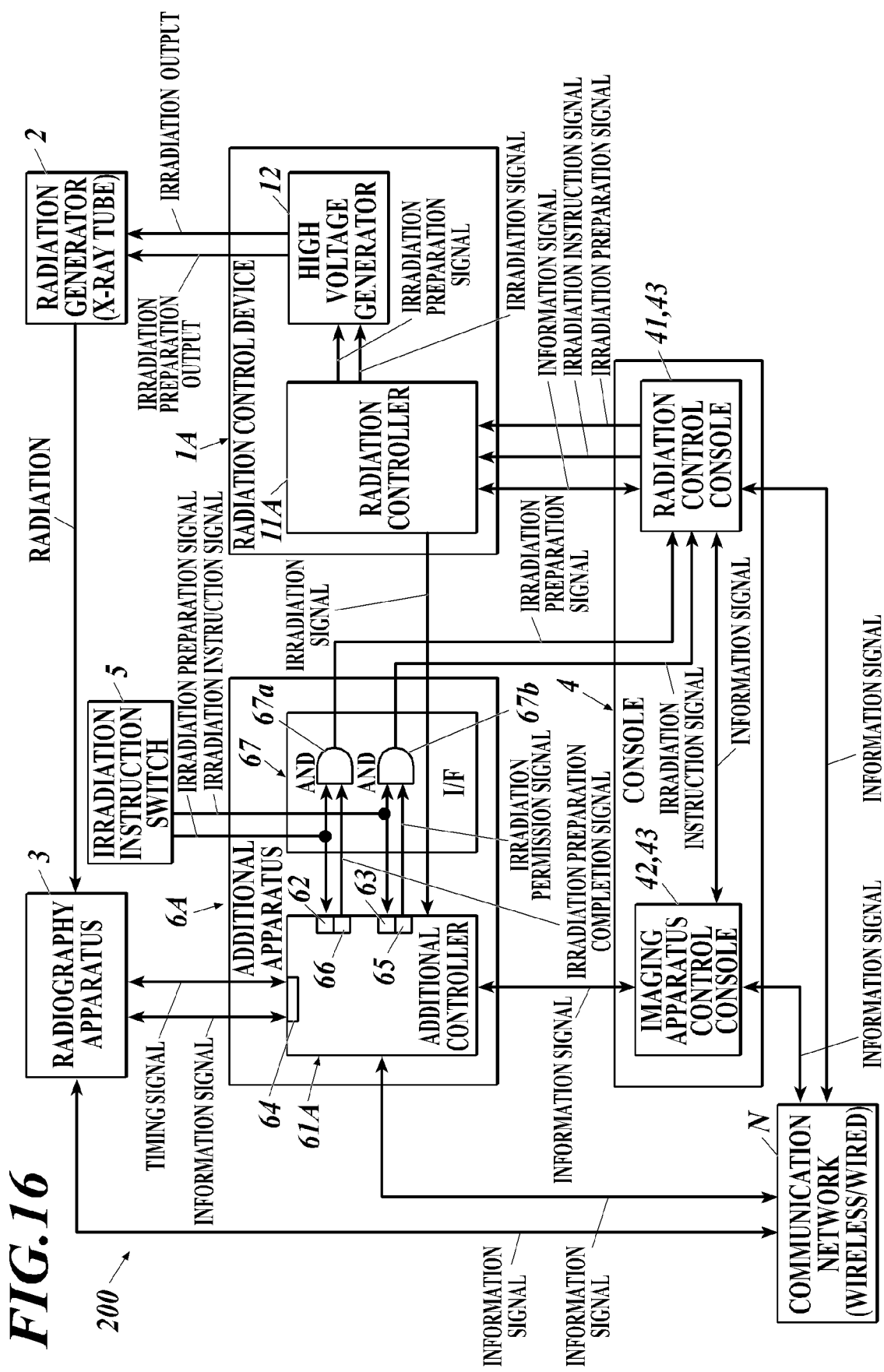
FIG. 16 is a block diagram illustrating the radiography system according to the third and fourth embodiments of the invention.

For example, as illustrated in FIG. 16, the system 200 according to the invention differs from the conventional system 200A (see FIG. 15) in that the imaging apparatus 3 replaces the cassette 3A and the system 200 further includes the same imaging apparatus control console 42 as that in the first and second embodiments and the additional apparatus 6A.

The additional apparatus 6A includes an additional controller 61A and an interface (hereinafter, referred to as an I/F 67).

FIG. 16 illustrates an example in which the additional apparatus 6A is divided into the additional controller 61A and the I/F 67. However, the additional controller 61A and the I/F 67 may be integrated.

The additional controller 61A includes a third connector 66 in addition to the first acquirer 62, the second acquirer 63, the first connector 64, and the second connector 65 which are the same as those in the first and second embodiments.

The I/F 67 includes a first AND circuit 67a and a second AND circuit 67b.

The first acquirer 62 is connected to one input terminal of the first AND circuit 67a and the third connector 66 is connected to the other input terminal of the first AND circuit 67a.

The second acquirer 63 is connected to one input terminal of the second AND circuit 67b and the second connector 65 is connected to the other input terminal of the second AND circuit 67b.

In the system 100 according to the first and second embodiments, the irradiation instruction switch 5 is connected to the console 4 and outputs the irradiation preparation signal or the irradiation instruction signal to the additional apparatus 6 through the radiation control device 1. However, in the system 200 according to this embodiment, the irradiation instruction switch 5 that can output the irradiation preparation signal or the irradiation instruction signal is directly connected to the additional apparatus 6A.

The additional apparatus 6A is configured such that the irradiation preparation signal or the irradiation instruction signal from the irradiation instruction switch 5 can be input to the additional controller 61A and the one input terminal of each of the first and second AND circuits 67a and 67b of the I/F 67. That is, the first acquirer 62 can directly acquire the irradiation preparation signal from the irradiation instruction switch 5 and the second acquirer 63 can directly acquire the irradiation instruction signal from the irradiation instruction switch 5.

In addition, a substrate or an apparatus provided with the irradiation instruction switch 5 may be connected to the I/F 67 and the first and second acquirers 62 and 63 may acquire the irradiation preparation signal or the irradiation instruction signal output from the irradiation instruction switch 5 through the substrate or the apparatus.

The third connector 66 according to this embodiment outputs an imaging preparation completion signal to the first AND circuit 67a and the second connector 65 outputs the irradiation permission signal to the second AND circuit 67b. In a case where the AND conditions of the input signals with the irradiation preparation signal and the irradiation instruction signal from the irradiation instruction switch 5 are established in the first and second AND circuits 67a and 67b, the irradiation preparation signal and the irradiation instruction signal can be output to the radiation controller 11 through the radiation control console 41.

That is, the second connector 65 according to this embodiment can be connected to the radiation generation apparatus through the I/F 67. Therefore, the I/F 67 or the radiation control console 41 according to this embodiment form a relay according to the invention.

FIG. 16 illustrates an example in which the irradiation preparation signal from the irradiation instruction switch 5 is branched by the I/F 67 so as to be input to the additional controller 61A and the first AND circuit 67a and the irradiation preparation signal is output from the I/F 67 in a case where the AND condition of the irradiation preparation signal and the imaging preparation completion signal from the additional controller 61A is established. However, this configuration may not be applied to the irradiation preparation signal and the irradiation preparation signal may be directly output from the irradiation instruction switch 5 to the radiation control console 41 or the radiation controller 11A.

In addition, FIG. 16 illustrates a configuration in which the third connector 66 directly transmits and receives information or signals to and from the imaging apparatus 3. However, the third connector 66 may be connected to another apparatus through a relay (not illustrated) that can relay signals.

Further, FIG. 16 illustrates a case where the first acquirer 62, the second acquirer 63, the first connector 64, and the second connector 65 are separately provided. However, at least two of the first acquirer 62, the second acquirer 63, the first connector 64, the second connector 65, and the third connector 66 may be integrated (the components 62 to 66 may be shared).

The irradiation preparation signal and the irradiation instruction signal output from the additional apparatus 6A may be directly input to the radiation controller 11A without passing through the radiation control console 41, which is not illustrated.

A program executed by the additional controller 61A may be different from that executed by the additional controller 61 according to the first and second embodiments and the structure of the additional controller 61A may be different from that of the additional controller 61 according to the first and second embodiments (the additional controller 61 according to the first and second embodiments also has the third connector 66 and a command for using the third connector 66 may not be included in the program such that the same additional controller as the additional controller 61 can be used, which is not illustrated in FIG. 16). Alternatively, an additional controller 61A that is limited to necessary functions may be used separately from the additional controller 61.

If the additional controller 61A detects that the irradiation preparation signal from the irradiation instruction switch 5 has been turned on, it turns on the imaging preparation signal output to at least one of the imaging apparatus 3 and the console 4.

If the additional controller 61A detects that the imaging preparation completion signal from at least one of the console 4 and the imaging apparatus 3 has been turned on, it turns on the imaging preparation completion signal output to the other input terminal of the first AND circuit 67a of the I/F 67.

If the additional controller 61A detects that the irradiation instruction signal from the irradiation instruction switch 5 has been turned on, it turns on the imaging start signal output to at least one of the imaging apparatus 3 and the console 4.

If the additional controller 61A detects that the irradiation start signal from at least one of the console 4 and the imaging apparatus 3 has been turned on, it repeatedly outputs the same irradiation permission signal (for example, a pulse signal) as that in the first and second embodiments to the other input terminal of the second AND circuit 67b of the I/F 67 with a predetermined period.

The additional controller 61A repeatedly outputs the same timing signal (for example, a pulse signal) as that in the first and second embodiments to the imaging apparatus 3 with a predetermined period.

The additional controller 61A may be configured to include the same timer as that in the first and second embodiments in order to control the transmission timing of the irradiation permission signal or the timing signal as described above.

In some cases, a plurality of generation apparatuses are connected to the system 200 as illustrated in FIG. 4, similarly to the system 100 according to the first and second embodiments. In this case, one of the generation apparatuses is selected and used.

Similarly, in some cases, a plurality of imaging apparatuses 3 are connected to the system 200. In this case, one of the imaging apparatuses is selected and used.

The additional apparatus 6A includes the additional controller 61A and the interface (Hereinafter, referred to as the I/F 67).

FIG. 16 illustrates an example in which the additional apparatus 6A is divided into the additional controller 61A and the I/F 67. However, the additional controller 61A and the I/F 67 may be integrated.

The additional controller 61A includes the third connector 66 in addition to the first acquirer 62, the second acquirer 63, the first connector 64, and the second connector 65 which are the same as those in the first and second embodiments.

The I/F 67 includes the first AND circuit 67a and the second AND circuit 67b.

The first acquirer 62 is connected to one input terminal of the first AND circuit 67a and the third connector 66 is connected to the other input terminal of the first AND circuit 67a.

The second acquirer 63 is connected to one input terminal of the second AND circuit 67b and the second connector 65 is connected to the other input terminal of the second AND circuit 67b.

In the system 100 according to the first and second embodiments, the irradiation instruction switch 5 is connected to the console 4 and outputs the irradiation preparation signal or the irradiation instruction signal to the additional apparatus 6 through the radiation control device 1. However, in the system 200 according to this embodiment, the irradiation instruction switch 5 that can output the irradiation preparation signal or the irradiation instruction signal is directly connected to the additional apparatus 6A.

The additional apparatus 6A is configured such that the irradiation preparation signal or the irradiation instruction signal from the irradiation instruction switch 5 can be input to the additional controller 61A and the one input terminal of each of the first and second AND circuits 67a and 67b of the I/F 67. That is, the first acquirer 62 can directly acquire the irradiation preparation signal from the irradiation instruction switch 5 and the second acquirer 63 can directly acquire the irradiation instruction signal from the irradiation instruction switch 5.

In addition, a substrate or an apparatus provided with the irradiation instruction switch 5 may be connected to the I/F 67 and the first and second acquirers 62 and 63 may acquire the irradiation preparation signal or the irradiation instruction signal output from the irradiation instruction switch 5 through the substrate or the apparatus.

The third connector 66 according to this embodiment outputs the imaging preparation completion signal to the first AND circuit 67a and the second connector 65 outputs the irradiation permission signal to the second AND circuit 67b. In a case where the AND conditions of the input signals with the irradiation preparation signal and the irradiation instruction signal from the irradiation instruction switch 5 are established in the first and second AND circuits 67a and 67b, the irradiation preparation signal and the irradiation instruction signal can be output to the radiation controller 11 through the radiation control console 41.

That is, the second connector 65 according to this embodiment can be connected to the generation apparatus through the I/F 67. Therefore, the I/F 67 or the radiation control console 41 according to this embodiment form the relay according to the invention.

FIG. 16 illustrates the example in which the irradiation preparation signal from the irradiation instruction switch 5 is branched by the I/F 67 so as to be input to the additional controller 61A and the first AND circuit 67a and the irradiation preparation signal is output from the I/F 67 in a case where the AND condition of the irradiation preparation signal and the imaging preparation completion signal from the additional controller 61A is established. However, this configuration may not be applied to the irradiation preparation signal and the irradiation preparation signal may be directly output from the irradiation instruction switch 5 to the radiation control console 41 or the radiation controller 11A.

In addition, FIG. 16 illustrates the configuration in which the third connector 66 directly transmits and receives information or signals to and from the imaging apparatus 3. However, the third connector 66 may be connected to another apparatus through a relay (not illustrated) that can relay signals.

Further, FIG. 16 illustrates a case where the first acquirer 62, the second acquirer 63, the first connector 64, and the second connector 65 are separately provided. However, at least two of the first acquirer 62, the second acquirer 63, the first connector 64, the second connector 65, and the third connector 66 may be integrated (the components 62 to 66 may be shared).

The irradiation preparation signal and the irradiation instruction signal output from the additional apparatus 6A may be directly input to the radiation controller 11A without passing through the radiation control console 41, which is not illustrated.

A program executed by the additional controller 61A may be different from that executed by the additional controller 61 according to the first and second embodiments and the structure of the additional controller 61A may be the same as that of the additional controller 61 according to the first and second embodiments (the additional controller 61 according to the first and second embodiments also has the third connector 66 and a command for using the third connector 66 may not be included in the program such that the same additional controller as the additional controller 61 can be used, which is not illustrated in FIG. 16). Alternatively, an additional controller 61A that is limited to necessary functions may be used separately from the additional controller 61.

If the additional controller 61A detects that the irradiation preparation signal from the irradiation instruction switch 5 has been turned on, it turns on the imaging preparation signal output to at least one of the imaging apparatus 3 and the console 4.

If the additional controller 61A detects that the imaging preparation completion signal from at least one of the console 4 and the imaging apparatus 3 has been turned on, it turns on the imaging preparation completion signal output to the other input terminal of the first AND circuit 67a of the I/F 67.

If the additional controller 61A detects that the irradiation instruction signal from the irradiation instruction switch 5 has been turned on, it turns on the imaging start signal output to at least one of the imaging apparatus 3 and the console 4.

If the additional controller 61A detects that the irradiation start signal from at least one of the console 4 and the imaging apparatus 3 has been turned on, it repeatedly outputs the same irradiation permission signal (for example, a pulse signal) as that in the first and second embodiments to the other input terminal of the second AND circuit 67b of the I/F 67 with a predetermined period.

The additional controller 61A repeatedly outputs the same timing signal (for example, a pulse signal) as that in the first and second embodiments to the imaging apparatus 3 with a predetermined period.

The additional controller 61A may be configured to include the same timer as that in the first and second embodiments in order to control the transmission timing of the irradiation permission signal or the timing signal as described above.

Operation

The operation of the system 200 will be described. FIGS. 17 and 18 are ladder charts illustrating the operation of the system 200 according to this embodiment.

As illustrated in FIG. 17, the following are the same as those in the first and second embodiments.

A: operations when an apparatus is installed, when an apparatus starts up, when the connected apparatus is changed, and when the connected apparatus is periodically checked (Steps S1 and S2)

B: an operation in preparation for imaging (Steps S3 to S13)

C: Imaging Check (Preparation for Irradiation)

The additional apparatus 6A continues to repeatedly transmit the timing signal to the imaging apparatus 3 and the imaging apparatus 3 repeats the reading operation of the imaging apparatus 3 whenever the timing signal is received.

If the radiographer ends the positioning of the subject and presses the irradiation instruction switch 5 to the first stage (Step S14), the irradiation instruction switch 5 turns on the irradiation preparation signal output to the additional apparatus 6A (Step S15A).

The irradiation preparation signal is input to the additional controller 61A and the one input terminal of the first AND circuit 67a of the I/F 67.

In this case, the additional controller 61A is connected to the other input terminal of the first AND circuit 67a. Therefore, in a case where the imaging preparation completion signal input to the other input terminal of the first AND circuit 67a is not turned on even though the irradiation preparation signal input from the irradiation instruction switch 5 to the one input terminal of the first AND circuit 67a is turned on, the irradiation preparation signal output from the first AND circuit 67a to the radiation control console 41 is maintained in the off state.

If the additional controller 61A detects that the irradiation preparation signal from the irradiation instruction switch 5 has been turned on, it transmits the imaging preparation signal for instructing preparation for imaging to at least one of the console 4 and the imaging apparatus 3 (Step S17).

If at least one of the console 4 and the imaging apparatus 3 receives the imaging preparation signal, it prepares imaging. If the preparation for imaging is completed, the at least one of the console 4 and the imaging apparatus 3 turns on the imaging preparation completion signal output to the additional apparatus 6A (Step S18).

Control of Preparation for Imaging in External Apparatus

In a case where at least one of the console 4 and the imaging apparatus 3 has a connector for inputting the imaging preparation completion signal indicating whether preparation for imaging has been completed from an external apparatus, which is not illustrated, if at least one of the console 4 and the imaging apparatus 3 detects that the imaging preparation completion signal from the external apparatus has been turned on, it may turn on the imaging preparation completion signal.

Alternatively, the additional apparatus 6A or the additional controller 61A may be provided with a connector for outputting the imaging preparation signal to an external apparatus or a connector that can input the imaging preparation completion signal from an external apparatus, which is not illustrated.

In this case, the additional apparatus 6A or the additional controller 61A can instruct the external apparatus to prepare imaging, or can detect the completion of preparation for imaging in the external apparatus and output the imaging preparation completion signal to the I/F in response to the completion of preparation for imaging in the external apparatus.

The additional apparatus 6A detects that the imaging preparation completion signal has been turned on to know that at least one of the console 4 and the imaging apparatus 3 or the external device is in a state in which it can perform imaging. The additional apparatus 6A performs control such that radiation is emitted after the imaging preparation completion signal is turned on. Therefore, it is possible to surely eliminate the risk that at least one of the console 4 and the imaging apparatus 3 or the external apparatus will emit radiation while imaging is not possible and the subject will be unnecessarily exposed to radiation.

If at least one of the console 4 and the imaging apparatus 3 detects that the imaging preparation signal has been turned on, enters an imaging preparation operation, or completes the imaging preparation operation, it turns on a signal indicating whether the imaging preparation signal has been received, a signal indicating whether the imaging preparation operation has started, or an imaging preparation completion signal indicating whether the imaging preparation operation has been completed (Step S18). In this case, the turned-on signal is transmitted to the additional apparatus 6A.

If the additional apparatus 6A detects that the imaging preparation completion signal has been turned on, it turns on the imaging preparation completion signal output to the other input terminal of the first AND circuit 67a of the I/F 67.

In this case, since both the irradiation preparation signal input to the first AND circuit 67a of the I/F 67 from the irradiation instruction switch 5 and the imaging preparation completion signal from the additional controller 61A are turned on, the first AND circuit 67a turns on the irradiation preparation signal output to the radiation control console 41.

If the radiation control console 41 detects that the irradiation preparation signal has been turned on, it turns on the irradiation preparation signal output to the radiation controller 11A (radiation generation apparatus). That is, the additional apparatus 6A turns on the irradiation preparation signal transmitted to the radiation generation apparatus through the radiation control console 41 (Step S18A).

If the radiation generation apparatus (the radiation controller 11A, the high voltage generator 12, and the radiation generator 2) detects that the irradiation preparation signal has been turned on, it prepares the emission of radiation as in the first and second embodiments.

A case where the additional apparatus 6A checks the completion of preparation for imaging in the imaging apparatus 3 or the console 4 (receives the imaging preparation completion signal) and then transmits the irradiation preparation signal to the radiation controller 11A has been described above. However, the additional apparatus 6A may transmit the irradiation preparation signal to the imaging apparatus 3 or the console 4 and the radiation controller 11A at the same time, without checking the completion of preparation for imaging in the imaging apparatus 3 or the console 4.

In this case, the first AND circuit 67a of the I/F 67 is not necessary and the irradiation preparation signal received from the irradiation instruction switch 5 may be distributed to each of the console 4, the imaging apparatus 3, the radiation control console 41, and the radiation controller 11A.

D: Execution of Imaging

If the radiographer presses the irradiation instruction switch 5 to the second stage (Step S20), the irradiation instruction switch 5 turns on the irradiation instruction signal transmitted to the additional apparatus 6A (Step S21A).

In this case, the additional apparatus 6A continues to repeatedly transmit the timing signal to the imaging apparatus 3 and the imaging apparatus 3 repeats the reading operation whenever the timing signal is received.

The irradiation instruction signal is input to each of the additional controller 61A and the one input terminal of the second AND circuit 67b of the I/F 67.

In this case, the additional controller 61A is connected to the other input terminal of the second AND circuit 67b. Therefore, in a case where the irradiation permission signal is not input to the other input terminal of the second AND circuit 67b even though the irradiation instruction signal input from the irradiation instruction switch 5 to the one input terminal of the first AND circuit 67b is turned on, the irradiation instruction signal output from the second AND circuit 67b to the radiation control console 41 is maintained in the off state.

If the additional apparatus 6A detects that the irradiation instruction signal from the irradiation instruction switch 5 has been turned on, it turns on the imaging start signal output to at least one of the console 4 and the imaging apparatus 3 (Steps S23 and S24).

Figure 18:
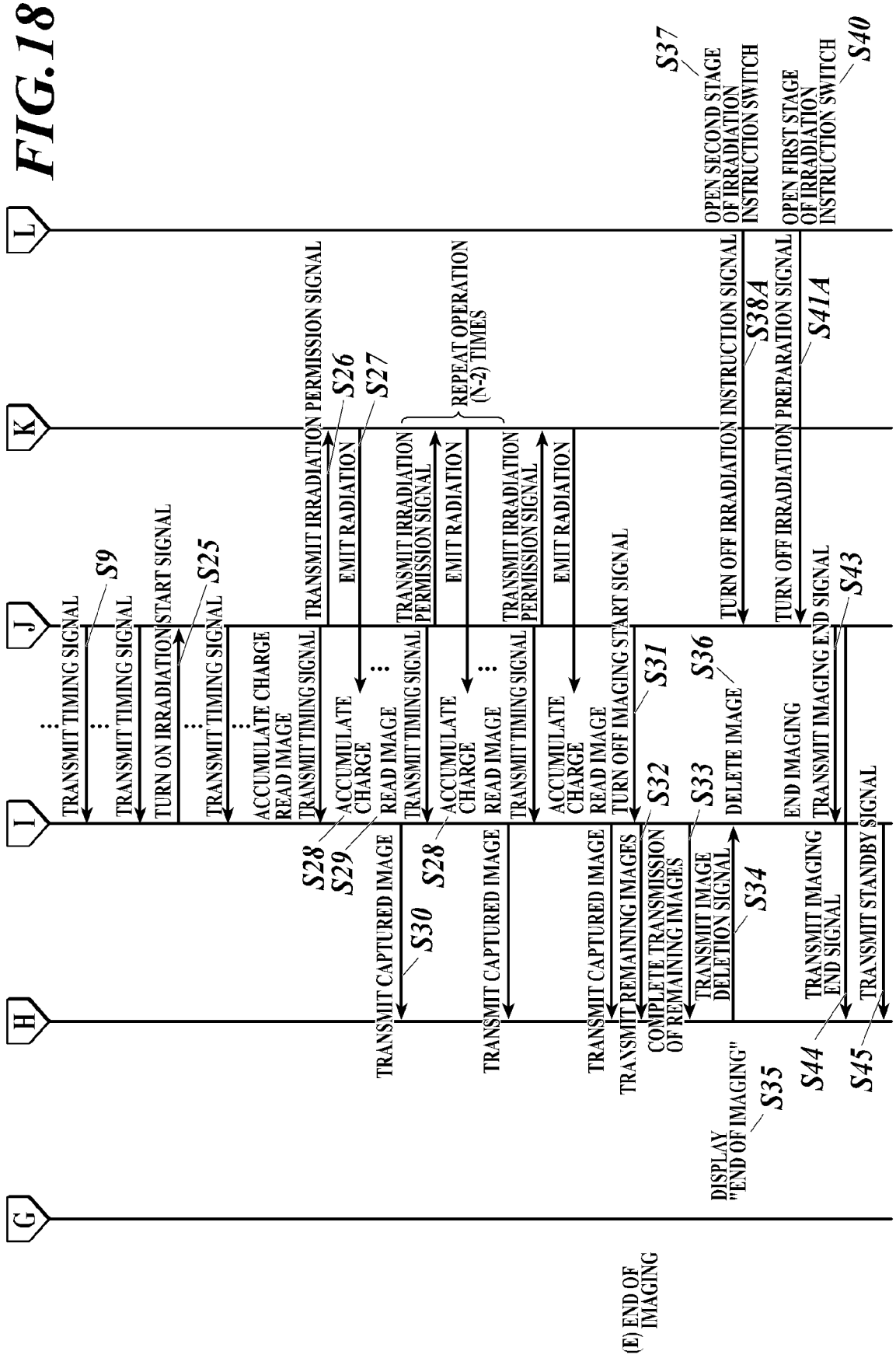
FIG. 18 is a ladder chart illustrating the second half of the operation of the radiography system according to the third embodiment.

If it is detected that the imaging start signal has been turned on, for example, the imaging apparatus 3 turns on the irradiation start signal output to the additional apparatus 6A, using the end of its reading operation performed at that time as a trigger, as illustrated in FIG. 18 (Step S25).

If the additional controller 61A detects that the irradiation start signal from the imaging apparatus 3 has been turned on, it determines that the imaging apparatus 3 is in a state in which the imaging apparatus 3 can perform imaging and repeatedly inputs the irradiation permission signal to the other input terminal of the second AND circuit 67b of the I/F 67 whenever the timing signal is transmitted to the imaging apparatus 3.

In this case, since both the irradiation instruction signal input from the irradiation instruction switch 5 to the second AND circuit 67b of the I/F 67 and the irradiation permission signal input from the additional controller 61A to the second AND circuit 67b of the I/F 67 are turned on, the second AND circuit 67b repeatedly transmits the irradiation instruction signal to the radiation controller 11A through the radiation control console 41 (Step S26A).

An operation (Step S27 to S30) in the second half of "D: Execution of imaging" and an operation (Step S31 to S36) in the first half of "E: End of Imaging" are the same as those in the first and second embodiments.

End of Imaging

In a case where the radiographer who has checked the end of imaging releases the second stage of the irradiation instruction switch 5 (Step S37), the irradiation instruction switch 5 turns off the irradiation instruction signal (Step S38A). Then, the imaging apparatus 3 turns off the imaging start signal.

Then, in a case where the radiographer releases the first stage of the irradiation instruction switch 5 (Step S40), the irradiation instruction switch 5 turns off the irradiation preparation signal (Step S41A).

Steps S43 to S45 are the same as those in the first and second embodiments.

In this way, a series of imaging operations ends.

The system 200 according to this embodiment operates as described above to perform dynamic imaging which repeatedly captures a plurality of still images in a short time, similarly to the system 100 according to the first and second embodiments.

Effect

As described above, the system 200 according to this embodiment is configured by connecting the additional controller 61A to the radiation control device 1 that can perform only one radiation emission operation in response to one radiation emission instruction in the conventional system 200A illustrated in FIG. 15. Therefore, the radiation control device 1 can output the irradiation signal a plurality of times in response to one irradiation instruction (the pressing of the irradiation instruction switch 5 to the second stage). As a result, it is possible to perform imaging that repeatedly captures still images a plurality of times in a short time using the imaging apparatus 3, that is, dynamic imaging.

The conventional system 200A illustrated in FIG. 15 is widely used as a radiography apparatus that captures a simple still image. Therefore, a medical institution using the conventional system 200A can easily modify the conventional system 200A including the existing radiation generation apparatus so as to respond to the dynamic imaging only by adding the imaging apparatus 3 and the additional apparatus 6A, without updating the expensive radiation generation apparatus.

The system 200 according to this embodiment may be configured such that the additional apparatus 6A is divided into the additional controller 61A and the I/F 67 and the additional controller 61A has the same structure as the additional controller 61 in the first and second embodiments (except for only the stored program). In this case, it is possible to manufacture the additional apparatus 6 according to the first and second embodiments and the additional apparatus 6A according to the third embodiment (to modify the conventional system 100A and the conventional system 200A) using common components, without increasing the type of apparatus.

In the third embodiment, the configuration in which the additional apparatus 6A is added to the conventional system 200A illustrated in FIG. 15 such that dynamic imaging can be performed has been described. However, the embodiment of the invention is not limited thereto. For example, the additional apparatus 6A according to the third embodiment may be added to the conventional system 100A illustrated in FIG. 1 such that dynamic imaging can be performed.

For example, the conventional system 100A illustrated in FIG. 1 can be used as the radiography system according to the invention by keeping the irradiation permission signal input to the radiation controller 11 of the conventional system 100A illustrated in FIG. 1 in an on state.

According to this configuration, dynamic imaging can be performed by adding the additional apparatus to various types of radiography systems.

Fourth Embodiment

A fourth embodiment of the invention will be described with reference to FIGS. 16, 17, 19, and 20. The same configurations as those in the first to third embodiments are denoted by the same reference numerals and the description thereof will not be repeated. In addition, various modification patterns described in the first to third embodiments may also be applied to this embodiment.

Premise, Background, and Task

There is a radiography system including the radiation controller 11 illustrated in Conventional Technology 1 which has an input port for the irradiation permission signal from the outside and transmits the irradiation signal according to the irradiation instruction from the radiographer and the irradiation permission from the outside. In addition, there is a radiography system including the radiation controller 11A illustrated in Conventional Technology 2 which has only an input port for the irradiation instruction signal from the outside and captures a still image.

A radiography system (hereinafter, referred to as a system 200) according to this embodiment is configured such that the additional apparatus 6A is added to the radiation controller 11A to continuously perform imaging System Configuration First, the system configuration of the radiography system 200 will be described. FIG. 16 is a block diagram illustrating the schematic configuration of the system 200 according to the fourth embodiment.

For example, as illustrated in FIG. 16, the system 200 according to the invention differs from the conventional system 200A (see FIG. 15) in that the imaging apparatus 3 replaces the cassette 3A and the system 200 further includes the same imaging apparatus control console 42 as that in the first to third embodiments and the additional apparatus 6A.

Operation

Figure 19:
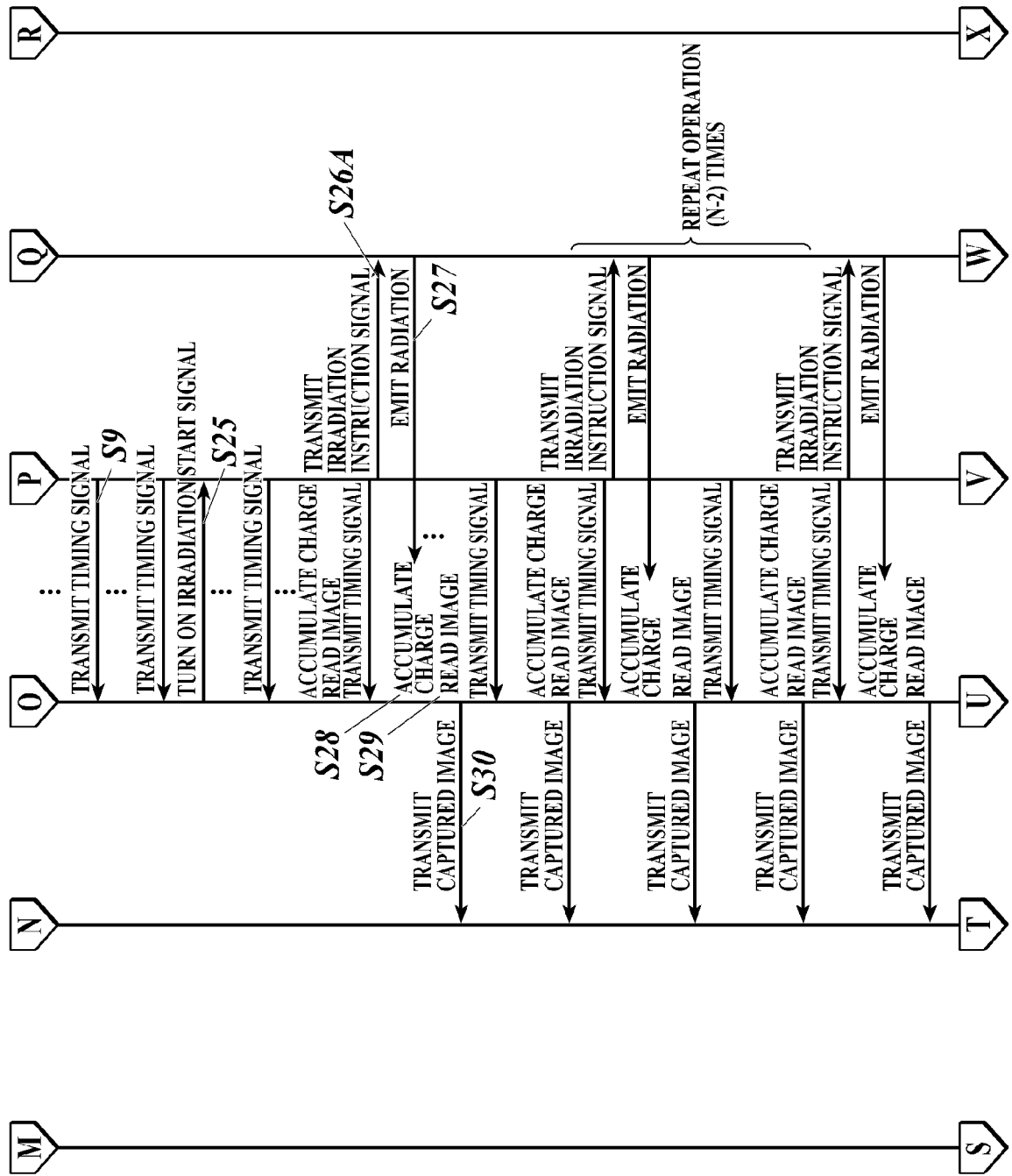
FIG. 19 is a ladder chart illustrating the middle of the operation of the radiography system according to the fourth embodiment.
Figure 20:
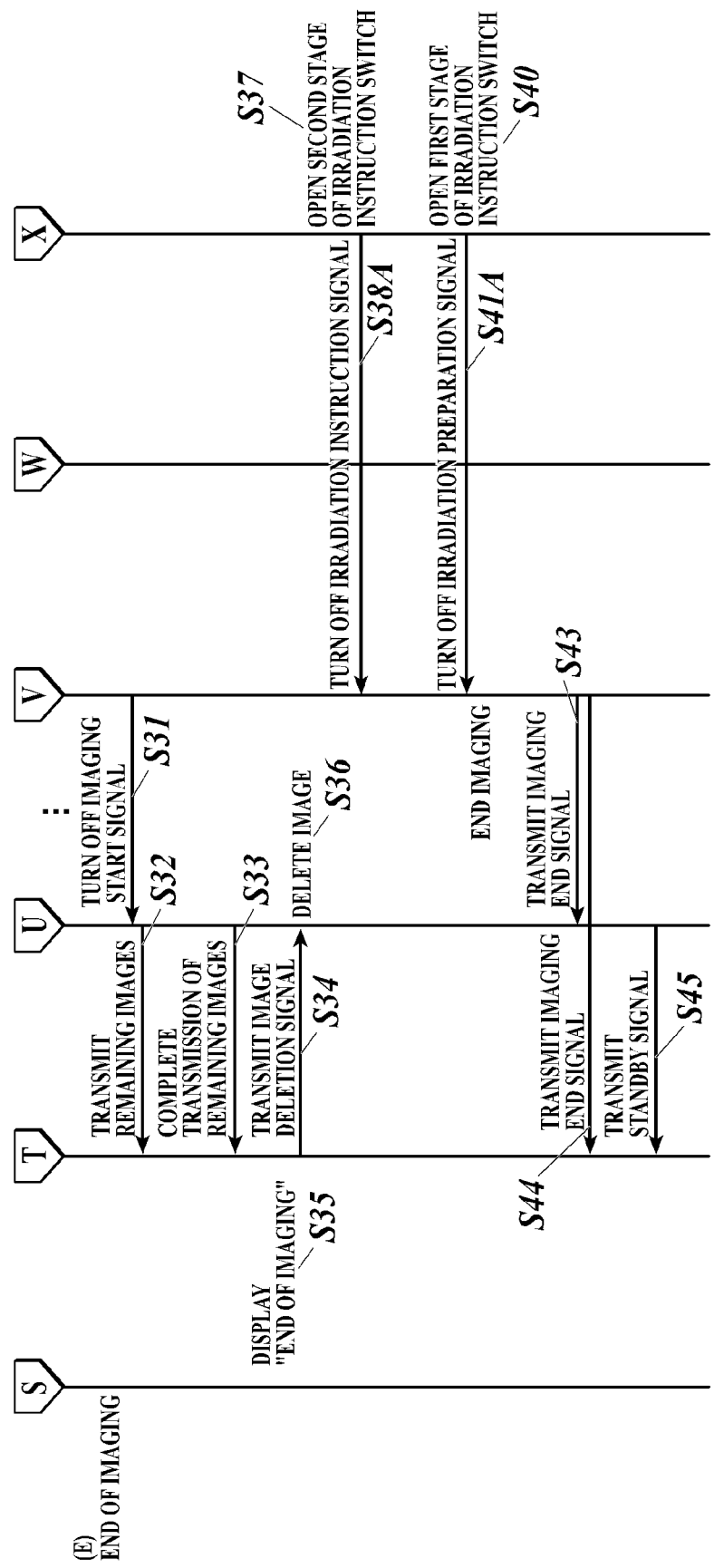
FIG. 20 is a ladder chart illustrating the second half of the operation of the radiography system according to the fourth embodiment.

The operation of the system 200 will be described. FIGS. 17, 19, and 20 are ladder charts illustrating the operation of the system 200 according to this embodiment.

As illustrated in FIG. 17, the following are the same as those in the first to third embodiments.

A: Operations when an apparatus is installed, when an apparatus starts up, when the connected apparatus is changed, and when the connected apparatus is periodically checked" (Steps S1 and S2)

B: an operation in preparation for imaging (Steps S3 to S13)

That is, in the system 200 according to this embodiment, similarly to the system 100 according to the first to third embodiments, imaging can be performed even in a case where a combination of the generation apparatus and the imaging apparatus 3 is changed. Therefore, it is possible to select a cassette-type imaging apparatus 3 suitable for an imaging order or an imaging technique from a plurality of cassette-type imaging apparatuses 3 with different sizes or performances and to perform imaging with the selected imaging apparatus 3.

In this case, for example, as illustrated in FIG. 8, an imaging apparatus 3 that is suitable for the current imaging is selected from a plurality of imaging apparatuses 3 that can be connected to the console 4 and can be used for imaging and imaging is performed using the selected imaging apparatus.

In the system 100 in which a plurality of generation apparatuses are connected to one console 4 which is not illustrated, a generation apparatus used for imaging is selected and imaging is performed using the selected generation apparatus.

If at least one of the generation apparatus and the imaging apparatus 3 is selected, the additional controller 61A of the additional apparatus 6A or the console 4 according to this embodiment can acquire the irradiation frame rate or the imaging frame rate.

The additional controller 61A or the console 4 can also acquire the imaging frame rate.

The irradiation frame rate or the imaging frame rate to be acquired may be input (selected) to the console 4 by the radiographer or may be received from the generation apparatus or the imaging apparatus 3.

In a case where the irradiation frame rate or the imaging frame rate is received from the generation apparatus or the imaging apparatus 3, one frame rate selected in each apparatus may be received or all of a plurality of frame rates corresponding to each apparatus may be received.

It is necessary to satisfy all of the following determination conditions (1) to (3) in order to perform imaging without any problem.

(1) The acquired irradiation frame rate is a value corresponding to the generation apparatus.

(2) The acquired imaging frame rate is a value corresponding to the imaging apparatus 3.

(3) The ratio of the irradiation frame rate to the imaging frame rate is 1:N, where N is an integer equal to or greater than 1 (the imaging frame rate is N times the irradiation frame rate).

Therefore, the additional controller 61A or the console 4 determines whether all of the determination conditions are satisfied.

Here, the "irradiation frame rate" indicates the number of times radiation is generated by the generation apparatus per unit time and corresponds to the transmission period of the irradiation permission signal by the additional controller 61A.

The "imaging frame rate" indicates the number of times a radiographic image is generated by the imaging apparatus 3 per unit time and corresponds to the transmission period of the timing signal by the additional controller 61A.

In a case where at least one of the number of irradiation frame rates and the number of imaging frame rates is two or more, there are a plurality of combinations of the irradiation frame rates and the imaging frame rates. Therefore, determination may be performed a plurality of times in accordance with the plurality of combinations.

Here, N is an integer equal to or greater than 1. However, for example, in a case where imaging is performed while thinning out radiation at predetermined intervals, it is preferable that N is an integer equal to or greater than 2.

In a case where at least one of the number of imaging frame rates received from the imaging apparatus 3 and the number of irradiation frame rates received from the generation apparatus is two or more, there may be a plurality of combinations of the imaging frame rates and the irradiation frame rates. Therefore, it may be determined in advance whether each combination satisfies all of the above-mentioned determination conditions.

In a case where the generation apparatus or the imaging apparatus is configured to select only the corresponding irradiation frame rate or the corresponding imaging frame rate, the generation apparatus, the imaging apparatus 3, or the console 4 can omit the determination of whether the determination conditions (1) and (2) are satisfied.

If any of the determination conditions is not satisfied as a result of checking whether all of the determination conditions are satisfied, at least one of the following measures (4) to (6) may be taken.

(4) Among the imaging apparatus 3 used, the generation apparatus used, the imaging frame rate of the imaging apparatus 3, and the irradiation frame rate of the generation apparatus, a component that does not satisfy the above-mentioned relationship is not selected or an input value is not received (not set).

(5) A setting candidate that does not satisfy the above-mentioned relationship is grayed out (display to notify the determination result is performed) and is excluded from a selection target such that it is not selectable.

(6) Even in a case where a component can be selected, it does not advance to the next sequence. Alternatively, imaging is not permitted.

When the above-described measures are taken, the system may notify the photographer of an error to warn the photographer that the relationship is not satisfied. In this embodiment, the warning may be performed by voice or may be performed by display for notifying the determination result using the display 43.

C: Imaging Check (Preparation for Irradiation)

The additional apparatus 6A continues to repeatedly transmit the timing signal to the imaging apparatus 3 and the imaging apparatus 3 repeats the reading operation whenever the timing signal is received.

In a case where the radiographer ends the positioning of the subject and presses the irradiation instruction switch 5 to the first stage (Step S14), the irradiation instruction switch 5 turns on the irradiation preparation signal output to the additional apparatus 6A (Step S15A).

The irradiation preparation signal is input to the additional controller 61A and the one input terminal of the first AND circuit 67a of the I/F 67.

In this case, the additional controller 61A is connected to the other input terminal of the first AND circuit 67a. Therefore, in a case where the imaging preparation completion signal input to the other input terminal of the first AND circuit 67a is not turned on even though the irradiation preparation signal input from the irradiation instruction switch 5 to the one input terminal of the first AND circuit 67a is turned on, the irradiation preparation signal output from the first AND circuit 67a to the radiation control console 41 is maintained in the off state.

If the additional controller 61A detects that the irradiation preparation signal from the irradiation instruction switch 5 has been turned on, it transmits the imaging preparation signal for instructing preparation for imaging to at least one of the console 4 and the imaging apparatus 3 (Step S17).

In this case, the additional controller 61A or the console 4 may check again the following determination conditions (1) to (3).

(1) The set irradiation frame rate is a value corresponding to the generation apparatus.

(2) The set imaging frame rate is a value corresponding to the imaging apparatus 3.

(3) The ratio of the irradiation frame rate to the imaging frame rate is 1:N, where N is an integer equal to or greater than 1 (the imaging frame rate is N times the irradiation frame rate).

If the above-mentioned relationship is not satisfied, the console 4 may prohibit an advance to the subsequent sequence or may not permit imaging.

The system may be configured to notify the radiographer of an error to warn the radiographer that the above-mentioned relationship is not satisfied when the above-described measures are taken.

If at least one of the console 4 and the imaging apparatus 3 receives the imaging preparation signal, it prepares imaging. If the preparation for imaging is completed, the at least one of the console 4 and the imaging apparatus 3 turns on the imaging preparation completion signal output to the additional apparatus 6A (Step S18).

Control of Preparation for Imaging in External Apparatus

In a case where at least one of the console 4 and the imaging apparatus 3 has a connector for inputting the imaging preparation completion signal indicating whether preparation for imaging has been completed from an external apparatus, which is not illustrated, if at least one of the console 4 and the imaging apparatus 3 detects that the imaging preparation completion signal from the external apparatus has been turned on, it may turn on the imaging preparation completion signal.

Alternatively, the additional apparatus 6A or the additional controller 61A may be provided with a connector for outputting the imaging preparation signal to an external apparatus or a connector that can input the imaging preparation completion signal from an external apparatus, which is not illustrated.

In this case, the additional apparatus 6A or the additional controller 61A can instruct the external apparatus to prepare imaging, or can detect the completion of preparation for imaging in the external apparatus and output the imaging preparation completion signal to the I/F in response to the completion of preparation for imaging in the external apparatus.

The additional apparatus 6A detects that the imaging preparation completion signal has been turned on to know that at least one of the console 4 and the imaging apparatus 3 or the external device is in a state in which it can perform imaging. The additional apparatus 6A performs control such that radiation is emitted after the imaging preparation completion signal is turned on. Therefore, it is possible to surely eliminate the risk that at least one of the console 4 and the imaging apparatus 3 or the external apparatus will emit radiation while imaging is not possible and the subject will be unnecessarily exposed to radiation.

If at least one of the console 4 and the imaging apparatus 3 detects that the imaging preparation signal has been turned on, enters an imaging preparation operation, or completes the imaging preparation operation, it turns on a signal indicating whether the imaging preparation signal has been received, a signal indicating whether the imaging preparation operation has started, or an imaging preparation completion signal indicating whether the imaging preparation operation has been completed (Step S18). In this case, the turned-on signal is transmitted to the additional apparatus 6A.

If the additional apparatus 6A detects that the imaging preparation completion signal has been turned on, it turns on the imaging preparation completion signal output to the other input terminal of the first AND circuit 67a of the I/F 67.

In this case, since both the irradiation preparation signal input from the irradiation instruction switch 5 to the first AND circuit 67a of the I/F 67 and the imaging preparation completion signal from the additional controller 61A are turned on, the first AND circuit 67a turns on the irradiation preparation signal output to the radiation control console 41.

If the radiation control console 41 detects that the irradiation preparation signal has been turned on, it turns on the irradiation preparation signal output to the radiation controller 11A (generation apparatus). That is, the additional apparatus 6A turns on the irradiation preparation signal transmitted to the generation apparatus through the radiation control console 41 (Step S18A).

If the generation apparatus (the radiation controller 11A, the high voltage generator 12, and the radiation generator 2) detects that the irradiation preparation signal has been turned on, it prepares the emission of radiation as in the first to third embodiments.

A case where the additional apparatus 6A checks the completion of preparation for imaging in the imaging apparatus 3 or the console 4 (receives the imaging preparation completion signal) and then transmits the irradiation preparation signal to the radiation controller 11A has been described above. However, the additional apparatus 6A may transmit the irradiation preparation signal to the imaging apparatus 3 or the console 4 and the radiation controller 11A at the same time, without checking the completion of preparation for imaging in the imaging apparatus 3 or the console 4.

In this case, the first AND circuit 67a of the I/F 67 is not necessary and the irradiation preparation signal received from the irradiation instruction switch 5 may be distributed to each of the console 4, the imaging apparatus 3, the radiation control console 41, and the radiation controller 11A.

D: Execution of Imaging

Then, in a case where the radiographer presses the irradiation instruction switch 5 to the second stage (Step S20), the irradiation instruction switch 5 turns on the irradiation instruction signal transmitted to the additional apparatus 6A (Step S21A).

In this case, the additional apparatus 6A continues to repeatedly transmit the timing signal to the imaging apparatus 3 and the imaging apparatus 3 repeats the reading operation whenever the timing signal is received.

The irradiation instruction signal is input to each of the additional controller 61A and the one input terminal of the second AND circuit 67b of the I/F 67.

In this case, the additional controller 61A is connected to the other input terminal of the second AND circuit 67b. Therefore, in a case where the irradiation permission signal is not input to the other input terminal of the second AND circuit 67b even though the irradiation instruction signal input from the irradiation instruction switch 5 to the one input terminal of the first AND circuit 67b is turned on, the irradiation instruction signal output from the second AND circuit 67b to the radiation control console 41 is maintained in the off state.

In a case where the additional apparatus 6A detects that the irradiation instruction signal from the irradiation instruction switch 5 has been turned on, it turns on the imaging start signal output to at least one of the console 4 and the imaging apparatus 3 (Steps S23 and S24).

In this case, the additional controller 61A or the console 4 may check again the following determination conditions (1) to (3).

(1) The set irradiation frame rate is a value corresponding to the generation apparatus.

(2) The set imaging frame rate is a value corresponding to the imaging apparatus 3.

(3) The ratio of the irradiation frame rate to the imaging frame rate is 1:N, where N is an integer equal to or greater than 1 (the imaging frame rate is N times the irradiation frame rate).

If the above-mentioned relationship is not satisfied, the console 4 may prohibit an advance to the subsequent sequence or may not permit imaging.

The system may be configured to notify the radiographer of an error to warn the radiographer that the above-mentioned relationship is not satisfied when the above-described measures are taken.

If it is detected that the imaging start signal has been turned on, for example, the imaging apparatus 3 turns on the irradiation start signal output to the additional apparatus 6A, using the end of its reading operation performed at that time as a trigger, as illustrated in FIG. 19 (Step S25).

If the additional controller 61A detects that the irradiation start signal from the imaging apparatus 3 has been turned on, it determines that the imaging apparatus 3 can perform imaging and repeatedly inputs the irradiation permission signal to the other input terminal of the second AND circuit 67b of the I/F 67 whenever the timing signal is transmitted to the imaging apparatus 3.

In this case, since both the irradiation instruction signal input from the irradiation instruction switch 5 to the second AND circuit 67b of the I/F 67 and the irradiation permission signal input from the additional controller 61A to the second AND circuit 67b of the I/F 67 are turned on, the second AND circuit 67b repeatedly transmits the irradiation instruction signal to the radiation controller 11A through the radiation control console 41 (Step S26A).

In a case where the ratio of the irradiation frame rate to the imaging frame rate is set to 1:N, the additional controller 61A outputs the imaging permission signal once whenever the timing signal is output N times (FIG. 19 illustrates a case where N is 2).

The imaging apparatus 3 continues to repeatedly perform accumulation and reading Whenever the imaging apparatus 3 repeatedly performs accumulation and reading N times, it is irradiated with radiation from the generation apparatus once to generate an exposed image.

An operation (Step S27 to S30) in the second half of "D: Execution of imaging" and an operation (Step S31 to S36) in the first half of "E: End of Imaging" are the same as those in the first to third embodiments.

End of Imaging

If the radiographer who has checked the end of imaging releases the second stage of the irradiation instruction switch 5 (Step S37), the irradiation instruction switch 5 turns off the irradiation instruction signal (Step S38A). Then, the imaging apparatus 3 turns off the imaging start signal.

Then, if the radiographer releases the first stage of the irradiation instruction switch 5 (Step S40), the irradiation instruction switch 5 turns off the irradiation preparation signal (Step S41A).

Steps S43 to S45 are the same as those in the first to third embodiments.

In this way, a series of imaging operations ends.

The system 200 according to this embodiment operates as described above to perform dynamic imaging which repeatedly captures a plurality of still images in a short time, similarly to the system 100 according to the first to third embodiments.

Effect

As described above, the system 200 according to this embodiment is configured by connecting the additional controller 61A to the radiation control device 1 that can perform only one radiation emission operation in response to one radiation emission instruction in the conventional system 200A illustrated in FIG. 15. Therefore, the radiation control device 1 can output the irradiation signal a plurality of times in response to one irradiation instruction (the pressing of the irradiation instruction switch 5 to the second stage). As a result, it is possible to perform imaging that repeatedly captures still images a plurality of times in a short time using the imaging apparatus 3, that is, dynamic imaging.

The conventional system 200A illustrated in FIG. 15 is widely used as a system that captures a simple still image. Therefore, a medical institution using the conventional system 200A can easily modify the conventional system 200A including the existing generation apparatus so as to respond to the dynamic imaging only by adding the imaging apparatus 3 and the additional apparatus 6A, without updating the expensive generation apparatus.

The system 200 according to this embodiment may be configured such that the additional apparatus 6A is divided into the additional controller 61A and the I/F 67 and the additional controller 61A has the same structure as the additional controller 61 in the first to third embodiments (except for only the stored program). In this case, it is possible to manufacture the additional apparatus 6 according to the first to third embodiments and the additional apparatus 6A according to the fourth embodiment (to modify the conventional system 100A and the conventional system 200A) using common components, without increasing the type of apparatus.

The system 200 according to this embodiment notifies the radiographer of the result of determining whether the irradiation frame rate acquired by the console 4 is N times the acquired imaging frame rate (where N is an integer equal to or greater than 1) in a manner that the radiographer can recognize the determination result. Therefore, in the imaging in which, while the imaging apparatus 3 repeats charge accumulation and reading a predetermined number of times, the generation apparatus emits radiation a number of times that is equal to or less than a predetermined value, it is necessary to reliably prevent the risk of starting imaging in a state in which the frame rate that does not correspond to at least one of the imaging apparatus 3 and the generation apparatus is set.

In the fourth embodiment, the configuration in which the additional apparatus 6A is added to the conventional system 200A illustrated in FIG. 15 such that dynamic imaging can be performed has been described. However, the embodiment of the invention is not limited thereto. For example, the additional apparatus 6A according to the fourth embodiment may be added to the conventional system 100A illustrated in FIG. 1 such that dynamic imaging can be performed.

For example, the conventional system 100A illustrated in FIG. 1 can be used as the radiography system according to the invention by keeping the irradiation permission signal input to the radiation controller 11 of the conventional system 100A illustrated in FIG. 1 always in an on state.

According to this configuration, dynamic imaging can be performed by adding the additional apparatus to various types of radiography systems.

In the description of the first to fourth embodiments, various functions of the additional controller 61 or the console 4 may be included not in the additional controller 61 or the console 4 but in the radiation control device 1 or the imaging apparatus 3.

The example in which the systems 100 and 200 according to the first to fourth embodiments are configured by modifying the conventional systems 100A and 200A using the additional apparatuses 6 and 6A has been described. However, the invention is not limited to these types of radiography systems. For example, a radiography system which does not include the additional apparatus 6 or 6A and includes the imaging apparatus 3 or the radiation control device 1 or 1A having a dynamic imaging function may be used.

In this case, for example, the console 4, the radiation control device 1, or the imaging apparatus 3 has various functions.

Sequence State Change

A sequence state change operation of the systems 100 and 200 according to the first to fourth embodiments will be described with reference to FIGS. 21 and 22.

Premise, Background, and Task

The systems 100 and 200 according to the first and second embodiments are not capable of correctly performing imaging unless the connected apparatuses operate in a correct order.

Even if an error unintended by the radiographer, such as noise in a signal line or the cutting of a signal line, occurs, it is necessary to safely end imaging such that radiation is not unintentionally emitted.

Operation

First, the operation of the systems 100 and 200 will be described. FIG. 21 is a state transition diagram illustrating a change in the state of the systems 100 and 200 and FIG. 22 is a timing chart illustrating the operation of the systems 100 and 200.

Figure 21:
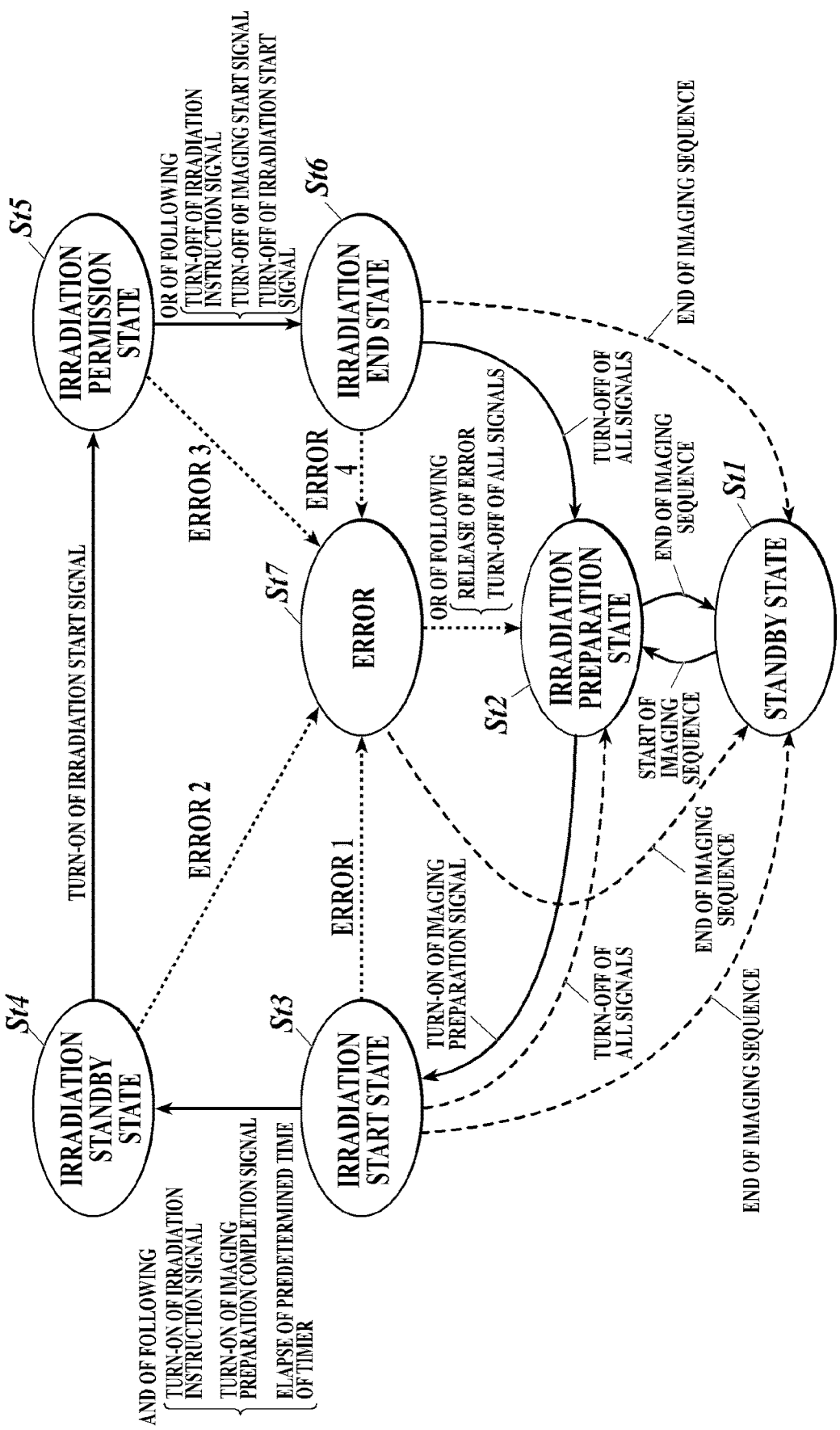
FIG. 21 is a state transition diagram illustrating a change in the state of the radiography system according to the first to fourth embodiments.

First, the systems 100 and 200 according to the embodiments are in a standby state St' in which in which the imaging start instruction is not received from the radiographer as illustrated in FIG. 21.

Figure 22:
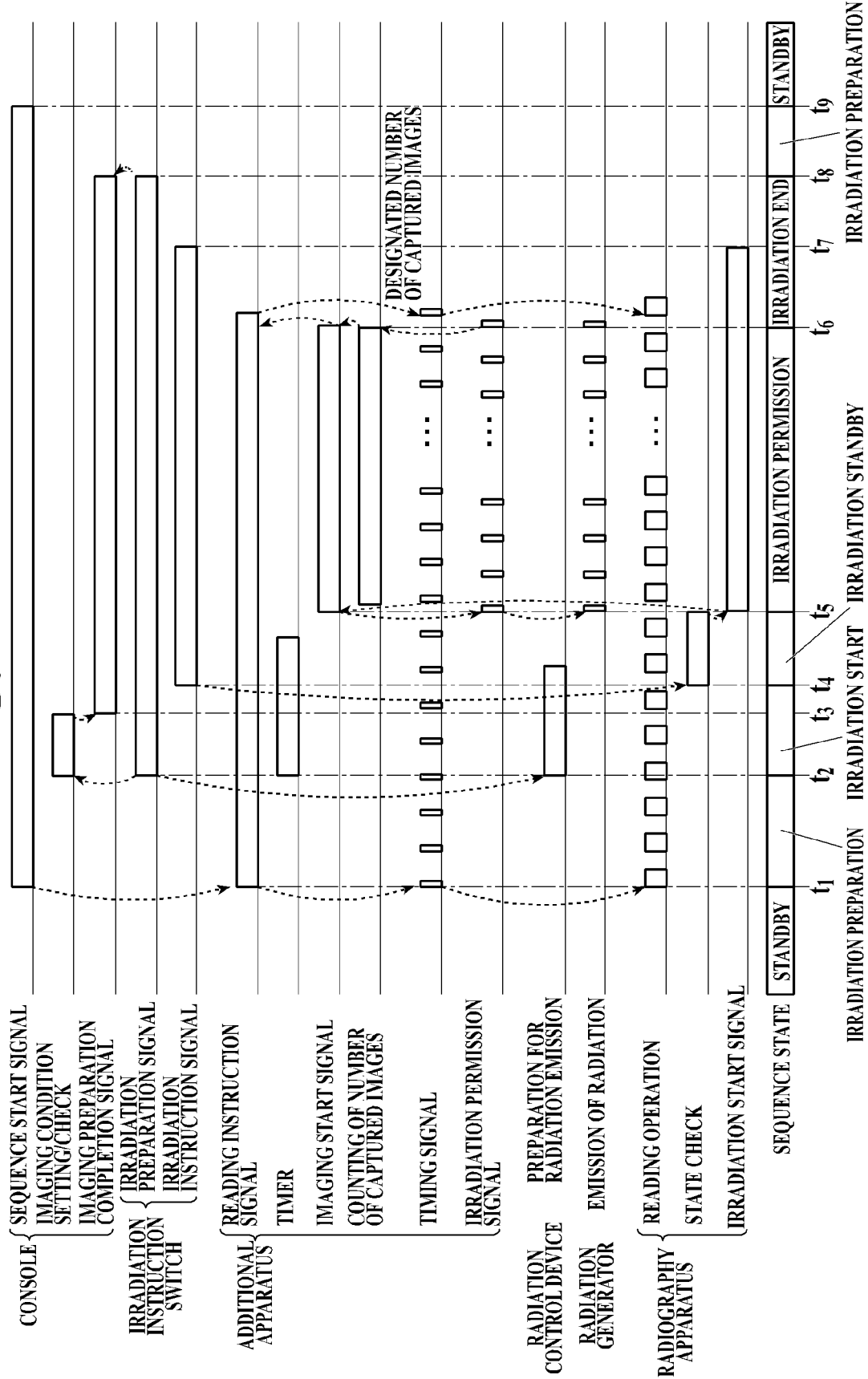
FIG. 22 is a timing chart illustrating the operation of the radiography system according to the first to fourth embodiments.

If the console 4 receives an imaging order from the host system 7, such as RIS or HIS, and the radiographer selects the imaging order, the console 4 turns on the sequence start signal output to the imaging apparatus 3 and the additional apparatus 6 or 6A as illustrated in FIG. 22 (t1).

Then, the imaging apparatus 3 and the additional apparatus 6 or 6A starts preparation for imaging. Then, the system 100 or 200 changes to an irradiation preparation state St2 as illustrated in FIG. 21.

In the irradiation preparation state St2, as illustrated in FIG. 22, the additional apparatus 6 or 6A repeatedly transmits the timing signal to imaging apparatus 3 at a predetermined interval and the imaging apparatus 3 repeats the reading operation whenever the timing signal is received. In this way, the reset operation of removing the charge accumulated in the imaging apparatus 3 is repeatedly performed.

The reading operation performed here is the same as the operation in a case where a captured image is acquired. However, since the image acquired by the reset operation has been generated in the irradiation preparation state St2 in which no radiation is emitted, the image may be stored in the memory of the imaging apparatus 3 or may be transmitted to the console 4. Alternatively, the image may be removed without being stored or transmitted.

Since at least a portion of the image acquired by the reset operation indicates the characteristics of each pixel of the imaging apparatus 3 or the characteristics of the image of the imaging apparatus 3, for example, the acquired image may be stored in the imaging apparatus 3 or may be transmitted to the console 4 as a correction image for correcting the captured image.

At least one of a plurality of images acquired by repeatedly performing the reset operation may be used as the correction image. Alternatively, the average of the signal values of the corresponding pixels in a plurality of images or a complementary estimate in the time direction may be calculated and used as the correction image.

As a method for correcting a captured image, for example, there is a method which subtracts the signal value of each pixel of the correction image from the image obtained by emitting radiation.

The system may be configured such that the timing signal can be transmitted to the imaging apparatus 3 in a state other than the irradiation preparation state St2. In addition, after the system changes to the irradiation preparation state St2, the reset operation instruction signal may be turned on such that the imaging apparatus 3 performs the reset operation only in a case where the reset operation instruction signal is turned on.

The radiographer sets, for example, imaging conditions with the imaging apparatus control console 42 or the radiation control console 41, positions the subject, and then starts an imaging operation.

Specifically, as illustrated in FIG. 22, the radiographer operates the irradiation instruction switch 5 to turn on the irradiation preparation signal transmitted to the console 4 (t2). Then, the system 100 or 200 changes to an irradiation start state St3 as illustrated in FIG. 21.

In the irradiation start state St3, the console 4 checks the state of the radiation control device 1, the imaging apparatus 3, and the additional apparatus 6 or 6A. If it is determined that imaging is possible, the console 4 turns on the imaging preparation completion signal transmitted to the additional apparatus 6 or 6A as illustrated in FIG. 21 (t3).

The console 4 may check whether the imaging conditions set in the radiation control console 41 are the same as the imaging conditions set in the imaging apparatus control console 42. If the imaging conditions are different from each other, the console 4 may display information indicating that the imaging conditions are different from each other.

In a case where the imaging conditions set in the radiation control console 41 are different from the imaging conditions set in the imaging apparatus control console 42, control may be performed such that the process does not advance to the subsequent imaging sequence.

While the imaging preparation completion signal remains on, control may be performed that the imaging conditions set in the imaging apparatus control console 42 and the radiation control console 41 are not capable of being changed.

If the radiation control device 1 detects that the irradiation preparation completion signal has been turned on, it prepares the emission of radiation (t2). This is, for example, an operation of rotating the rotating anode of the radiation generator 2.

If the additional apparatus 6 or 6A detects that the irradiation preparation signal has been turned on, it starts to count the set timer (t2).

With this configuration, even in a case where the radiographer presses the irradiation instruction switch 5 to the second stage (turns on the irradiation instruction signal), the system is not capable of shifting to an irradiation standby state St4, which will be described below, until the timer counts a predetermined standby time.

Then, the radiographer presses the irradiation instruction switch 5 to the second stage to turn on the irradiation instruction signal (t4). FIG. 22 illustrates a case where, after the imaging preparation completion signal is turned on, the irradiation instruction signal is turned on. However, before the imaging preparation completion signal is turned on, the irradiation instruction signal may be turned on.

If the additional controller 61 or 61A confirms that the irradiation instruction signal has been turned on, that the imaging preparation completion signal has been turned on, and that a predetermined standby time of the timer has passed, the system 100 or 200 changes to the irradiation standby state St4 as illustrated in FIG. 21.

In the irradiation standby state St4, the additional controller 61 or 61A checks whether the imaging apparatus 3 is in a state in which it can perform imaging. The imaging apparatus 3 checks whether it can perform imaging. If it is determined that the imaging apparatus 3 can perform imaging, the imaging apparatus 3 transmits the irradiation start signal to the additional controller 61 or 61A as illustrated in FIG. 22 (t5).

For example, whether the imaging apparatus 3 can perform imaging is checked by determining whether the charge of the light receiver in the imaging apparatus 3 has been removed after the completion of a predetermined reset operation or whether the reset operation has been completed in all of the pixels of the light receiving surface (the reset operation is performed by scanning each row of the pixels arranged in a matrix on the light receiving surface).

If the additional controller 61 or 61A detects that the irradiation start signal from the imaging apparatus 3 has been turned on, the system 100 or 200 changes to an irradiation permission state St5 as illustrated in FIG. 21.

In the irradiation permission state St5, as illustrated in FIG. 22, the additional controller 61 or 61A turns on the imaging start signal which is an internal interlock (t5) and repeatedly transmits the irradiation permission signal or the irradiation instruction signal to the radiation controller 11 or 11A at a timing corresponding to the timing when the timing signal is output to the imaging apparatus 3.

The radiation generation apparatus (the radiation controller 11 or 11A, the high voltage generator 12, and the radiation generator 2) generates radiation whenever the irradiation permission signal or the irradiation instruction signal is received such that the radiation transmitted through the subject can be repeatedly incident on the imaging apparatus 3.

In the irradiation permission state St5, after the irradiation start signal is turned on, the additional controller 61 or 61A may perform control such that the number of captured images is counted whenever the timing signal or the irradiation permission signal is transmitted. In a case where the counted number of captured images reaches a set maximum value, the additional controller 61 or 61A turns off the imaging start signal (t6) and the system 100 or 200 changes to an irradiation end state St6 as illustrated in FIG. 21.

In a case where the irradiation permission signal is counted to count the number of captured image, it is necessary to read a captured image obtained by the last emission of radiation Therefore, the timing when the reading instruction signal may be delayed or the timing signal which corresponds to one frame and is a trigger for the read operation may be further transmitted. This configuration makes it possible to eliminate the risk that imaging will be continuously performed to capture images greater than the set maximum number of images and the subject will be irradiated with unnecessary radiation and will be exposed to radiation more than necessary.

If the radiographer releases the second stage of the irradiation instruction switch 5, the irradiation instruction signal is turned off as illustrated in FIG. 22 (t7).

If the radiographer releases the first stage of the irradiation instruction switch 5, the irradiation preparation signal is turned off (t8).

If the additional controller 61 or 61A confirms that all of the input signals have been reset, the system 100 or 200 changes to the irradiation preparation state St2 illustrated in FIG. 21.

Here, "all of the signals" may be the irradiation preparation signal, the irradiation instruction signal, the imaging start signal which is the interlock of the additional controller 61 or 61A, and the irradiation start signal of the imaging apparatus 3.

If the radiographer determines that it is necessary to perform another imaging or that it is necessary to perform imaging again because the acquired captured image is not sufficient for the desired purpose as a result of the check of the captured image, the radiographer changes the state of the subject and the imaging conditions and performs imaging again according to the above-mentioned flow.

If it is determined that imaging is not necessary, the console 4 turns off the sequence start signal (t9) and ends the imaging sequence. Then, the system 100 or 200 changes to the standby state St' as illustrated in FIG. 21.

In cases other than the above-mentioned case (the determination of the radiographer), if there is no input from the radiographer for a predetermined period of time, the system may change to the standby state St1.

Operation in Case where Imaging is not Continuously Performed

The flow of the above-mentioned state change occurs in a case where imaging is continuously performed until the number of captured images reaches the maximum value. However, in some cases, imaging is not capable of being continuously performed until the number of captured images reaches the maximum value according to various situations.

For example, in a case where the radiographer wants to interrupt imaging before the number of captured images reaches the maximum value, the radiographer releases the second stage of the irradiation instruction switch 5 to turn off the irradiation instruction signal. Then, the system 100 or 200 changes from the irradiation permission state St5 to the irradiation end state St6. This is because one of a plurality of OR conditions for changing from the irradiation permission state St5 to the irradiation end state St6 illustrated in FIG. 21 (the irradiation instruction signal from the irradiation instruction switch 5 is turned off, the irradiation start signal from the imaging apparatus 3 is turned off, and the imaging start signal from the additional apparatus 6 or 6A is turned off) is established.

In the irradiation end state St6, the emission of radiation is stopped and then, for example, a process of transmitting the images remaining in the imaging apparatus 3 to the console 4 or a process of deleting the images transmitted and stored in the imaging apparatus 3 is performed similarly to a case where the number of captured images reaches the maximum value. The reason is as follows. Even if a specified number of images are not captured, the captured images may be used. In this case, the radiographer can check the captured images as in normal imaging.

It is necessary to manage the images which have not been captured to a specified number in association with the captured images. In a case where a specified number of images have not been captured, a note indicating that the specified number of images have not been captured may be added to each image or each aggregation of images and then the images or the image aggregations may be managed.

In the case where the specified number of images have not been captured, the console 4 may display information indicating that the specified number of images have not been captured on the basis of, for example, an error signal transmitted from the additional apparatus 6 or 6A.

Operation in Case where Error Occurs

There is a case where the additional apparatus 6 or 6A is disconnected from the imaging apparatus 3 during imaging.

For example, the following are considered as the cause of the disconnection:

in a case where the additional apparatus 6 or 6A and the imaging apparatus 3 are connected to each other in a wired manner, a cable is detached from a connector; and, in a case where the additional apparatus 6 or 6A is wirelessly connected to the imaging apparatus 3, radio crosstalk, a radio failure, and the cut-off of power to a wireless apparatus.

The system 100 or 200 may be configured to have a function of monitoring whether errors (error 1, error 2, error 3, and error 4) occur in each of the sequence states St3 to St6. If an error is detected, the system 100 or 200 may change to an error state St7 as represented by a dashed line in FIG. 21.

If the system changes to the error state St7, the content of the error causing the system to change to the error state St7 may be displayed on, for example, the display 43 of the console 4.

For the detection of the error, for example, an error monitoring sequence for monitoring signals in each state may be performed in parallel to the imaging sequence illustrated in FIG. 21. If an error is detected in the error monitoring sequence, the imaging sequence may be changed from the current sequence states St3 to St6 to the error state St7.

Alternatively, the operable time may be set in each of the sequence states St3 to St6 illustrated in FIG. 21. When the system changes to each of the sequence states St3 to St6, the timer may start the measurement of the time to measure the operable time in each sequence state. If the operable time in each sequence state measured by the time has elapsed, control may be performed such that the sequence state changes to the error state St7.

If an error occurs, the additional apparatus 6 or 6A or the imaging apparatus 3 that has detected the error may notify the console 4 of the occurrence of the error and the console 4 may display the occurrence of the error.

After the change to the error state St7, the sequence state is changed to the irradiation preparation state St2 or the standby state St1, using the establishment of specific conditions (for example, the reset of the error and the reset of all signals) as a trigger.

Effect

This error detection method reliably detects a defect in the apparatus or the operation, changes the system to the error state, and returns the system to the standby state St' or the irradiation preparation state St2 during the imaging sequence if necessary. Therefore, the use of the error detection method makes it possible to reliably eliminate the risk that radiation will be emitted in a state in which a defect occurs in the apparatus or the operation and the subject will be unnecessarily exposed to radiation.

Example 1

Specific examples in a case where the system 100 or 200 is achieved will be described.

Various techniques described here may also be applied to the conventional systems 100A and 200A.

Example 1: Integration of Additional Controller

Integration of Additional Controller into Radiation Control Device

In a case where the system 100 or 200 according to the above-described embodiments is installed in a medical institution such as a hospital, it is difficult to secure the place where the additional apparatus 6 or 6A is installed separately from the radiation control device 1 according to the situation of the medical institution.

There is a radiation control device 1 having a space for an additional function as an option.

Figure 23:
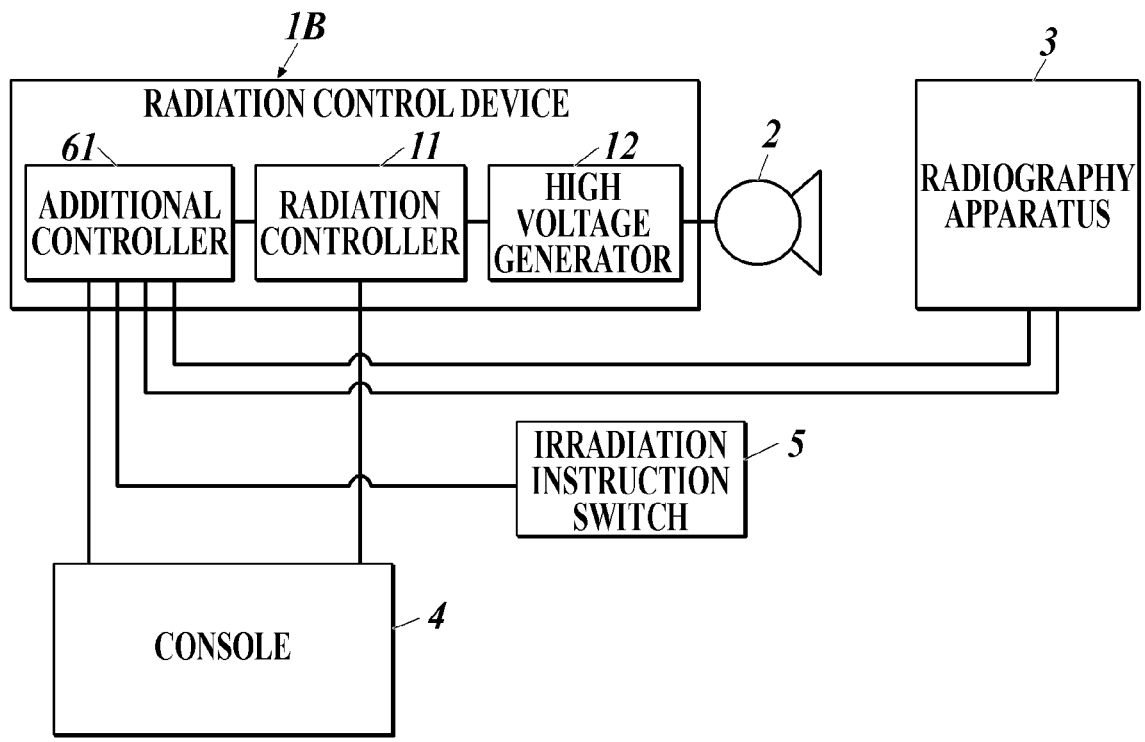
FIG. 23 is a block diagram illustrating another example of the configuration of the radiography system according to the first to fourth embodiments.

Therefore, the additional controller 61 or 61A may not be provided as the additional apparatus 6 or 6A independent of the radiation control device 1, but may be provided in a radiation control device 1B as illustrated in, for example, in FIG. 23.

For example, the additional controller 61 or 61A may be provided in the form of a substrate.

In this case, the additional apparatus 6 or 6A is not provided separately from the radiation control device 1 and the additional controller 61 or 61A or an IF (which is provided if necessary) may be added to the conventional device that captures still images such that the system 100 or 200 can perform dynamic imaging.

It is possible to reduce wiring lines which are provided around each apparatus forming the system 100 or 200 and to reduce the risk that the wiring lines will hinder imaging and errors will occur in the operation of the system 100 or 200 due to noise from the wiring lines.

Example 2: Mobile Medical Cart

Configuration in Mobile Medical Cart

Many photographers want to perform dynamic imaging not only with a radiography system that is used in a room, but also with a mobile medical car that can be used while being moved in the medical institution.

Therefore, the configuration according to the above-described embodiments may be used for the conventional mobile medical cart that captures still images. That is, the additional apparatus 6 or 6A may be provided in the housing of the mobile medical cart or may be added to the mobile medical cart such that it can be moved together with the mobile medical cart. As a result, the additional apparatus 6 or 6A can operate integrally with the mobile medical cart.

At that time, the additional controller 61 or 61A may be provided in the radiation control device 1 as described in Example 1.

This configuration makes it possible to perform dynamic imaging using the conventional mobile medical cart for capturing still images.

Example 3: Unification of Display

Input/Display of Information

In the systems 100 and 200 according to the above-described embodiments, each of the radiation control console 41 and the imaging apparatus control console 42 may have the display 43. In this configuration, if different imaging conditions are displayed on the displays 43 of the consoles 41 and 42, the photographer is not able to determine which imaging conditions are set in the radiation controller 11 or 11A or the imaging apparatus 3. In the worst case, there is a possibility that imaging will be performed under the imaging conditions that are not intended by the radiographer and the subject will be unnecessarily exposed to radiation.

Therefore, control may be performed such that the imaging conditions set in both the radiation control console 41 and the imaging apparatus control console 42 are the same and thus the same content is displayed on the displays 43 of both the radiation control console 41 and the imaging apparatus control console 42. A specific example of the control for making the imaging conditions the same will be described in the following Example 4.

As a method other than the above-mentioned method, at least one of the radiation control console 41 and the imaging apparatus control console 42 may perform a process that checks whether the imaging conditions set in both the radiation control console 41 and the imaging apparatus control console 42 or the setting contents displayed on the displays 43 of both the radiation control console 41 and the imaging apparatus control console 42 are the same, using at least one of the detection of a specific operation and the passage of a specific period as a trigger.

At least one of the result of the process and a warning may be notified, the result indicating whether the setting contents or the display contents of the radiation control console 41 and the imaging apparatus control console 42 are the same, and the warning indicating that the setting contents or the display contents of the radiation control console 41 and the imaging apparatus control console 42 are different from each other.

In this configuration, even in a case where each of the radiation control console 41 and the imaging apparatus control console 42 has the display 43, the same imaging conditions are set in both the radiation control console 41 and the imaging apparatus control console 42 or the same setting content is displayed on both the displays 43. Therefore, the radiographer can check the imaging conditions set in the entire system 100 or 200 and it is possible to perform imaging under the imaging conditions intended by the radiographer.

Example 4: Matching of Input Results

Information Cooperation

In a case where, for example, the imaging conditions can be input from both the radiation control console 41 and the imaging apparatus control console 42 as in the first and second embodiments, the input results (setting contents) of the consoles 41 and 42 need to be matched with each other.

Therefore, for example, in a case where the conditions have been changed in one of the radiation control console 41 and the imaging apparatus control console 42, the other console may be changed to the same settings by the following information cooperation methods (1) to (3).

Information Cooperation Method (1)

One of the radiation control console 41 and the imaging apparatus control console 42 is set as a master and the other console is set as a slave. Then, information is rewritten by the master and the slave only copies the information rewritten by the master.

Information Cooperation Method (2)

It is assumed that the information cooperation method is common to the radiation control console 41 and the imaging apparatus control console 42.

Alternatively, the radiation control console 41 and the imaging apparatus control console 42 are provided with timers which are synchronized with each other. If there is an input, both the time information of the timer and the content of the input are stored. Then, imaging conditions are set in both the radiation control console 41 and the imaging apparatus control console 42 in chronological order of the input.

Information Cooperation Method (3)

If information is input, the information is rewritten in both the radiation control console 41 and the imaging apparatus control console 42. Until rewriting is completed in both the radiation control console 41 and the imaging apparatus control console 42, the next input is not received or the next input is stored. If rewriting is completed, the next input is rewritten.

This configuration makes it possible to input, for example, imaging conditions from both the radiation control console 41 and the imaging apparatus control console 42. As a result, the convenience of the radiography system is improved.

It is possible to reliably match the input from one of the radiation control console 41 and the imaging apparatus control console 42 between the consoles 41 and 42.

Example 5: Permission of Irradiation after it is Checked that Settings are the Same Check of Information In the first and second embodiments in which both the radiation control console 41 and the imaging apparatus control console 42 can input conditions, such as imaging conditions, and can display, for example, the imaging conditions, in a case where the conditions of the consoles 41 and 42 are not the same and imaging is performed under the imaging conditions set in one of the two consoles 41 and 42, imaging is likely to be performed under the imaging conditions that are not intended by the radiographer.

Therefore, the radiation control console 41 and the imaging apparatus control console 42 may determine whether the recognize, set, or displayed imaging conditions are the same at a certain timing of the imaging sequence and may continue the imaging sequence in a case where they determines that the imaging conditions are the same.

If the imaging sequence is continued, information indicating that the imaging conditions are the same and there is no problem may be displayed.

In contrast, if it is determined that the imaging conditions are not the same in both the consoles, at least one of a process of performing control such that the continuation of the imaging sequence or the emission of radiation is not permitted or a process of displaying information indicating that the imaging conditions are not same may be performed.

In the above description, at least one of "the certain timings of the imaging sequence" may be, for example, the timing when the imaging conditions are set after the irradiation preparation signal is input or the timing when the check operation is performed, as illustrated in FIG. 22.

This configuration makes it possible to reliably match the imaging conditions of both the radiation control console 41 and the imaging apparatus control console 42.

In addition, it is possible to reliably eliminate the risk that imaging will be performed under the imaging conditions set in either the radiation control console 41 or the imaging apparatus control console 42 in a state in which the imaging conditions are not the same.

Example 6: Preventing Imaging Conditions from Changing after Imaging Starts

Prohibition Period of Input/Change of Information

There is a possibility that imaging which is not intended by the radiographer will be performed in a case where the imaging conditions are changed from the radiation control console 41 or the imaging apparatus control console 42 during imaging, the change being not intended by the radiographer, even though the radiographer starts imaging in a state in which the imaging conditions are input from one of the radiation control console 41 and the imaging apparatus control console 42 and other imaging conditions are satisfied, using the above-mentioned technique.

Therefore, it may be configured that the imaging conditions cannot be changed from the radiation control console 41 and the imaging apparatus control console 42 after a certain timing of the imaging sequence.

Specifically, for example, the display screen is changed to a screen other than the input screen or the input screen is grayed out such that the photographing conditions are not capable of being input.

In the above description, at least one of "the certain timings of the imaging sequence" may be, for example, the timing when the imaging conditions are set after the irradiation preparation signal is input or the timing when the check operation is performed, as illustrated in FIG. 22.

This configuration makes it possible to reliably prevent a situation in which the imaging conditions are changed during imaging and imaging is performed under the imaging conditions that are not intended by the radiographer.

Example 7: Output Through Divided Wiring Lines

Wiring Method

There is a case where the existing radiography system for connecting the additional controller 61 or 61A is modified in order to capture a still image. In addition, there is a case where the existing radiography system is modified in order to perform both still image capture and dynamic imaging.

In a case where the existing radiography system is modified in order to capture only still images, a wiring line for the timing signal is not necessary. Therefore, there is no problem. However, for example, in a case where the existing imaging table (for example, an upright imaging table or a decubitus imaging table) is used for imaging, the thickness of a wiring line that can be disposed in the apparatus to be resolved may be limited to the minimum thickness required for transmitting and receiving information for capturing a still image (for example, the thickness of a general-purpose LAN cable) due to curvature in the apparatus. If this apparatus is modified, the types of signals transmitted and received through the apparatus increase and the thickness of the wiring line increases. Therefore, there is a problem that it difficult to dispose the wiring line in the apparatus.

Figure 24:
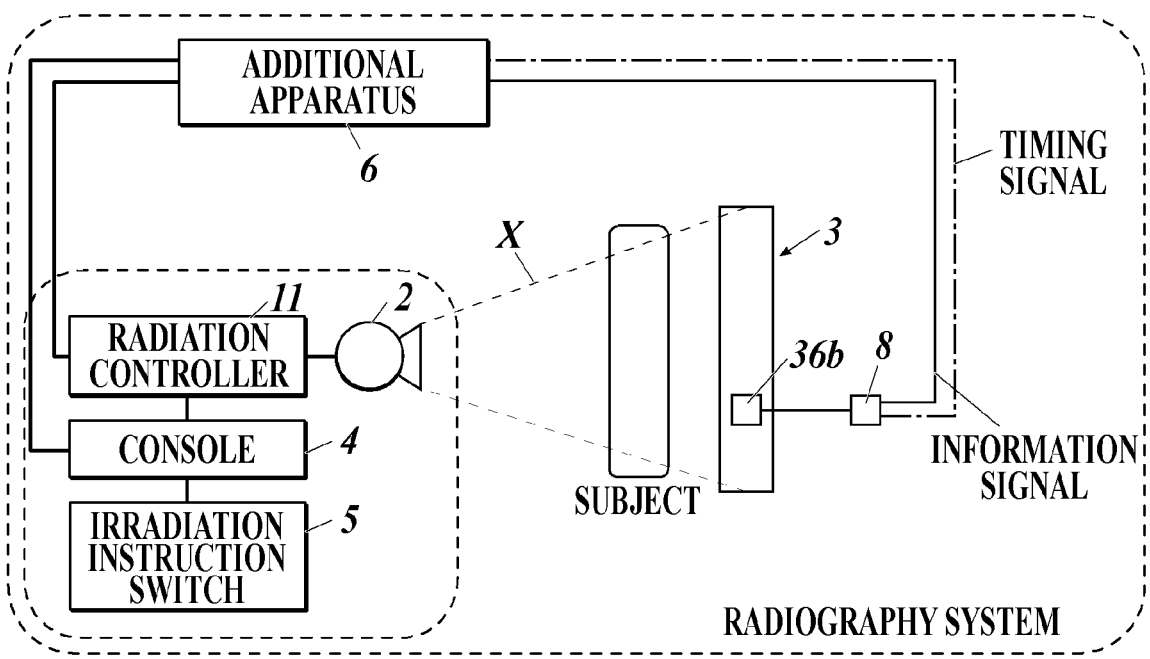
FIG. 24 is a block diagram illustrating still another example of the configuration of the radiography system according to the first to fourth embodiments.

For this reason, for example, as illustrated in FIG. 24, signals lines extending from the additional controller 61 or 61A to the imaging apparatus 3 may be divided into an information line, a power supply line, and a timing signal line and signals may be output through the divided lines.

Specifically, in a case where the conventional system is modified in order to capture only still images, the wire lines are arranged so as to be divided into two wiring lines (an information line and a power supply line).

In a case where the conventional system is modified in order to perform both still image capture and dynamic imaging, the wiring lines are arranged so as to be divided into three wiring lines (an information line, a power supply line, and a timing signal line).

In a case where the conventional system is modified in order to perform both still image capture and dynamic imaging, the wiring lines may be divided into two wiring lines, such as an aggregate of an information signal and a power supply line and a timing signal, or two wiring lines, such as an information line and an aggregate of a power supply line and a timing signal line.

In this case, in the modification for capturing still images, since the timing signal line is not necessary, it is not necessary to worry about the thickness of the wiring line.

In the modification for performing both still image capture and dynamic imaging, it is necessary to transmit and receive the timing signal, in addition to transmitting and receiving information required for still image capture and power supply. However, it is possible to easily modify the conventional system by dividing the wiring lines into two or more wiring lines and preventing an increase in the thickness of the wiring lines.

Example 8: Joining Before Wiring Lines are Connected

Joining of Wiring Lines

In some cases, the imaging apparatus 3 wirelessly transmits and receives signals and is used without a wiring line. Therefore, the imaging apparatus 3 is configured such that wiring lines for the transmission of information and the timing signal and for power supply can be attached and detached by, for example, a connector.

However, if a plurality of wiring lines are connected to the connector, the handling of the wiring lines becomes complicated. As a result, for example, the following problem occurs: a necessary wiring line is disconnected from the connector due to contact with other wiring lines and the transmission of signals is hindered, which makes it difficult to perform intended imaging.

In a case where the wiring lines to be connected are divided into an information line, a power supply line, a timing signal line, and combinations thereof, for example, as illustrated in FIG. 24, at least two or mores of the wiring lines may be joined using a joint 8 such that the number of wiring lines is less than the number of types of signals that are transmitted and received and the wiring lines may be connected to the imaging apparatus 3.

In this case, the number of wiring lines is reduced and the handling of the wiring lines is simplified. Therefore, it is possible to reduce the risk that the intended imaging will not be performed, for example, the wiring lines will be disconnected.

The wiring lines extending from the additional apparatus 6 or 6A to the imaging apparatus 3 may be divided into wiring lines required for still image capture and wiring lines required for dynamic imaging in addition to still image capture.

An example of the wiring line required for dynamic imaging in addition to still image capture is a wiring line for transmitting the timing signal.

In this case, the wiring line required for still image capture before modification can be used without any change. In a case where dynamic imaging is performed, it is possible to easily change the conventional apparatus that can capture only still images to an apparatus that can perform dynamic imaging only by adding the wiring lines required for dynamic imaging in addition to the existing wiring lines required for still image capture before modification.

Example 9: Acquisition of Information from Radiography Apparatus Through Additional Apparatus Connection of Imaging Apparatus Through Additional Apparatus Since the imaging apparatus control console 42 according to the above-described embodiments is connected to the communication network N, it can be connected to another imaging apparatus 3 (not illustrated) wirelessly or in a wired manner through the communication network.

The imaging apparatus 3 needs to be connected to the additional controller 61 or 61A in order to perform the dynamic imaging described in the first and second embodiments.

In addition, the imaging apparatus control console 42 may be configured to perform information communication for dynamic imaging with the imaging apparatus 3 through the additional controller 61 or 61A.

In this case, the imaging apparatus control console 42 acquires information related to, for example, the type of the imaging apparatus 3 from the connected imaging apparatus 3 through the additional controller 61 or 61A.

This configuration enables the additional controller 61 or 61A to reliably check whether the imaging apparatus 3 used for imaging can perform dynamic imaging.

Example 10: Display of Information Indicating Whether Dynamic Imaging is Available Display of Imaging Apparatus Capable of Performing Dynamic Imaging Since the imaging apparatus control console 42 according to the above-described embodiments is connected to the communication network N, it can be connected to another imaging apparatus 3 (not illustrated) wirelessly or in a wired manner through the communication network.

Figure 25:
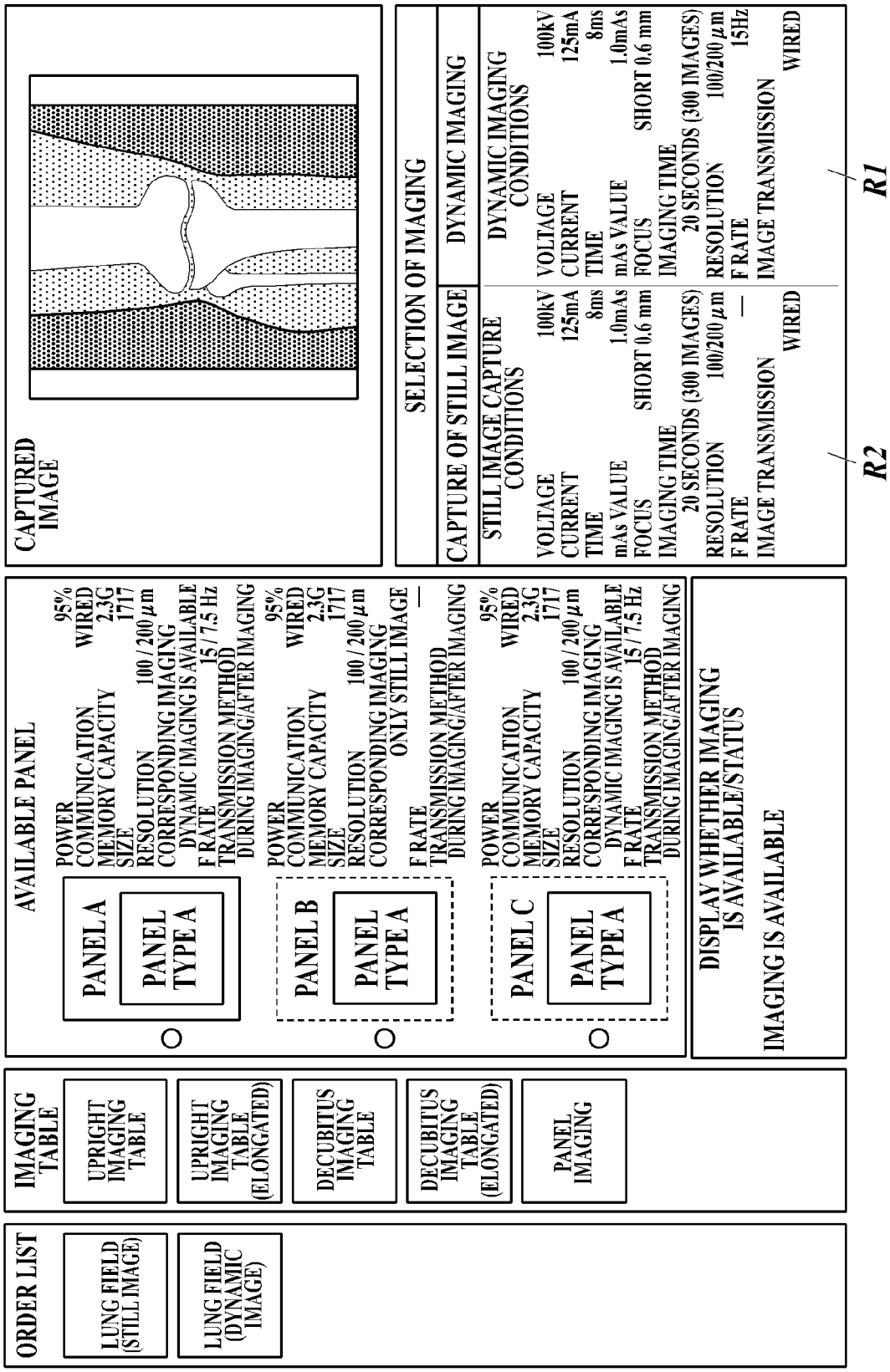
FIG. 25 illustrates an example of the display screen of the display of the console included in the radiography system according to the first to fourth embodiments.

For example, as illustrated in FIG. 25, the system may be configured such that the radiographer displays information indicating whether the connected imaging apparatus 3 can capture only still images or can capture dynamic images in addition to still images on the display 43 of the imaging apparatus control console 42.

Since information indicating whether the imaging apparatus can perform dynamic imaging is displayed on the imaging apparatus control console 42, the radiographer can easily and reliably select the imaging apparatus that can perform dynamic imaging.

It is possible to prevent a situation in which the radiographer selects the imaging apparatus that is not capable of performing dynamic imaging by mistake and performs dynamic imaging without any change.

Example 11: Change in Selection Range of Resolution and Frame Rate

Selection of Dynamic Imaging Conditions

The radiographer needs to set an appropriate resolution or an appropriate frame rate to the imaging apparatus 3 used for imaging.

For example, as illustrated in FIG. 25, an available imaging apparatus 3 and the resolution or frame rate of the imaging apparatus 3 may be displayed.

In addition, the system may be configured such that the displayed resolution or frame rate can be selected.

Figure 26:
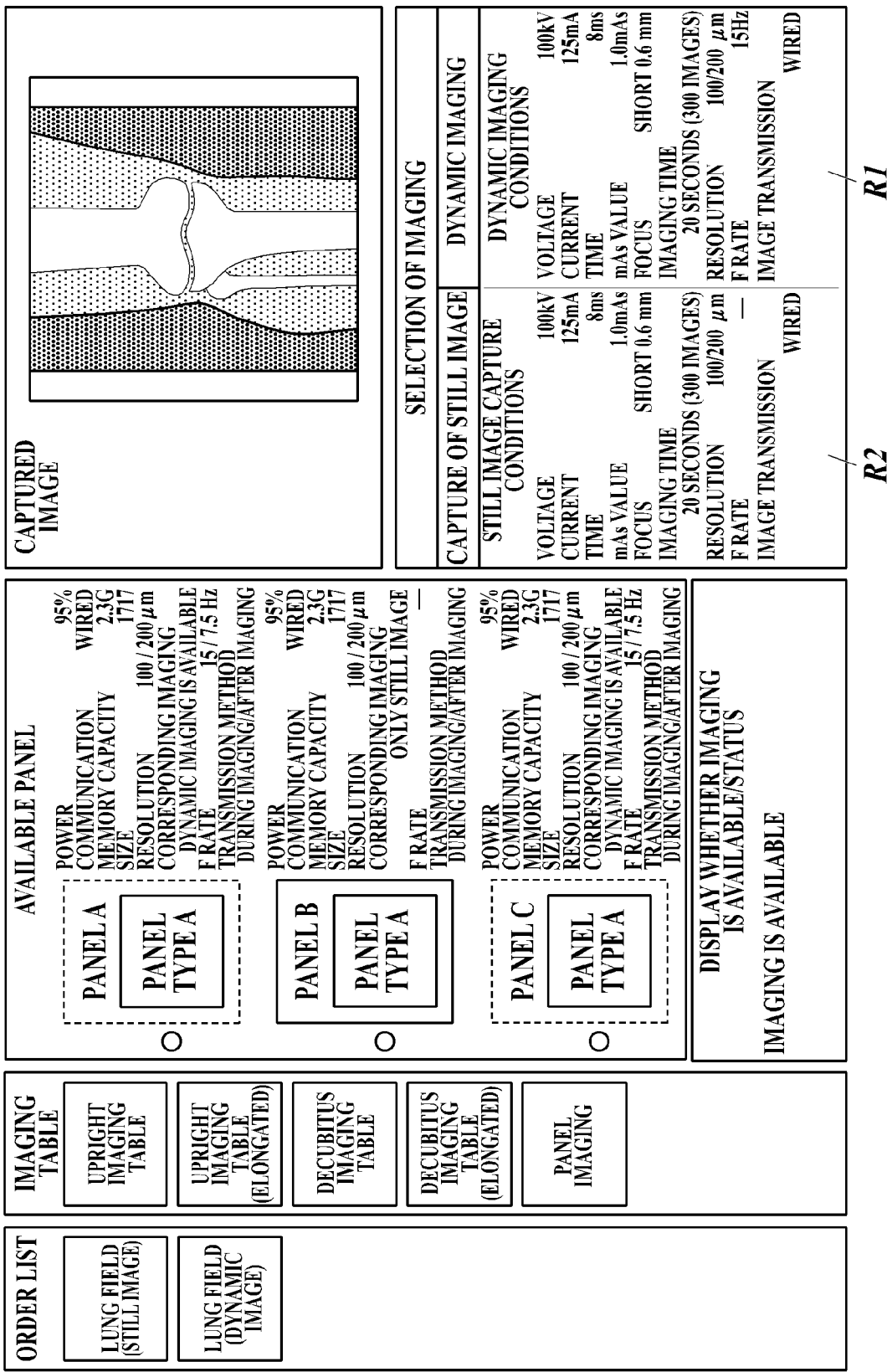
FIG. 26 illustrates an example of the display screen of the display of the console included in the radiography system according to the first to fourth embodiments.

In addition, the system may be configured as follows: in a case where the imaging apparatus 3 that corresponds to only still image capture is connected, the connected imaging apparatus 3 is displayed as an available imaging apparatus 3 and, for example, the condition setting regions R1 and R2 of an unavailable imaging apparatus 3 are grayed out such that the unavailable imaging apparatus 3 is not selectable as illustrated in FIG. 26; even in a case where the unavailable imaging apparatus 3 is selected, the setting of the unavailable imaging apparatus 3 is not permitted; or imaging is not permitted.

Further, the system may be configured such that, in addition to the resolution and the frame rate, for example, information indicating whether a binning process can be performed, an image transmission method, and the exposure time are displayed. In addition, the system may be configured such that one of the items can be selected.

Example 12: Switching Between Still Image Capture and Dynamic Imaging

Switching Between Still Image Capture and Dynamic Imaging

The radiographer selects one of still image capture and dynamic imaging at the right time according to the situation. Therefore, the radiography system needs to have a configuration capable of switching between still image capture and dynamic imaging.

For example, a method can be used which switches a control method between still image capture and dynamic imaging Specifically, in a case where still image capture is selected, the control of the additional controller 61 or 61A is switched such that still image capture is performed. In a case where dynamic imaging is selected, the control of the additional controller 61 or 61A is switched such that dynamic imaging is performed.

The system may be configured such that whether still image capture is currently selected or dynamic imaging is currently selected as illustrated in FIG. 26. In addition, the system may be configured such that the display is switched.

For example, if still image capture is selected, it is possible to display that still image capture is selected by graying out the condition setting region R1 of dynamic imaging on the display 43, as illustrated in FIG. 26.

In a case where the selected imaging apparatus 3 is the imaging apparatus 3 corresponding to dynamic imaging and the grayed-out condition setting region R1 of dynamic imaging is selected, the imaging method is switched to dynamic imaging. In addition, the graying-out of the condition setting region R1 is removed and the still image capture condition setting region R2 is grayed out to display that dynamic imaging is selected, which is not illustrated.

The condition setting regions R1 and R2 can be selected by, for example, moving a pointer displayed on the screen to the condition setting region R1 or R2 of the desired imaging with the mouse and clicking the condition setting region with the mouse. Alternatively, in a case where the display 43 is a touch panel screen, the system may be configured such that the radiographer touches the condition setting region R1 or R2 of the desired imaging to select the condition setting region.

At that time, the system may be configured as follows: the imaging conditions of each of still image capture and dynamic imaging are stored; and, in a case where still image capture or dynamic imaging is selected, the imaging conditions of the selected imaging are automatically set. In addition, the imaging conditions of each of still image capture and dynamic imaging may be values that have been preset according to the imaging technique or may be values that have been changed and input by the radiographer.

In this configuration, for example, if the radiographer sets the imaging conditions of still image capture and selects dynamic imaging, the imaging conditions of dynamic imaging are displayed and set. The system may be configured such that, if the radiographer selects still image capture again, the imaging conditions of still image capture before dynamic imaging is selected are set and displayed.

In addition, in the setting of dynamic imaging, the maximum number of images to be captured may be set to one to switch to the control of still image capture.

In this configuration, even if there is one radiography system, it is possible to perform both still image capture and dynamic imaging according to the radiographer's selection.

Example 13: Reset by Pressing Irradiation Instruction Switch to First Stage

Start Timing of Reset Operation

The reset operation consumes power. Therefore, if the reset operation is repeated after the imaging sequence starts, power consumption increases. In particular, in a case where the imaging apparatus 3 is driven by a built-in battery, a dead battery problem occurs.

Figure 27:
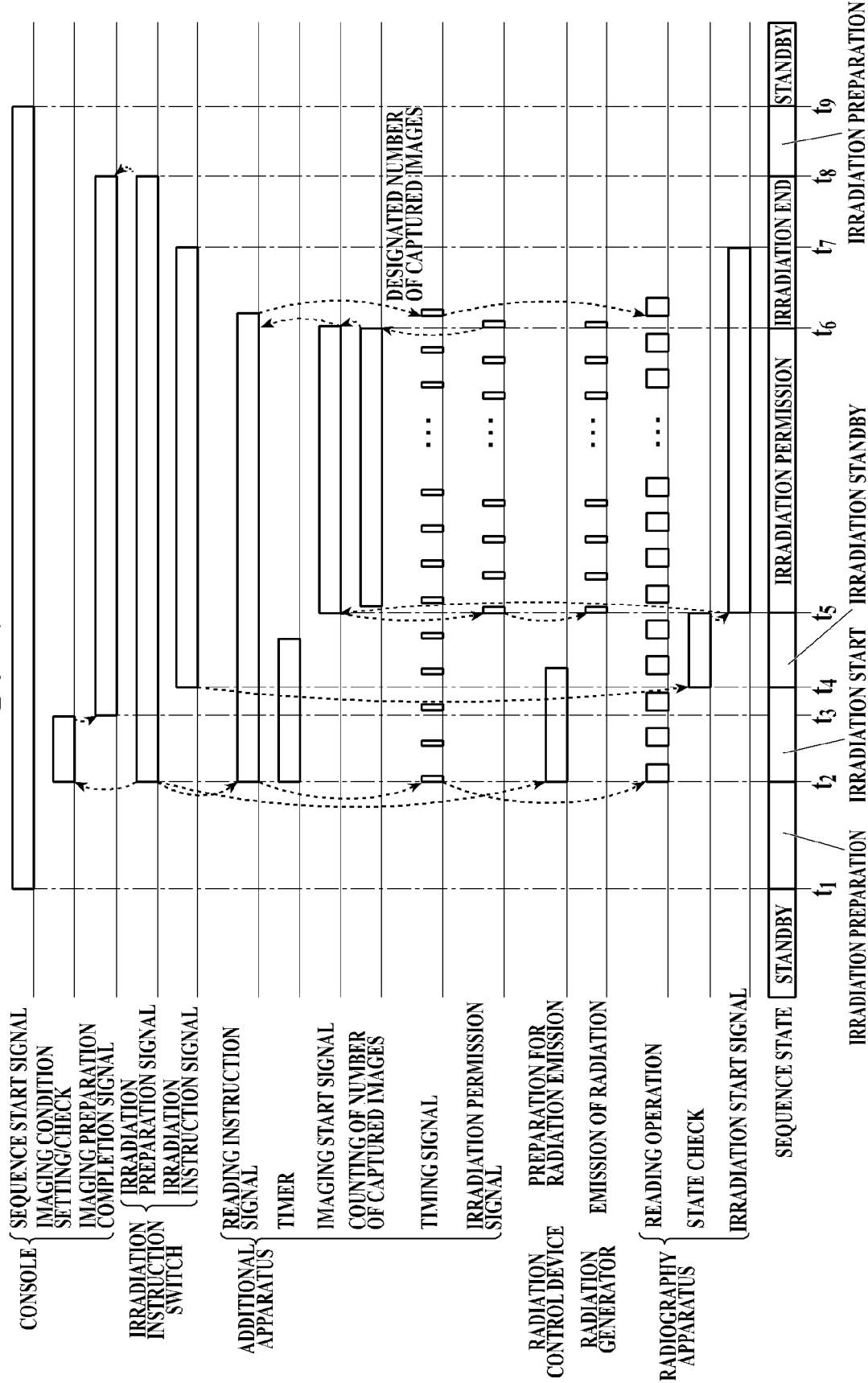
FIG. 27 is a timing chart illustrating the operation of the radiography system according to the first to fourth embodiments.

Therefore, for example, the reset operation (reading operation) may start after the irradiation preparation signal is turned on as illustrated in FIG. 27.

The system may be configured as follows. The timing signal is output before the irradiation preparation signal is transmitted and the reading instruction signal different from the timing signal is transmitted to the imaging apparatus 3. If the imaging apparatus 3 receives the reading instruction signal, it performs the reading operation in response to the timing signal, which is not illustrated.

This configuration makes it possible to prevent an increase in the power consumption of the imaging apparatus 3.

Example 14: Start of Dynamic Imaging Period after Stop of Reset

Imaging Start Timing

The reset operation of the imaging apparatus 3 is performed by scanning each of the pixels of the light receivers arranged in a matrix on the surface of a built-in substrate. Therefore, if imaging starts during the reset operation, some of the light receivers have completed the reset operation, but the remaining light receivers receive radiation in a state in which the reset operation has not been completed. As a result, in some cases, there is a difference in density distribution between a portion in which the reset operation has been completed and a portion in which the reset operation has not been completed in the radiographic image.

Therefore, it is preferable to start imaging from a state in which the reset operation is uniformly performed on all of the light receivers of the imaging apparatus 3.

Specifically, the imaging apparatus 3 is configured to have a function of transmitting the irradiation start signal to the additional apparatus 6 or 6A at the timing when the scanning of all of the pixels of the light receivers is completed after the reset operation starts.

Then, the additional apparatus 6 or 6A receives the irradiation start signal at the timing when the reset operation is uniformly performed, turns on the imaging start signal which is an interlock, and repeatedly transmits the irradiation permission signal to the radiation controller 11 or 11A.

According to this configuration, it is possible to reliably prevent a situation in which imaging is performed in a state in which the reset operation is not uniformly performed for the light receivers and there is a difference in density distribution between a portion in which the reset operation has been completed and a portion in which the reset operation has not been completed in the radiographic image.

Example 15: Determination of Whether Imaging Apparatus is in Irradiation State on Basis of Difference in Timing Signal Signals when Radiation is not Emitted/when Radiation is Emitted It is difficult for the imaging apparatus 3 to determine whether the reading operation is performed as the reset operation (while radiation is not emitted) or as imaging (while radiation is emitted) on the basis of only the timing signal. As a result, it is difficult to determine whether to store the read image as the captured image.

For this reason, the timing signal for the reset operation may be different from the timing signal for imaging.

Figure 28:
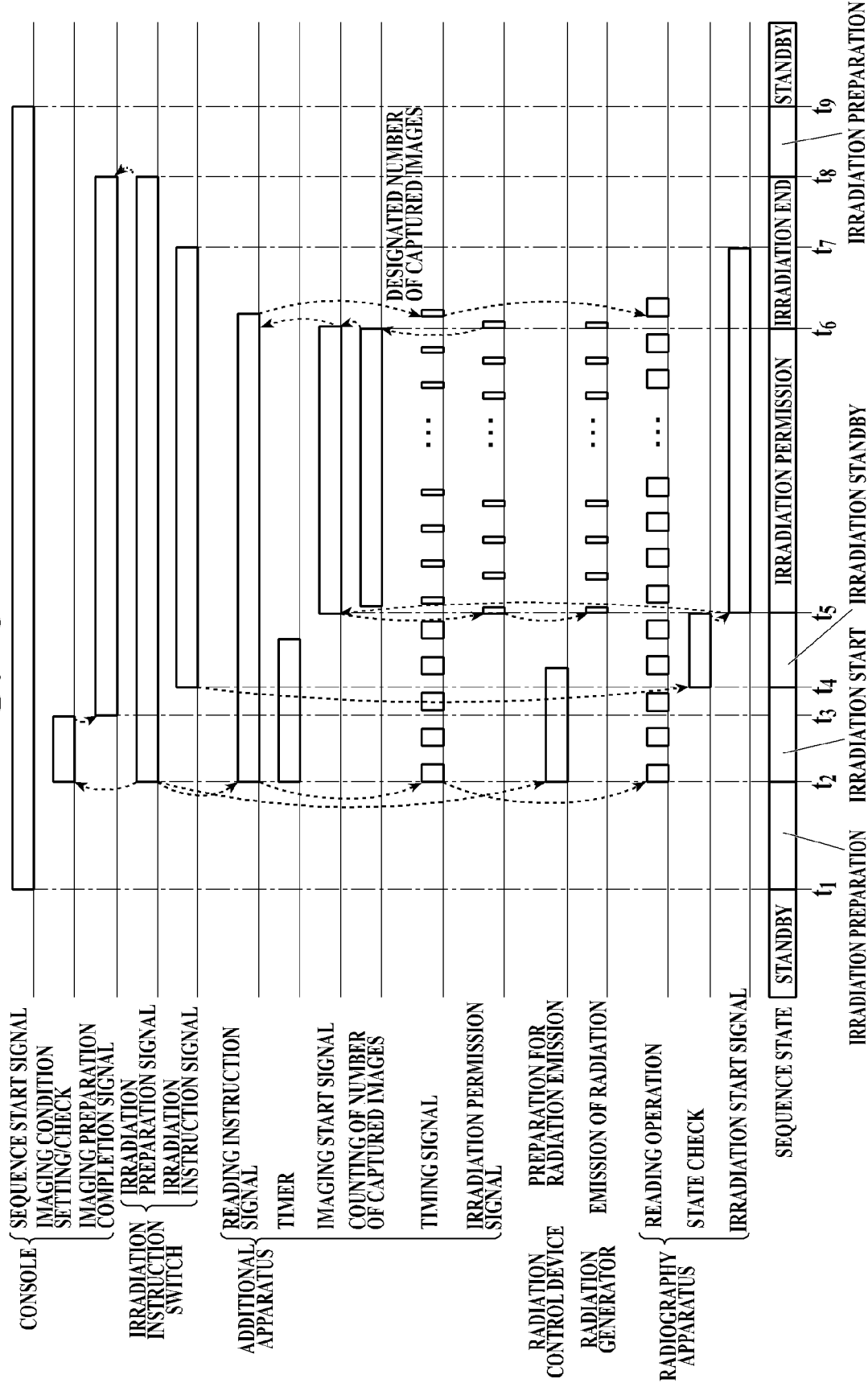
FIG. 28 is a timing chart illustrating the operation of the radiography system according to the first to fourth embodiments.

Specifically, for example, there is a method which changes the pulse widths of the timing signal for the reset operation and the timing signal for imaging as illustrated in FIG. 28. Even in a case where the pulse width of the signal is changed, the reset operation or imaging can be performed at the exact timing if the reset operation or imaging is performed in accordance with the start of the reading operation and the rise of the pulse signal.

This configuration makes it possible for the imaging apparatus 3 to determine whether the reading operation is performed as the reset operation or as imaging on the basis of the timing signal. Therefore, it is possible to reliably eliminate the risk that, even though the timing signal is received during the emission of radiation, the reading operation to be performed will be erroneously determined to be the reset operation and the read captured image will be discarded.

Example 16: Input of Standby Time after Irradiation Preparation Signal is Received Standby Time In some cases, the interval between the pressing of the irradiation instruction switch 5 to the first stage (the output of the irradiation preparation signal) and the pressing of the irradiation instruction switch 5 to the second stage (the output of the irradiation instruction signal) is short depending on the radiographer. Further, in some cases, the signals output from the irradiation instruction switch 5 are not divided into the irradiation preparation signal and the irradiation instruction signal and the irradiation preparation signal and the irradiation instruction signal are input as the same signal, depending on the apparatus configuration. In this case, there is a possibility that dynamic imaging will start while imaging preparations, such as the rotation of the rotating anode, the warm-up of the imaging apparatus 3 by the reset operation of the imaging apparatus 3, and image uniformization, are insufficient.

This may not cause any problem in a case where one still image is captured. However, in the case of dynamic imaging, for example, the obtained dynamic image may be analyzed using a difference in signal value between a plurality of images captured at different imaging times and the frame may be changed with a change in the state of the imaging apparatus 3 during dynamic imaging, which causes a problem.

Therefore, a timer may be provided in the additional apparatus 6 or 6A and the timer may start to measure time in a case where the irradiation preparation signal is received. In a case where a predetermined standby time does not elapse from the start of the timer, the irradiation permission signal may not be output even though the irradiation instruction signal is input.

This configuration makes it possible to sufficiently perform, for example, the reset operation of the imaging apparatus 3 for the standby time. Since a change in the temperature of the imaging apparatus 3 after a warm-up is sufficiently performed is small, it is possible to prevent a change of the frame due to a change in the state of the imaging apparatus 3 during the dynamic imaging.

Example 17: Setting of Standby Time of Additional Apparatus to be Longer than Standby Time of Radiation Controller Setting of Standby Time Some radiation controllers 11 and 11A have a function that does not transmit the irradiation signal until a predetermined standby time elapses in a case where the interval between the reception time of the irradiation preparation signal and the reception time of the irradiation instruction signal is short.

In a case where the system 100 or 200 is formed by the above-mentioned radiation controller 11 or 11A and the additional apparatus 6 or 6A having the function described in Example 16, the standby time set in the additional apparatus 6 or 6A may be longer than the standby time of the radiation controller 11 or 11A.

This configuration makes it possible to set the standby time considering the standby time required for the imaging apparatus 3 and the standby time required for the emission of radiation.

The standby time set in the radiation controller 11 or 11A may be zero and the necessary standby time may be delayed by the additional apparatus 6 or 6A.

In a case where the standby time set in the radiation controller 11 or 11A, only the delay of radiation is considered. However, the above-mentioned configuration makes it possible to set the standby time in the additional controller 61 or 61A, considering the standby time required for the imaging apparatus 3 and the standby time required for the emission of radiation.

Example 18: Standby Time is Set in Only Capture of First Image

Timing of Standby Time

In dynamic imaging, the standby time is required when the apparatus starts up. The standby time is required for only the capture of a first image and it is not necessary to set the standby time for the capture of the second and subsequent images.

Therefore, the system may be configured such that the standby time is set for only the capture of the first image and is not set for the capture of the second and subsequent images.

This configuration makes it possible to set the standby time required for only the capture of the first image in the imaging apparatus 3 and the emission of radiation.

Example 19: End of Imaging at Set Maximum Number of Captured Images

Stop of Imaging at Designated Number of Captured Images

There is a problem that the subject is unnecessarily exposed to radiation in a case where the radiographer continues to input an instruction to emit radiation (presses the irradiation instruction switch 5 to the second stage) and imaging is performed such that the number of captured images is greater than a predetermined maximum value.

Therefore, the system may be configured such that at least one of the additional controller 61 or 61A, the imaging apparatus 3, and the radiation controller 11 or 11A has a function of counting the number of captured images.

In addition, the system may be configured such that at least one (which may be the same as or different from the component having the count function) of the additional controller 61 or 61A, the imaging apparatus 3, and the radiation controller 11 or 11A has a function which compares the counted number of captured images with a predetermined maximum value and transmits information indicating that the counted number of captured images has reached the maximum value to at least one of the additional controller 61 or 61A, the imaging apparatus 3, and the radiation controller 11 or 11A (including a case where the information is transmitted in the same controller) if the counted number of captured images reaches the maximum value.

The additional controller 61 or 61A is configured to have a function that turns off the imaging permission signal and stops the output of the irradiation permission signal if it has received information indicating that the number of captured images has reached the maximum value.

It is preferable that the reading instruction or the timing signal for reading is further output for the capture of at least one image after the number of captured images reaches the maximum value. The reason is that, in a case where the number of times radiation is emitted is counted, it is necessary to read the image obtained by the last emission of radiation and to store the read image. In a case where the completion of reading is counted, this function is not necessary.

According to this configuration, since imaging ends reliably after the capture of the required number of images is completed, it is possible to prevent the subject from being unnecessarily exposed to radiation.

Example 20: Imaging is Continued after Irradiation Instruction, Number of Captured Images, and Presence of Failure are Checked End of Imaging For example, in a case where the instruction to emit radiation is interrupted, a case where the capture of a predetermined maximum number of images has been completed, or a case where a defect occurs in the apparatuses forming the radiography system or the control state of them, if imaging is continued, there is a problem that imaging is continued in a state which is not intended by the radiographer and the subject is unnecessarily exposed to radiation.

Therefore, the system may be configured to monitor at least one of whether the instruction to emit radiation is continuously issued (the pressing of the irradiation instruction switch 5 to the second stage is continued), whether the number of captured images is equal to or less than a predetermined maximum value, and whether a defect occurs in the apparatuses or the control state and to perform at least one of a process of interrupting imaging, a process of transmitting information indicating that there is a problem, and a process of displaying the information indicating that there is a problem if it is determined that there is a problem.

For example, this monitoring operation may be performed using control for changing the sequence state illustrated in FIG. 21.

A monitoring sequence different from this control may be simultaneously operated to perform the monitoring. In this case, since a double check is possible, it is possible to more reliably detect the occurrence of a problem.

This configuration makes it possible to prevent the subject from being unnecessarily exposed to radiation due to imaging performed in a state which is not intended by the radiographer.

The above-mentioned monitoring operation may be performed before the irradiation permission signal is transmitted first or before each irradiation permission signal that is repeatedly transmitted is transmitted.

In this case, it is possible to perform the above-mentioned determination in a state immediately before the irradiation permission signal for permitting the emission of radiation is transmitted. Therefore, it is possible to prevent radiation from being emitted (imaging from being performed) in a state that is not intended by the radiographer.

The invention is not limited to, for example, the above-described embodiments and may be appropriately changed without departing from the scope and spirit of the invention.

For example, it is possible to modify a radiation generation apparatus which has already been introduced into a medical institution and can perform only one radiation emission operation in response to one radiation emission instruction with the technique described in the invention such that the radiation generation apparatus can perform dynamic imaging.

Alternatively, the technique described in the invention may be combined with a radiation generation apparatus which can perform only one radiation emission operation in response to one radiation emission instruction to easily construct a new system that can perform dynamic imaging.

Example 21

Commonalization of Low-Frame-Rate and High-Frame-Rate Imaging Operations

In a case where the operation of the imaging device 3 varies depending on the set imaging frame rate, if dynamic imaging is performed, there is a problem that a captured image obtained after the lapse of a predetermined time from the start of imaging is different in high-frame-rate imaging and low-frame-rate imaging.

For example, the number of frames captured until a predetermined time elapses from the start of imaging is different between a case where imaging is performed at a high frame rate and a case where imaging is performed at a low frame rate. Therefore, there is a problem that, for example, a change in the temperature of the imaging apparatus 3 associated with the imaging operation is different in high-frame-rate imaging and low-frame-rate imaging, which results in a difference in image quality between images.

This causes the following problem. For example, in a case where a change in the size of a region of interest, such as a tumor, is observed in detail on the basis of the images captured by high-frame-rate imaging immediately after surgery and the postoperative course is checked on the basis of the images captured by low-frame-rate imaging in order to reduce an exposure doze, if the images are changed due to a difference between the imaging modes, there is a problem that it is difficult to compare the postoperative course with that immediately after surgery.

In order to solve the above-mentioned problems, the imaging frame rate set in the imaging apparatus 3 may not be changed in a case where imaging is performed while the irradiation frame rate is changed. That is, even in a case the radiation emission period of the generation apparatus increases, the imaging apparatus 3 repeats the imaging operation with the same period. At that time, in a case where imaging is performed in the low-frame-rate mode, unexposed frames are extracted from the captured frames and a dynamic image formed by the extracted unexposed frames is generated.

In this configuration, since the influence of a temperature rise after the lapse of a predetermined time from the start of imaging is the same, it is possible to acquire images with the same quality at the same temperature even at different irradiation frame rates.

Example 22

Change in Period for which Radiation can be Emitted

The imaging apparatus 3 sequentially reads an exposed image generated at the timing when radiation is emitted from the pixels at the end of the radiation detector 32 to acquire an image. If a part of the emission of radiation is performed while charge is sequentially read from the pixels at the end of the radiation detector 32, a part of the radiographic image generated by the read operation may become a part of the image of the next frame. Therefore, the radiation emission time is limited to the period for which the reading operation of the imaging apparatus 3 is not performed.

However, since a radiation emission window that is the period for which radiation can be emitted is shorter in imaging with a high imaging frame rate, it is difficult to complete the emission of radiation within the radiation emission window. In particular, in the emission of pulsed radiation, there is a wave tail in which the emission of radiation remains in the second half of the pulse and it is difficult to put the wave tail into the radiation emission window.

In order to solve the problems, for example, the length of the radiation emission window may be changed according to whether to perform the thinning-out emission of radiation as illustrated in FIGS. 29A and 29B. In particular, in a case where the thinning-out emission of radiation is performed, the radiation emission window may be longer than that in a case where the thinning-out emission of radiation is not performed, as illustrated in FIG. 29B.

In this case, since there is enough time from the rising to the falling of pulsed radiation, it is easy to put the wave tail of radiation into the radiation emission window.

In thinning-out irradiation, even if the wave tail is not put into the radiation emission window, it is removed by the reading of the next thinned-output image. Therefore, even if the emission time of radiation is long, it is possible to remove the influence of the wave tail on the frame for capturing the next emission of radiation.

Example 23

Change in Transmission Period

The dynamic imaging has a problem that, after an image is read, the transmission of the image may not be completed until the next accumulation.

In order to solve the problem, the image generated at the timing when no radiation is emitted may not be transmitted and may be stored in the imaging apparatus 3 or may be deleted from the imaging apparatus 3.

Figure 30:
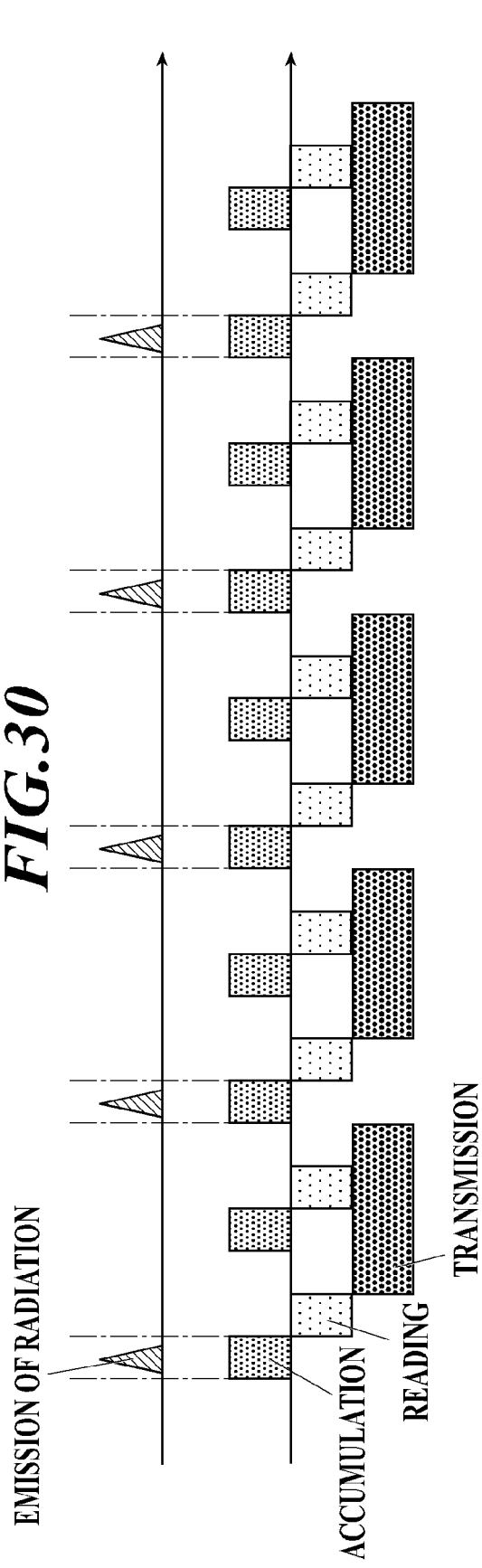
FIG. 30 is a timing chart illustrating the operation of a radiography system according to an example of the first to fourth embodiments.

For example, as illustrated in FIG. 30, the image generated at the timing when radiation is emitted is transmitted using at least a part of the accumulation and reading period of the timing when no radiation is emitted.

This configuration makes it possible to extend the transmission time of the image generated at the timing when radiation is emitted and to stably transmit the image.

In addition, it is possible to increase all of the frame rates.

Example 24

Imaging Timing Control (1)

In a case where imaging is performed for a part of the irradiation instruction signal input period and the period from the time when the radiographer presses the irradiation instruction switch to the second stage to the time when imaging starts actually is long, there is a problem that it may be difficult to capture the dynamics desired by the radiographer.

Figure 31:
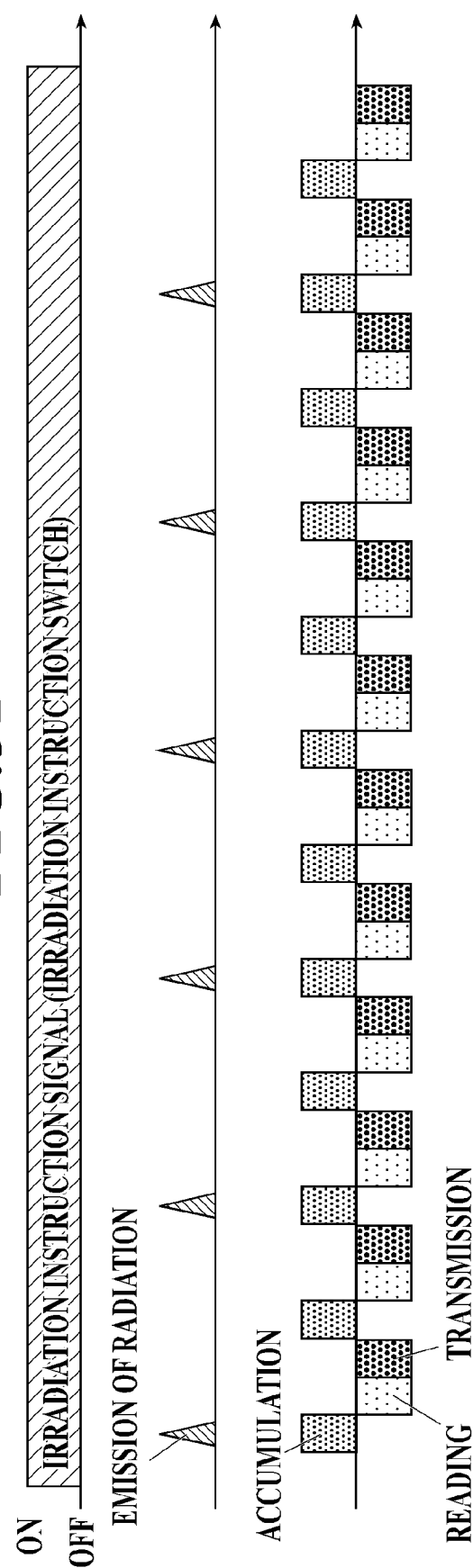
FIG. 31 is a timing chart illustrating the operation of a radiography system according to an example of the first to fourth embodiments.

In order to solve the problem, in a case where imaging is performed for a part of the irradiation instruction signal input period, for example, imaging (the emission of radiation/accumulation) may be performed at the timing when the first image can be captured after the radiographer instructs imaging, as illustrated in FIG. 31.

In this case, since imaging is performed as soon as possible after the radiographer instructs imaging, it is possible to start imaging at the timing when the radiographer wants to perform imaging and to reduce the risk that the radiographer will not take the desired images of the dynamics.

Example 25

Imaging Timing Control (2)

Before the imaging apparatus 3 starts imaging, it needs to perform, for example, a reset operation or a warm-up. In some cases, it is desirable to capture an image at a timing as late as possible in order to obtain a stable image.

In order to solve the problem, in a case where imaging is performed for a part of the irradiation instruction signal input period, for example, imaging is not performed at the timing when the first image can be captured after the radiographer instructs imaging, but may be performed at other imaging timings, such as the timing after the second and subsequent images are captured, as illustrated in FIG. 32.

For example, in the case of imaging in which the generation apparatus emits radiation once whenever the imaging device 3 performs N imaging operations (N=2 in FIG. 32), imaging is performed at the N-th timing when imaging can be performed after the radiographer instructs imaging.

In this case, imaging is performed at a later timing after the radiographer instructs imaging. Therefore, the imaging apparatus 3 can sufficiently perform, for example, the reset operation or a warm-up and can start imaging in a stable state. As a result, it is possible to improve the quality of a captured image.

Example 26

Standby Time Before Imaging Starts

Before starting imaging, the imaging apparatus 3 needs to perform, for example, a reset operation or a warm-up. In some cases, it is desirable to capture an image at a timing as late as possible in order to obtain a stable image.

In order to solve the problem, the delay time may be provided such that at least one of the imaging apparatus 3, the additional controller 61, the console 4, and the radiation controller 11A starts an imaging operation after the lapse of a predetermined time from the pressing of the irradiation instruction switch to the first or second stage.

In a case where imaging is performed in the dynamic imaging mode, the delay time may be longer than that in a case where imaging is performed in the still image capture mode.

The generation of an image may start after radiation is emitted several times for system stability in the initial stage of the imaging operation. In this case, the imaging apparatus 3 may be configured not to perform imaging in a case where radiation is emitted several times in the initial stage.

The emission of radiation may be suppressed by the radiation generator, the periphery thereof, or a collimator attached to the radiation generator 2 such that the subject is not irradiated with radiation in a case where radiation is emitted several times in the initial stage. As a method for suppressing the emission of radiation, for example, the following configuration may be used: a suppression plate that is less likely to transmit radiation is provided in the radiation generator 2, the periphery thereof, or the collimator attached to the radiation generator 2 so as to be movable; and, in a case where radiation is emitted several times in the initial stage, the suppression plate is moved on a radiation emission axis to block radiation generated from the radiation generator 2 such that the emission of radiation to the surroundings is suppressed. After radiation is emitted several times in the initial stage, for example, the suppression plate is retracted from the irradiation axis. After the initial stage, it is possible to irradiate the subject with radiation to capture the image of the subject.

In this case, imaging is performed at a later timing after the radiographer instructs imaging. Therefore, the imaging apparatus 3 can sufficiently perform, for example, the reset operation or a warm-up and can start imaging in a stable state. As a result, it is possible to improve the quality of a captured image.

Example 27

Method for Capturing Variation

There is an imaging method that focuses on a variation at a certain point of time of the dynamics, depending on the imaging technique. For example, in a case where an image of a blood flow is captured, it is not necessary to repeat imaging over a long period of time and it is preferable to obtain a plurality of (two or more) consecutive captured images at the moment when the image of a blood flow is desired to be captured.

However, in a case where it is difficult to acquire only the images before and after the necessary timing (imaging needs to always be repeated at the same timing), the subject is unnecessarily exposed to radiation.

In order to solve the problem, only necessary imaging may be performed at the timing when a variation is required or at the timing when only a plurality of consecutive captured images are required.

For example, as illustrated in FIG. 33, the imaging apparatus 3 is configured to repeatedly perform accumulation and reading with a predetermined period and the generation apparatus is configured to emit radiation only at a certain number of consecutive imaging timings.

According to this configuration, a plurality of consecutive captured images obtained by the emission of radiation are compared with each other to acquire a variation in the state of the subject for a predetermined period including the imaging time of a specific image.

For example, in a case where the image of a blood flow is captured, as illustrated in FIG. 33, a plurality of images are continuously captured at a specific timing and a change in the images is analyzed to check a blood flow at the imaging timing. In addition, it is possible to check the state of the blood flow at the imaging timing from the difference between a plurality of consecutive images.

In FIG. 33, two consecutive images are captured and a variation for the period from the capture of a first image to the capture of a second image is acquired. However, a variation for the period from the capture of a first image to the capture of a plurality of images may be acquired from three or more images captured at the right time. The calculation of a variation from three or more images makes it possible to reduce, for example, noise.

Further, unlike the case illustrated in FIG. 33, if the imaging apparatus emits radiation at all timings when it can accumulate charge, the subject is exposed to radiation that is twice as much as the necessary amount of radiation. However, as illustrated in FIG. 33, the emission of radiation is thinned out at an unnecessary timing, which makes it possible to reduce an exposure dose while obtaining necessary information.

Example 28

Variable Frame Rate

In some cases, a necessary frame rate is changed during imaging, depending on the imaging technique.

However, it is difficult for the imaging apparatus 3 according to the related art to change the imaging frame rate during imaging Therefore, the imaging apparatus 3 according to the related art needs to perform accumulation and reading at a constant imaging frame rate and to emit radiation at a constant irradiation frame rate. As a result, the imaging apparatus 3 according to the related art emits radiation even in an unnecessary frame and the subject is unnecessarily exposed to radiation.

In order to solve the problem, for example, as illustrated in FIG. 34, imaging may be performed while the interval at which thinning-out is performed is changed at any imaging timing.

In this case, the imaging apparatus 3 may be configured to perform imaging at a constant imaging frame rate. Thereafter, only the image captured at the timing when radiation is emitted is selected to obtain an image captured at a changed frame rate.

This configuration makes it possible to use the imaging apparatus 3 according to the related art which is designed for a specific frame rate. The imaging apparatus 3 that performs imaging at a specific frame rate can be started up faster than a special imaging apparatus that can change the frame rate and can continue imaging stably.

In addition, it is possible to perform radiography only at a necessary frame rate by changing the timing when the emission of radiation is thinned out during imaging. It is possible to prevent the subject from being unnecessarily exposed to radiation.

Example 29

Control by External Signal

The start timing of imaging and the timing when the frame rate is changed are determined by the dynamics of the subject or the operation of the imaging apparatus and the imaging system. For example, in an imaging technique that needs to change the start timing of imaging and the frame rate according to the operation state of the radiation generator, such as tomosynthesis which will described below, it is necessary to change the start timing of imaging and the timing when the frame rate is changed according to the operation of the apparatuses in the imaging system.

However, it is difficult for the radiographer to appropriately determine the start timing of imaging and the timing when the frame rate is changed while monitoring the dynamics of the subject and the operation of the imaging apparatus and the imaging system. For this reason, it is desirable to start imaging or change the frame rate using a measurement device that quantitatively measures dynamics or a detector that detects the start of a predetermined operation of the imaging apparatus 3.

In order to solve the problem, the system may be configured such that imaging conditions, such as the start of imaging and a change in the frame rate, are changed by an external trigger.

For example, a heart rate monitor attached to the subject, an auto voice that instructs the operation of the subject, and a signal from the radiation control device 1 that controls the operation of the tube can be used as the external trigger.

This configuration makes it possible to start imaging or to change the frame rate at an appropriate timing, using a measurement device that quantitatively measures dynamics or a detector that detects the start of a predetermined operation of the imaging apparatus 3.

Example 30

Application Examples to Tomosynthesis and the Like

In an imaging method that performs imaging while moving the radiation generator 2 at a constant speed to generate a tomographic image, such as tomosynthesis, an image captured in a state in which the inclination of the radiation emission axis with respect to the axis orthogonal to the radiation incident surface 3a of the imaging apparatus 3 is large has little influence on the tomographic image. Therefore, in imaging that generates the tomographic image, in some cases, it is desirable to reduce the imaging frame rate while the inclination of the radiation emission axis is large and to increase the imaging interval.

In contrast, in a case where the radiographer wants to obtain a precise tomographic image, the image captured in a state in which the inclination of the radiation emission axis with respect to the axis orthogonal to the radiation incident surface 3a of the imaging apparatus 3 is large has a relatively large influence on the tomographic image. Therefore, contrary to the above-mentioned case, in some cases, it is desirable that the imaging interval is reduced while the inclination of the radiation emission axis is large and the imaging frame rate is reduced to increase the imaging interval while the inclination of the radiation emission axis is small.

However, the radiography control apparatus according to the related art performs imaging while emitting radiation at equal intervals. Therefore, there is a problem that the subject is unnecessarily exposed to radiation.

In order to solve the problem, a method that changes the irradiation frame rate according to the inclination of the radiation emission axis with respect to the radiation incident surface, that is, the thinning-out of radiation illustrated FIG. 34, may be performed.

Figure 35:
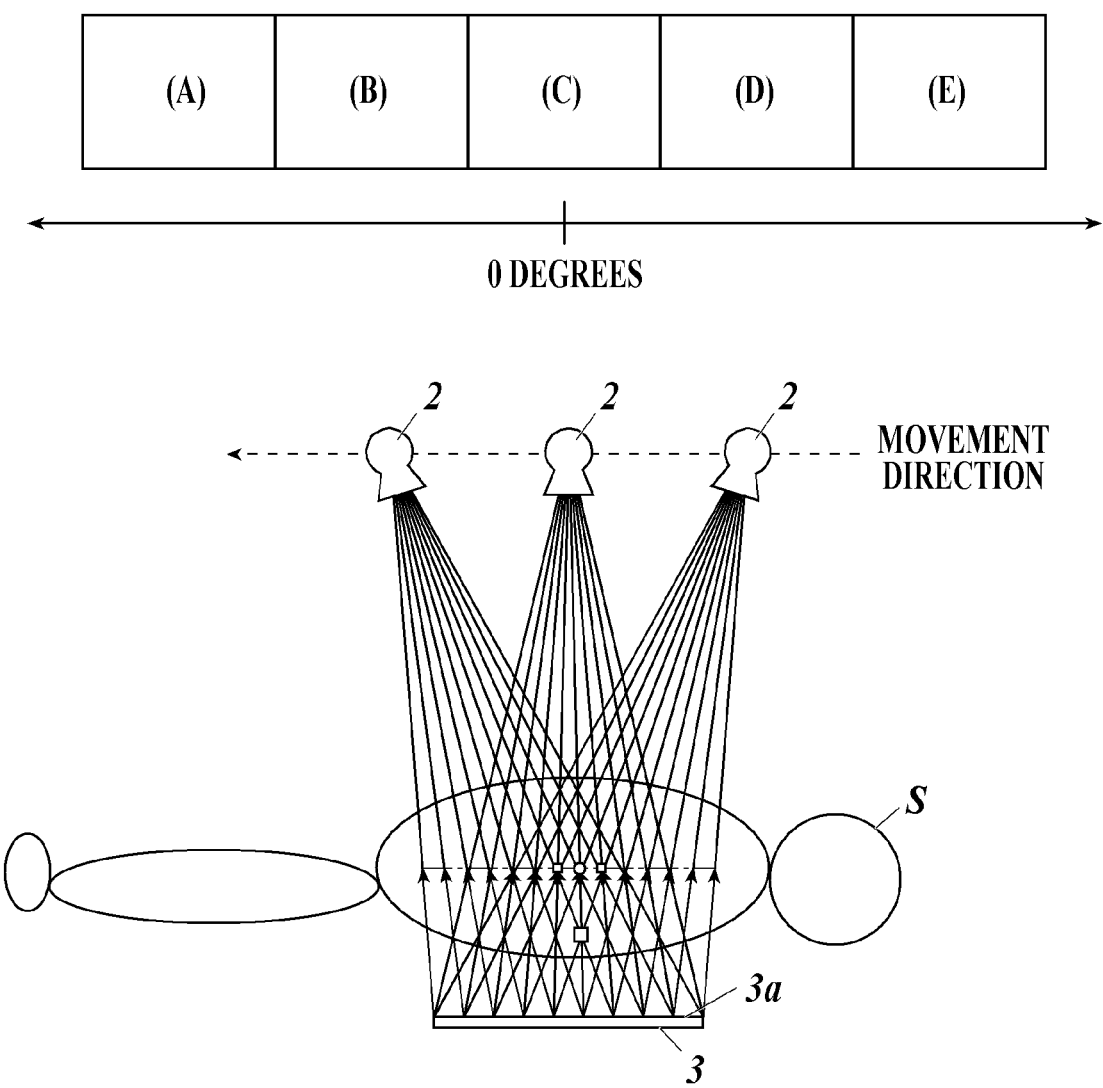
FIG. 35 is a diagram schematically illustrating an imaging method using a radiography system according to an example of the first to fourth embodiments.

For example, in a case where the imaging interval is reduced while the inclination of the radiation emission axis is large and is increased when the inclination is small, the radiation generator 2 performs control as follows. The radiation generator 2 increases the irradiation frame rate in a state in which it is located in a region (A) in which the inclination of the radiation emission axis is large among the regions (A) to (E) illustrated in FIG. 35 ("without thinning-out (short imaging interval)" in FIG. 34) and reduces the irradiation frame rate in a state in which it is located in the region (B) in which the inclination of the radiation emission axis is less than that in the region (A) ("thinning-out 1" in FIG. 34 (for example, the emission of radiation is thinned out every other time)). In addition, the radiation generator 2 further reduces the irradiation frame rate in a state in which it is located in the region (C) in which the inclination of the radiation emission axis is less than that in the region (B) ("thinning-out 2" in FIG. 34 (for example, thinning-out is performed twice each time radiation is emitted)). Then, the radiation generator 2 increases the irradiation frame rate in the region (D) in which the inclination of the radiation emission axis is larger than that in the region (C) ("thinning-out 1") and further increases the irradiation frame rate in the region (E) in which the inclination of the radiation emission axis is larger than that in the region (D) ("without thinning-out (short imaging interval)").

In some cases, it is desirable to change the imaging interval according to the imaging method such that the imaging interval is increased while the inclination of the radiation emission axis is large and is reduced while the inclination is small as described above. In this case, the radiation generator 2 changes the state to the same state as that in "thinning-out 2" in a state in which it is located in the region (A) or (E) in which the inclination of the radiation emission axis is larger among the regions (A) to (E) illustrated in FIG. 35, increases the irradiation frame rate in a state in which it is located in the region (B) or (D) in which the inclination of the radiation emission axis is less than that in the region (A) or (E) ("thinning-out 1" in FIG. 34), and further increases the irradiation frame rate in a state in which it is located in the region (C) in which the inclination of the radiation emission axis is less than that in the region (B) or (D) ("without thinning-out (short imaging interval)" in FIG. 34).

This configuration makes it possible to perform imaging with the amount of radiation required to generate a tomographic image, without unnecessarily irradiating the subject with radiation, and to reduce the exposure dose of the subject.

Example 31

Application (1) of Addition Reading

There is a case where an image resolution equal to or greater than a predetermined value is required or there is a case where high-speed imaging is desired instead of low image resolution, depending on the imaging part and the imaging technique.

In order to solve the problem, the following configuration may be used. In a case where the imaging apparatus 3 reads a radiographic image, the imaging apparatus 3 changes the amount of addition reading (binning) in the pixels which are arranged in at least one of the vertical direction and the horizontal direction in the radiographic image to change the imaging frame rate and then performs imaging.

Specifically, in a case where an imaging part or an imaging technique is selected, the amount of binning, the imaging frame rate, and the degree of thinning-out N (the irradiation frame rate is set to 1/N of the imaging frame rate) are set according to the recommended amount of the selected imaging apparatus and then imaging is performed.

This configuration makes it possible to perform imaging at an appropriately resolution and an appropriate frame rate according to the imaging part and the imaging technique.

In addition, it is possible to increase the number of imaging techniques that can respond to various situations.

Example 32

Application (2) of Addition Reading

As a method that adds the charge accumulated in each pixel of the imaging apparatus and performs reading, there are the following methods (a) and (b).

(a) Analog binning that adds and reads charge on a circuit (b) Digital binning that individually reads charge on a circuit and then adds the read values It is effective to perform addition reading using analog binning that can reduce the reading time, in order to increase the imaging frame rate. However, for example, in a case where the radiographer wants to switch the presence and absence of binning after image capture, or in a case where analog binning is performed and charge is added on the circuit before reading and is likely to exceed a convertible region of the A/D converter 34c of the reader 34 of the imaging apparatus 3, it may be preferable to use at least a part of the addition reading as digital binning.

In order to solve the problem, the imaging device 3 may use analog addition reading as addition reading for the pixels which are arranged in one of the vertical and horizontal directions of the radiographic image and may use digital addition reading as addition reading for the pixels arranged in the other direction.

In this case, it is possible to perform imaging at an appropriate resolution and an appropriate frame rate according to the imaging part and the imaging technique.

In particular, the amount or direction of the analog binning or the digital binning may be adjusted to increase the imaging frame rate of the imaging apparatus 3 and to increase combinations of the imaging frame rates.

For example, in a method, such as tomosynthesis, which performs imaging while moving the radiation generator 2 in predetermined direction, the resolution of the pixels arranged in a direction orthogonal to the movement direction of the radiation generator 2 in the imaging apparatus 3 may be more important than the resolution of the pixels arranged in the movement direction or, conversely, the resolution of the pixels arranged in the movement direction may be more important than the resolution of the pixels arranged in the direction orthogonal to the movement direction.

In this case, for example, the following imaging method can be used: for the pixels arranged in the movement direction of the imaging apparatus 3, charge is added and read by analog binning to increase the frame rate; and, for the pixels arranged in the direction orthogonal to the movement direction of the imaging apparatus 3, the amount of binning in digital binning is adjusted and vice versa.

Example 33

Image Correction Method (1)

If the switching element 32e provided in each pixel of the imaging apparatus 3 is turned off, change can be accumulated in each pixel. If the switching element 32e is turned on, the accumulated charge is output.

In a case where the imaging frame rate increases, there is a problem that the switching element 32e is turned off before the charge accumulated in each pixel is output and the charge that has not been output remains as an afterimage in the next image.

In order to solve the problem, the unexposed image generated at the timing when no radiation is emitted may be used to correct the image in which an afterimage remains (reading efficiency correction).

Specifically, the reading efficiency correction is performed as represented by the following Expression (1):

$$\text{Image}(x,y) \text{ after reading efficiency correction} = \{\text{image}(x,y) \text{ after gain correction} - \text{image}(x,y) \text{ after gain correction before one frame} \times \alpha(x,y)\}/(1-a(x,y)) \quad (1)$$

(where α indicates a correction coefficient (0<α<1) and (x, y) indicates coordinates in an image)

Specifically, the reading efficiency correction is disclosed on, for example, JP 2017-192605 A.

The reading efficiency correction requires the image before one frame. However, in this case, since the unexposed image is used for correction, it is possible to prevent an afterimage from remaining in the exposed image due to the operation of the switching element.

Example 34

Image Correction Method (2)

In some cases, an afterimage remains even after the reading efficiency correction is performed for the unexposed image. In many cases, the afterimage is caused by a time lag (delay in the generation of charge or a lag component) in a case where the photodiode forming the radiation detection element 32d generates charge.

In order to solve the problem, the lag component remaining in the next exposed image may be predicted on the basis of the time interval between the current unexposed image and the next exposed image and may be subtracted from the next exposed image.

The unexposed image includes a lag component generated at the timing when the exposed image of the previous frame is generated. Then, it is possible to calculate how much the lag component is included in the next exposed image from the attenuation characteristics.

The configuration makes it possible to prevent an afterimage from remaining in the exposed image due to the lag component.

Example 35

Image Correction Method (3)

In some cases, a recursive filtering process represented by the following Expression (2) is performed for an image in order to suppress image graininess and line noise:

$$\text{Image after processing of current frame} = \alpha \times \text{image after processing of previous frame} + (1-\alpha) \times \text{Image before processing of current frame} \quad (2)$$

(where α indicates a correction coefficient (0<α<1))

However, in a case where an image of a fast-moving subject is captured, there is a problem that the difference in the position of the subject between the previous exposed frame and the current exposed frame increases and an afterimage of the image before processing is included in the processed image.

In order to solve the problem, an unexposed image obtained immediately before the image to be corrected may be used for the recursive filtering process.

Line noise is noise that is not related to the amount of exposure and a predetermined amount of line noise is included in both the exposed image and the unexposed image. Therefore, the use of the unexposed image for the recursive filtering process makes it possible to average the line noise and to reduce the line noise.

In a case where the previous unexposed image is used, it is possible to suppress graininess and line noise and blurring is less likely to be noticeable even in the case of a fast-moving subject.

In a case where the subject moves pretty fast, blurring is likely to be noticeable even though the recursive filtering process using the unexposed image is performed. Therefore, it is preferable to switch whether to perform the recursive filtering process according to the thinning-out ratio or the movement of the subject.

Example 36

Image Correction Method (4)

A steady-state value X of the image subjected to the recursive filtering process (in a case where radiation is emitted for every other frame) is represented by the following Expression (3):

$$X=1/(1+\alpha) \quad (3)$$

In a case where the recursive filtering processing is performed for the dynamic image obtained by imaging without performing the thinning-out emission of radiation, for example, as can be seen from FIG. 36, the steady-state value is reduced in the first few frames and then returns to the original value.

In contrast, in a case where the recursive filtering processing is performed for the dynamic image obtained by imaging using the thinning-out emission of radiation, a state in which the signal value of the processed image is low is repeated.

For example, in a case where the irradiation frame rate is ½ of the imaging frame rate (the emission of radiation is thinned-out for every other frame), the steady-state value of the image before processing is 1, and the correction coefficient cc is 0.2, the steady-state value X is 0.83.

In a case where the irradiation frame rate is ¼ of the imaging frame rate (the emission of radiation is thinned-out for three frames among four frames), the steady-state value of the image before processing is 1, and the correction coefficient α is 0.2, the steady-state value X is 0.8.

In order to solve the problem, the steady-state value of the thinned-out image may be divided by the value of X.

This configuration makes it possible to return the steady-state value to 1 even in a case where the steady-state value of the image after processing is reduced.

Although a specific calculation formula is omitted here, this example can also be applied to a dynamic image obtained by imaging in which radiation is emitted for every N frames (N−1 frames therebetween are unexposed frames).

Example 37

Image Correction Method (5)

In some cases, a signal remains even after the reading efficiency correction is performed for the unexposed image and the lag component is subtracted. In many cases, this signal is caused by an increase in offset (offset drift) due to an increase in the temperature of the reader 34.

In order to solve the problem, for example, the average value or the mode value of the amount of offset drift of the unexposed image before and after exposure may be subtracted from the exposure image to reduce an offset drift component.

This configuration makes it possible to prevent a signal resulting from the offset drift component from remaining in the exposure image.

In the above-mentioned examples, various types of image correction using the unexposed image have been described. However, in a case where the thinning-out emission of radiation is not performed, image processing is performed using, for example, the exposed image. That is, predetermined image correction is performed for the radiographic image captured in a state in which the imaging frame rate set in the imaging apparatus 3 is N times as high as the irradiation frame rate set in the generation apparatus Image correction different from the above-mentioned image correction is performed for the radiographic image captured in a state in which the imaging frame rate set in the imaging apparatus 3 is equal to the irradiation frame rate set in the generation apparatus.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Applications No. 2018-188191 and No. 2018-188272, both filed on Oct. 3, 2018, is incorporated herein by reference in its entirety.

What is claimed is:

1. A radiation generation control device comprising:
an acquirer that acquires a first signal which instructs emission of radiation;
a first connector that inputs a second signal which indicates a driving state of a radiography apparatus that generates a radiographic image;
a second connector that connects with a radiation generation apparatus that generates radiation; and
a controller that makes the second connector repeatedly output a third signal which instructs emission of radiation with a predetermined period based on the acquired first signal and the input second signal.

2. The radiation generation control device according to claim 1, wherein the second connector is a connector into which one end of a cable having another end connected to the radiation generation apparatus is inserted.

3. The radiation generation control device according to claim 1, wherein the second connector connects with the radiation generation apparatus through a relay that relays a signal.

4. The radiation generation control device according to claim 1, wherein
an irradiation instruction switch that outputs the first signal is connectable to the radiation generation control device, and
the acquirer directly acquires the first signal from the irradiation instruction switch.

5. The radiation generation control device according to claim 1, wherein
a substrate or an apparatus which is provided with an irradiation instruction switch that outputs the first signal is connected to the radiation generation control device, and
the acquirer acquires the first signal output from the irradiation instruction switch through the substrate or the apparatus.

6. The radiation generation control device according to claim 1, wherein the acquirer acquires the first signal output from the irradiation instruction switch through the radiation generation apparatus.

7. The radiation generation control device according to claim 1, wherein the controller outputs a fourth signal that instructs an imaging timing of the radiographic image from the first connector based on a timing when the third signal is output.

8. The radiation generation control device according to claim 7, wherein
the acquirer acquires a fifth signal which instructs a start of capture of a radiographic image and which is output before the first signal, and
the controller outputs the fourth signal also for a period from the acquisition of the fifth signal to the acquisition of the first signal.

9. The radiation generation control device according to claim 8, wherein
the acquirer acquires a sixth signal which instructs preparation for emitting radiation and which is output before the first signal and after the fifth signal, and
the controller outputs the fourth signal also for a period from the acquisition of the sixth signal to the acquisition of the first signal.

10. The radiation generation control device according to claim 7, wherein the controller repeatedly outputs the fourth signal with the same period as that of the third signal.

11. The radiation generation control device according to claim 7, wherein the controller outputs the fourth signal a predetermined time after the output of the third signal.

12. The radiation generation control device according to claim 1, wherein, even if the second signal is input, the controller does not output the third signal until a predetermined standby time elapses after the first signal is acquired.

13. The radiation generation control device according to claim 1, wherein the controller repeatedly outputs the third signal until the number of times the third signal is output reaches a predetermined value or until a predetermined output time elapses after a first output of the third signal.

14. A radiation generation control system comprising:
the radiation generation control device according to claim 1; and
a console which is connected to the radiation generation control device and which sets an operation of the radiation generation control device,
wherein the console sets a number of times the third signal is output or an output time for which the third signal is repeatedly output in the radiation generation control device before the radiation generation control device outputs the third signal.

15. The radiation generation control system according to claim 14, wherein the console includes a display, and
the console displays the number of times the third signal is output or the output time for which the third signal is repeatedly output, which has been set in the radiation generation control device, on the display.

16. The radiation generation control system according to claim 15, wherein, if the second signal is input to the first connector of the radiation generation control device, the console displays information indicating that irradiation is possible on the display.

17. The radiation generation control system according to claim 15, wherein, while the radiation generation control device is outputting the third signal, the console displays information indicating that radiation is being emitted on the display.

18. A radiography system comprising:
a radiation generation apparatus that generates radiation;
a radiography apparatus that generates a radiographic image; and
the radiation generation control device according to claim 1.

19. The radiography system according to claim 18, wherein the radiography system is capable of capturing a still image while the radiation generation control device is not connected.

20. The radiation generation control device according to claim 1, wherein the first signal indicates a turn-on of an irradiation instruction by an irradiation instruction switch and each occurrence of the third signal instructs the radiation generation apparatus to cause a respective emission of radiation.

* * * * *